US009622761B2

(12) United States Patent
Chana et al.

(10) Patent No.: US 9,622,761 B2
(45) Date of Patent: Apr. 18, 2017

(54) KNEE BALANCING FOR REVISION PROCEDURES

(71) Applicant: Synvasive Technology, Inc., El Dorado Hills, CA (US)

(72) Inventors: Barjinder S. Chana, Reno, NV (US); Michael G. Fisher, Reno, NV (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 63 days.

(21) Appl. No.: 14/564,451

(22) Filed: Dec. 9, 2014

(65) Prior Publication Data
US 2015/0100059 A1    Apr. 9, 2015

Related U.S. Application Data

(63) Continuation of application No. 13/937,749, filed on Jul. 9, 2013, now abandoned, which is a continuation
(Continued)

(51) Int. Cl.
*A61B 17/17* (2006.01)
*A61B 17/15* (2006.01)
(Continued)

(52) U.S. Cl.
CPC ........ *A61B 17/1764* (2013.01); *A61B 17/155* (2013.01); *A61B 17/157* (2013.01);
(Continued)

(58) Field of Classification Search
CPC ...................... A61F 2/4684; A61B 2017/0268
See application file for complete search history.

(56) References Cited

U.S. PATENT DOCUMENTS

| 4,501,266 A | * | 2/1985 | McDaniel | ............ | A61B 17/025 |
| | | | | | 600/587 |
| 4,567,886 A | * | 2/1986 | Petersen | ............... | A61B 17/154 |
| | | | | | 606/88 |

(Continued)

FOREIGN PATENT DOCUMENTS

| FR | WO 9104715 A1 * | 4/1991 | ........... A61B 17/154 |
| WO | WO-9104715 A1 | 4/1991 | |

(Continued)

OTHER PUBLICATIONS

"U.S. Appl. No. 12/757,486, Final Office Action mailed May 17, 2012", 10 pgs.
(Continued)

*Primary Examiner* — Zade Coley
(74) *Attorney, Agent, or Firm* — Schwegman Lundberg & Woessner, P.A.

(57) ABSTRACT

Methods, systems and devices are provided for facilitating a surgical procedure on a knee, particularly, a revision total knee replacement procedure. Prior femoral and tibial prostheses are removed. A cut end of a distal femur is engaged with a femoral adjustment member, which will typically center itself about an intermedullary rod placed into the femur. The lateral and medial forces exerted by lateral and medial sides of the femoral adjustment member and the cut tibial plateau against each other are measured. The femoral adjustment member is adjusted to apply and or adjust tension to the lateral collateral ligament and/or the medial collateral ligament based an the measured forces, for example, such that the measured lateral force and the measured medial force are matched. Based on the position of the adjusted femoral member, guided clean-up cuts for placement of a new femoral prostheses are made on the cut end of the distal femur.

19 Claims, 57 Drawing Sheets

Related U.S. Application Data of application No. 12/757,486, filed on Apr. 9, 2010, now Pat. No. 8,506,571, which is a continuation-in-part of application No. 12/605,259, filed on Oct. 23, 2009, now abandoned.

(60) Provisional application No. 61/107,973, filed on Oct. 23, 2008.

(51) Int. Cl.
    *A61F 2/46*     (2006.01)
    *A61B 17/72*    (2006.01)
    *A61F 2/38*     (2006.01)

(52) U.S. Cl.
    CPC ............ *A61B 17/72* (2013.01); *A61F 2/4684* (2013.01); *A61F 2/38* (2013.01)

(56) References Cited

U.S. PATENT DOCUMENTS

| | | | |
|---|---|---|---|
| 4,759,350 A * | 7/1988 | Dunn | A61B 17/154 606/82 |
| 5,197,488 A * | 3/1993 | Kovacevic | A61F 2/38 600/587 |
| 5,360,016 A | 11/1994 | Kovacevic | |
| 5,470,354 A | 11/1995 | Hershberger et al. | |
| 5,486,178 A * | 1/1996 | Hodge | A61B 17/155 606/102 |
| 5,540,696 A | 7/1996 | Booth, Jr. et al. | |
| 5,562,675 A * | 10/1996 | McNulty | A61B 17/155 606/102 |
| 5,597,379 A | 1/1997 | Haines et al. | |
| 5,624,444 A * | 4/1997 | Wixon | A61B 17/155 606/88 |
| 5,649,929 A | 7/1997 | Callaway | |
| 5,656,785 A | 8/1997 | Trainor et al. | |
| 5,662,656 A * | 9/1997 | White | A61B 17/155 606/86 R |
| 5,688,280 A | 11/1997 | Booth, Jr. et al. | |
| 5,688,282 A * | 11/1997 | Baron | A61B 17/15 606/87 |
| 5,720,752 A | 2/1998 | Elliott et al. | |
| 5,733,292 A * | 3/1998 | Gustilo | A61B 17/025 606/86 R |
| 5,735,904 A | 4/1998 | Pappas | |
| 5,776,137 A | 7/1998 | Katz | |
| 5,800,438 A | 9/1998 | Tuke et al. | |
| 5,860,980 A | 1/1999 | Axelson, Jr. et al. | |
| 5,911,723 A | 6/1999 | Ashby et al. | |
| 6,022,377 A | 2/2000 | Nuelle et al. | |
| 6,056,756 A * | 5/2000 | Eng | A61B 17/155 606/87 |
| 6,077,270 A | 6/2000 | Katz | |
| 6,096,082 A | 8/2000 | Stegmuller et al. | |
| 6,575,980 B1 | 6/2003 | Robie et al. | |
| 6,758,850 B2 | 7/2004 | Smith et al. | |
| 6,916,325 B2 * | 7/2005 | Kana | A61F 2/4657 606/89 |
| 7,101,377 B2 | 9/2006 | Cortellessa et al. | |
| 7,104,996 B2 | 9/2006 | Bonutti | |
| 7,261,719 B1 * | 8/2007 | Twomey | A61B 5/1072 606/102 |
| 7,374,563 B2 * | 5/2008 | Roger | A61B 17/155 606/88 |
| 7,442,196 B2 * | 10/2008 | Fisher | A61B 17/02 606/120 |
| 7,488,324 B1 * | 2/2009 | Metzger | A61B 17/155 33/511 |
| 7,578,821 B2 * | 8/2009 | Fisher | A61B 17/02 600/587 |
| 8,506,571 B2 | 8/2013 | Chana et al. | |
| 2003/0045883 A1 * | 3/2003 | Chow | A61B 17/155 606/88 |
| 2003/0187452 A1 * | 10/2003 | Smith | A61B 17/025 606/88 |
| 2004/0019382 A1 * | 1/2004 | Amirouche | A61B 5/0031 623/18.11 |
| 2004/0039398 A1 | 2/2004 | Cortellessa et al. | |
| 2004/0064191 A1 | 4/2004 | Wasielewski | |
| 2004/0097951 A1 * | 5/2004 | Steffensmeier | A61B 5/107 606/102 |
| 2005/0177170 A1 * | 8/2005 | Fisher | A61B 17/02 606/88 |
| 2005/0209605 A1 | 9/2005 | Grimm et al. | |
| 2005/0240196 A1 | 10/2005 | Davis et al. | |
| 2005/0267485 A1 * | 12/2005 | Cordes | A61B 17/02 606/88 |
| 2006/0241569 A1 | 10/2006 | DiSilvestro | |
| 2007/0073305 A1 * | 3/2007 | Lionberger | A61B 17/155 606/87 |
| 2007/0219559 A1 | 9/2007 | Heavener et al. | |
| 2007/0232959 A1 | 10/2007 | Couture et al. | |
| 2007/0234819 A1 | 10/2007 | Amirouche et al. | |
| 2007/0293868 A1 * | 12/2007 | Delfosse | A61B 17/025 606/88 |
| 2008/0177261 A1 | 7/2008 | Mcminn | |
| 2008/0306413 A1 | 12/2008 | Crottet et al. | |
| 2009/0043310 A1 | 2/2009 | Rasmussen | |
| 2010/0063509 A1 | 3/2010 | Borja et al. | |
| 2013/0296860 A1 | 11/2013 | Chana et al. | |

FOREIGN PATENT DOCUMENTS

| | | |
|---|---|---|
| WO | WO-2005037121 A1 | 4/2005 |
| WO | WO-2005089681 A2 | 9/2005 |
| WO | WO-2005122899 A1 | 12/2005 |
| WO | WO-2006047005 A2 | 5/2006 |

OTHER PUBLICATIONS

"U.S. Appl. No. 12/757,486, Non Final Office Action mailed Apr. 10, 2012", 10 pgs.

"U.S. Appl. No. 12/757,486, Notice of Allowance mailed Apr. 10, 2013", 11 pgs.

"U.S. Appl. No. 12/757,486, Response filed Mar. 23, 2012 to Restriction Requirement mailed Mar. 14, 2012", 2 pgs.

"U.S. Appl. No. 12/757,486, Response filed Apr. 25, 2012 to Non Final Office Action mailed Apr. 10, 2012", 25 pgs.

"U.S. Appl. No. 12/757,486, Response filed May 21, 2012 to Final Office Action mailed May 17, 2012", 9 pgs.

"U.S. Appl. No. 12/757,486, Restriction Requirement mailed Mar. 14, 2012", 9 pgs.

"U.S. Appl. No. 13/937,749, Non Final Office Action mailed Sep. 17, 2014", 10 pgs.

"European Application Serial No. 10825339.4, Extended European Search Report mailed Jun. 18, 2014", 6 pgs.

"European Application Serial No. 200901078, Office Action mailed Jul. 10, 2012", 2 pgs.

"European Application Serial No. 200901078, Response filed Jan. 17, 2013 to Office Action mailed Jul. 10, 2012", 10 pgs.

"International Application Serial No. PCT/US2009/062846, International Search Report mailed Jan. 10, 2013", 4 pgs.

"International Application Serial No. PCT/US2009/062846, Written Opinion mailed Jan. 13, 2010", 8 pgs.

"International Application Serial No. PCT/US2010/030524, International Preliminary Report on Patentability mailed Apr. 24, 2012", 1 pg.

"International Application Serial No. PCT/US2010/030524, International Search Report mailed Jun. 10, 2010", 3 pgs.

"International Application Serial No. PCT/US2010/030524, Written Opinion mailed Jun. 10, 2010", 13 pgs.

"International Application Serial No. PCT/US2011/031980, International Preliminary Report on Patentability mailed Oct. 18, 2012", 8 pgs.

"International Application Serial No. PCT/US2011/031980, International Search Report mailed Jun. 28, 2011", 3 pgs.

(56) References Cited

OTHER PUBLICATIONS

Eckhoff, D. G, et al., "Three-Dimensional Morphology and Kinematics of the Distal Part of the Femur Viewed in Virtual Reality", Journal of Bone & Joint Surgery, vol. 85-A, Supplement 4, (2003), 97-104.

Mihalko, W. H, et al., "Comparison of Ligament-Balancing Techniques During Total Knee Arthroplasty", Journal of Bone & Joint Surgery, vol. 85-A, Supplement 4,, (2003), 132-135.

Murray, D. G, et al., "Variable Axis Total Knee Surgical Technique", Howmedica Surgical Techniques, Howmedica, Inc., (1977), 2-7.

Ries, M. D, et al., "Soft-Tissue Balance in Revision Total Knee Arthroplasty", Journal of Bone & Joint Surgery, vol. 85-A, Supplement 4,, (2003), 38-42.

\* cited by examiner

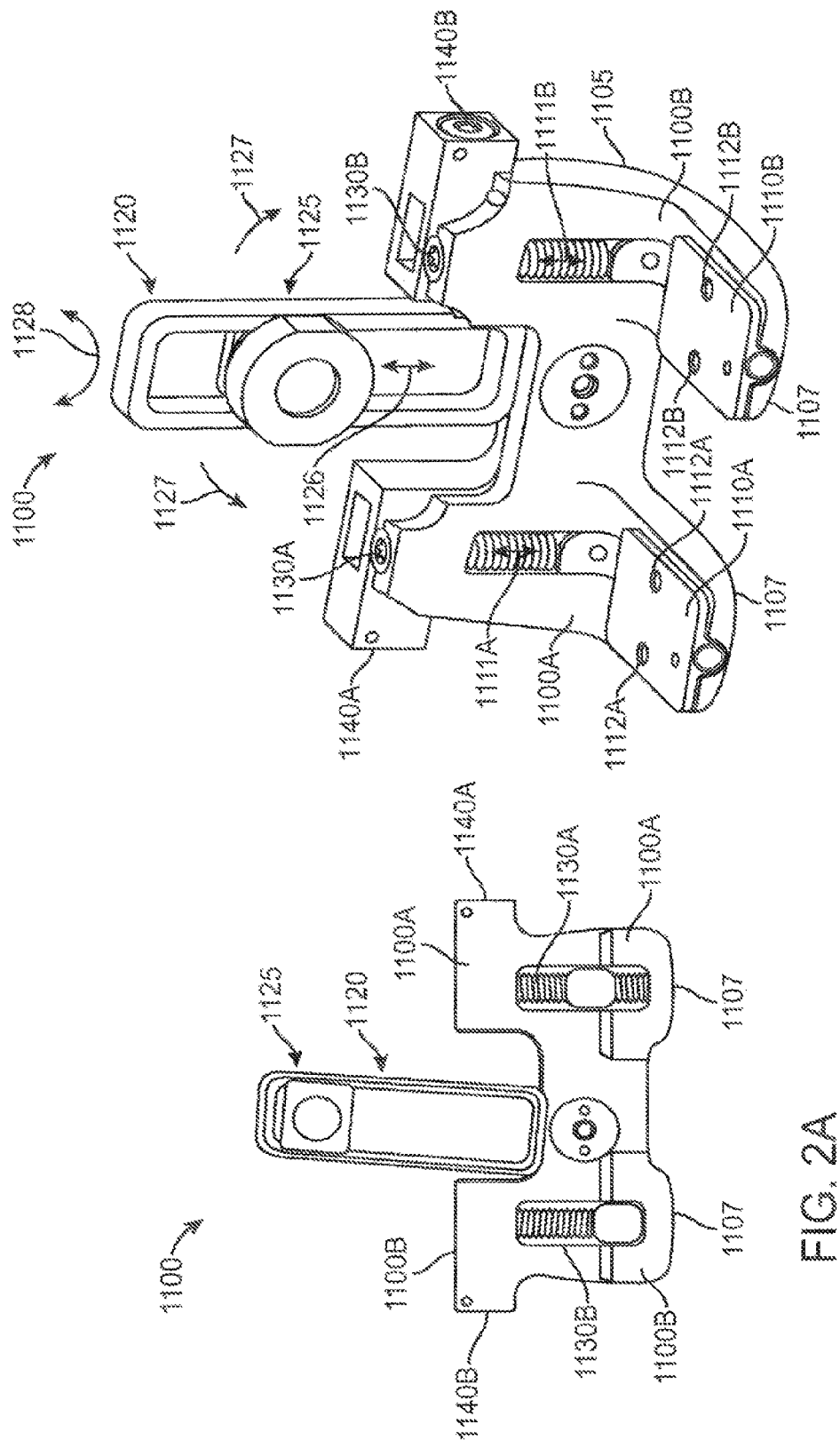

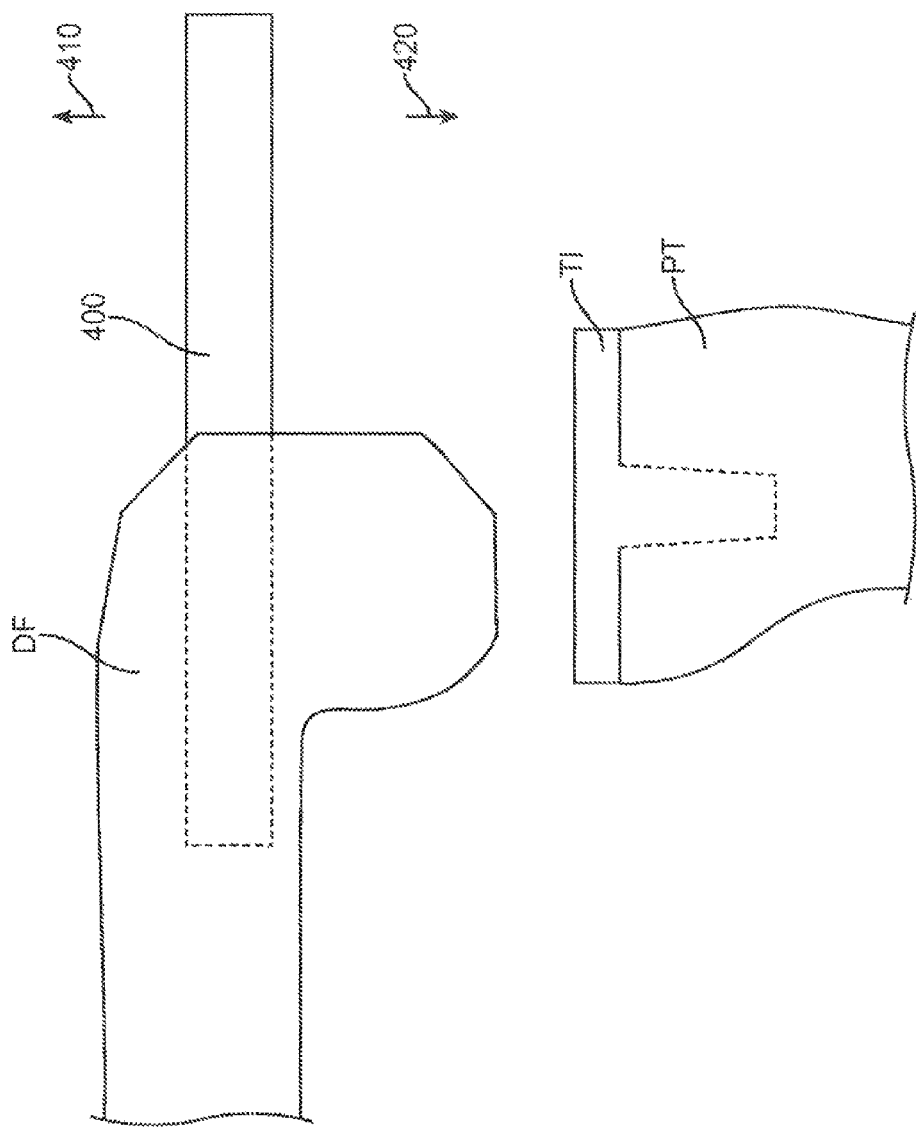

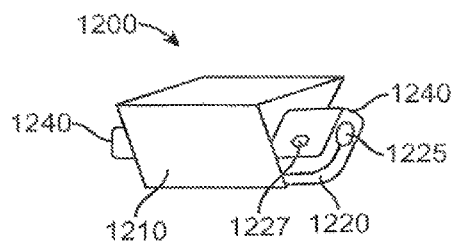
FIG. 4D1
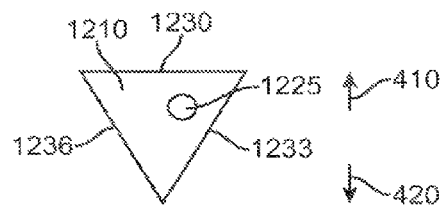
FIG. 4D2
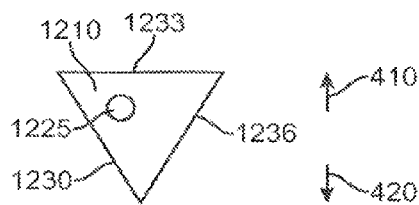
FIG. 4D3
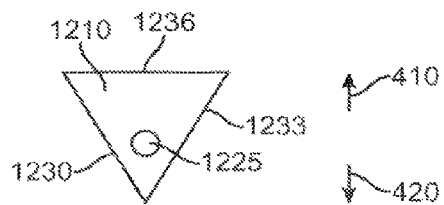
FIG. 4D4
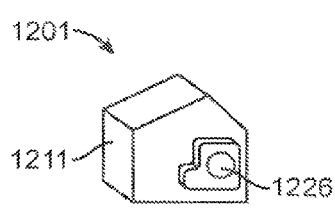
FIG. 4D5
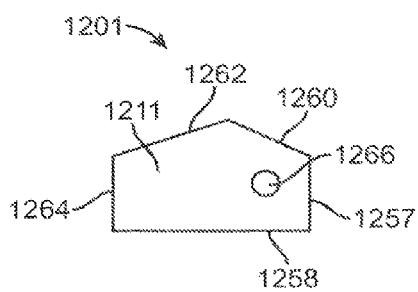
FIG. 4D6

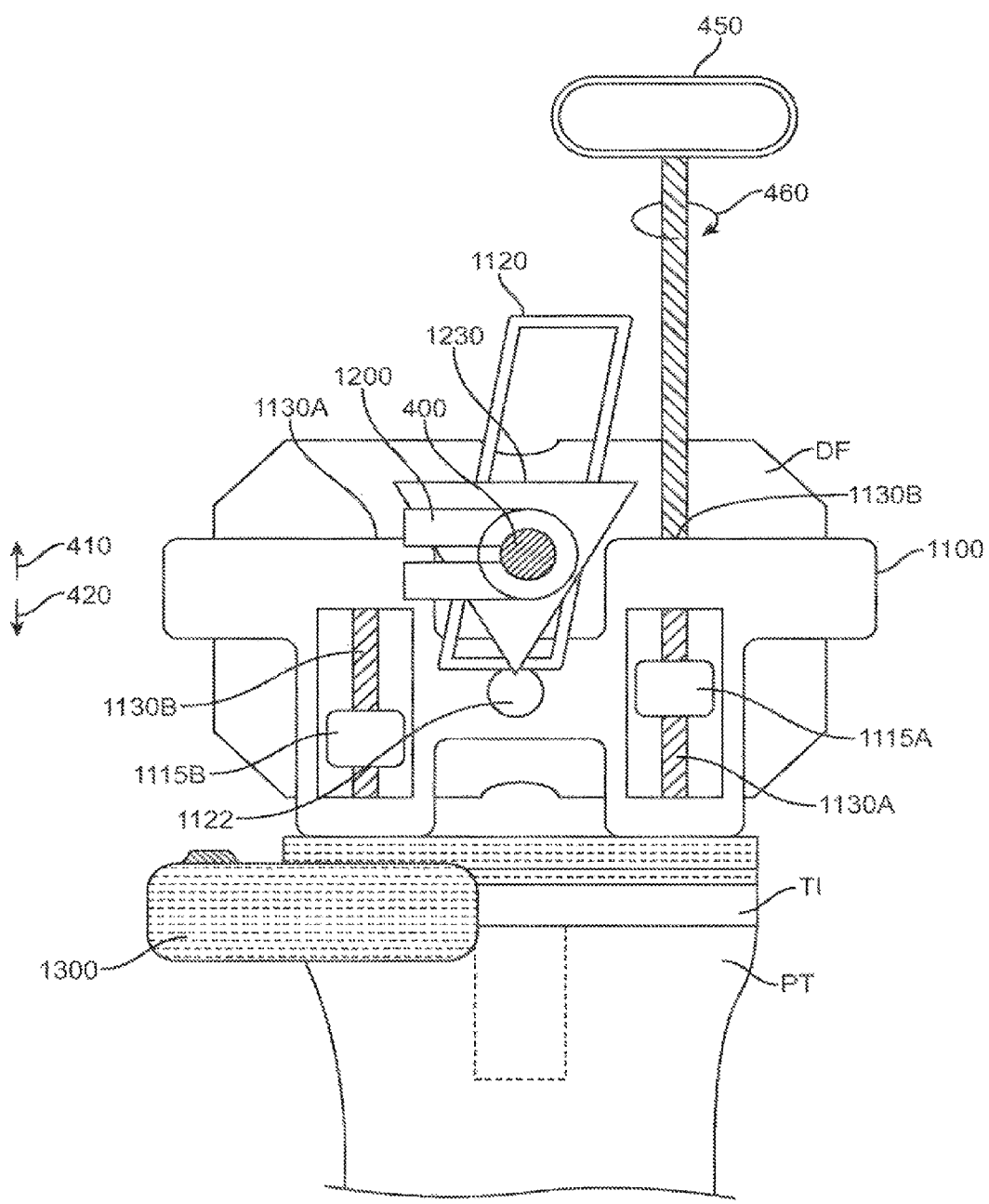
FIG. 4G1

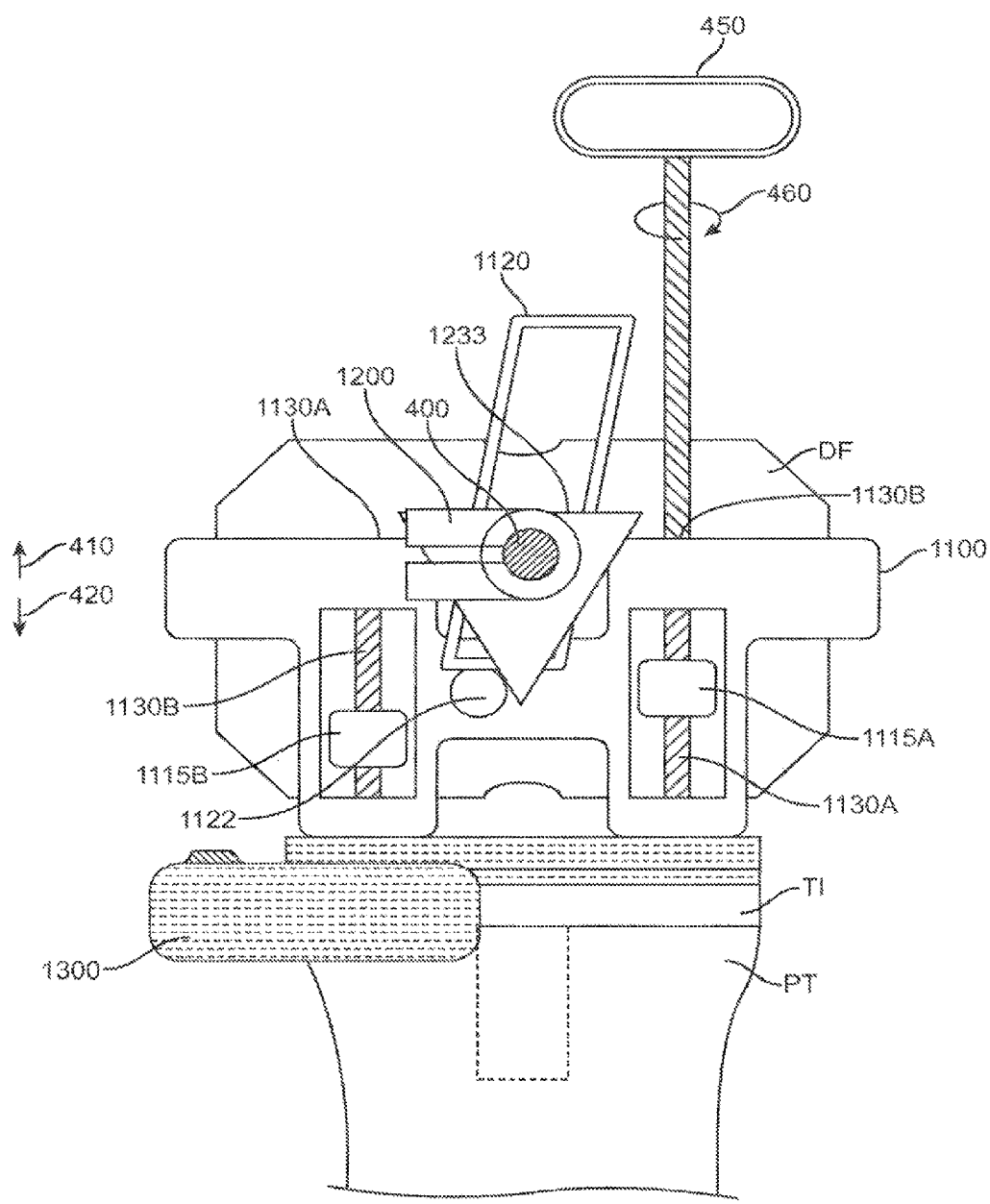
FIG. 4G2

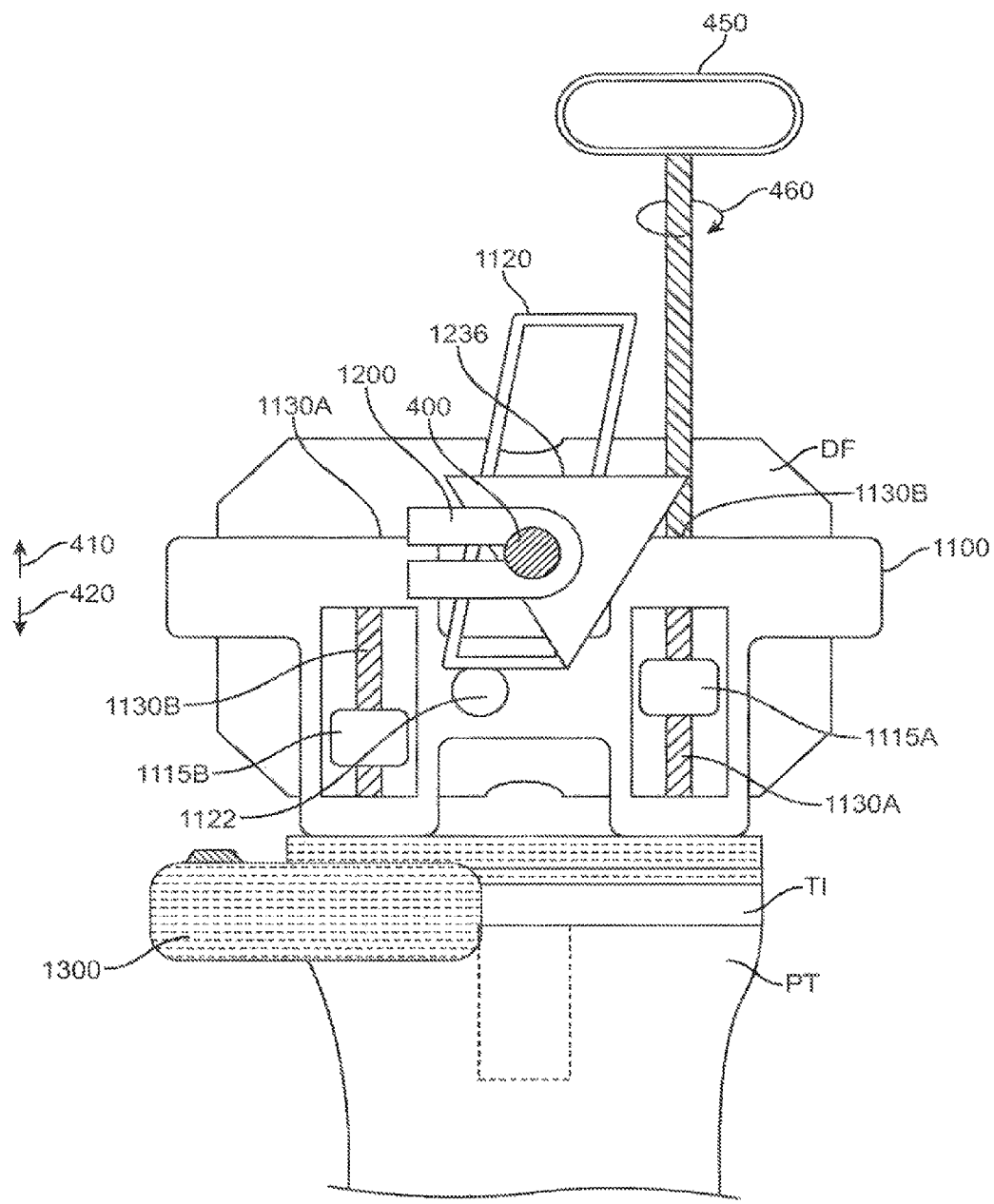
FIG. 4G3

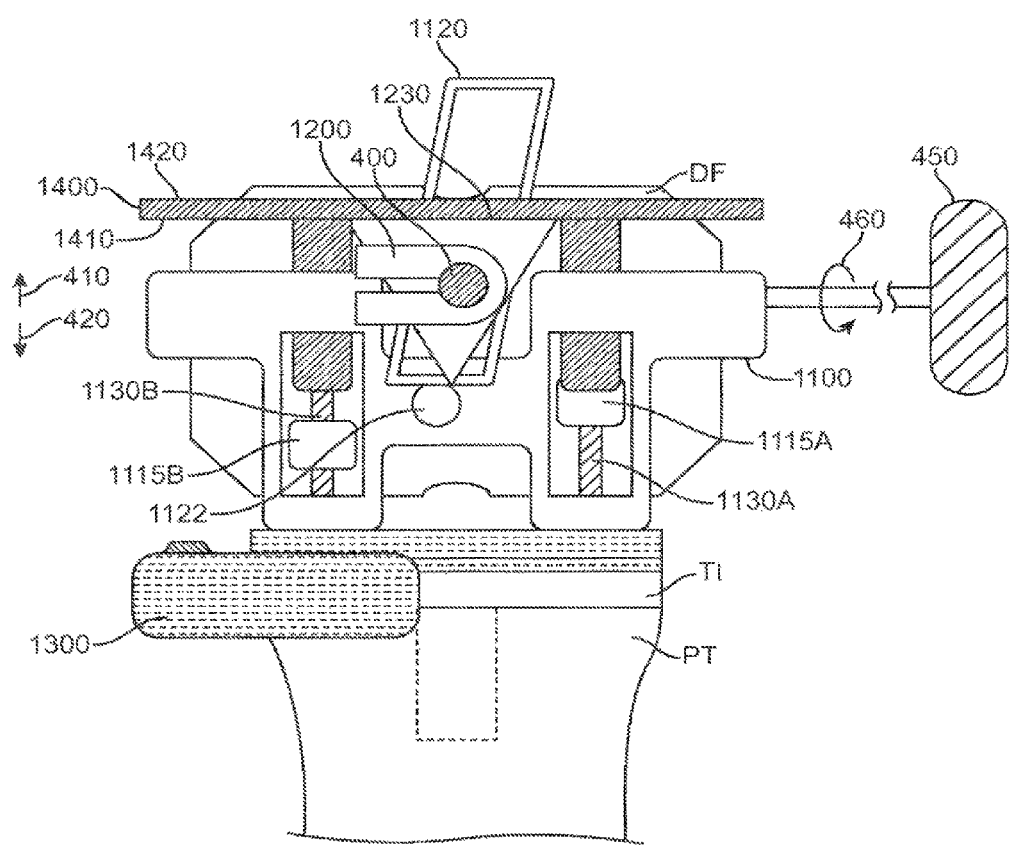
FIG. 4H1

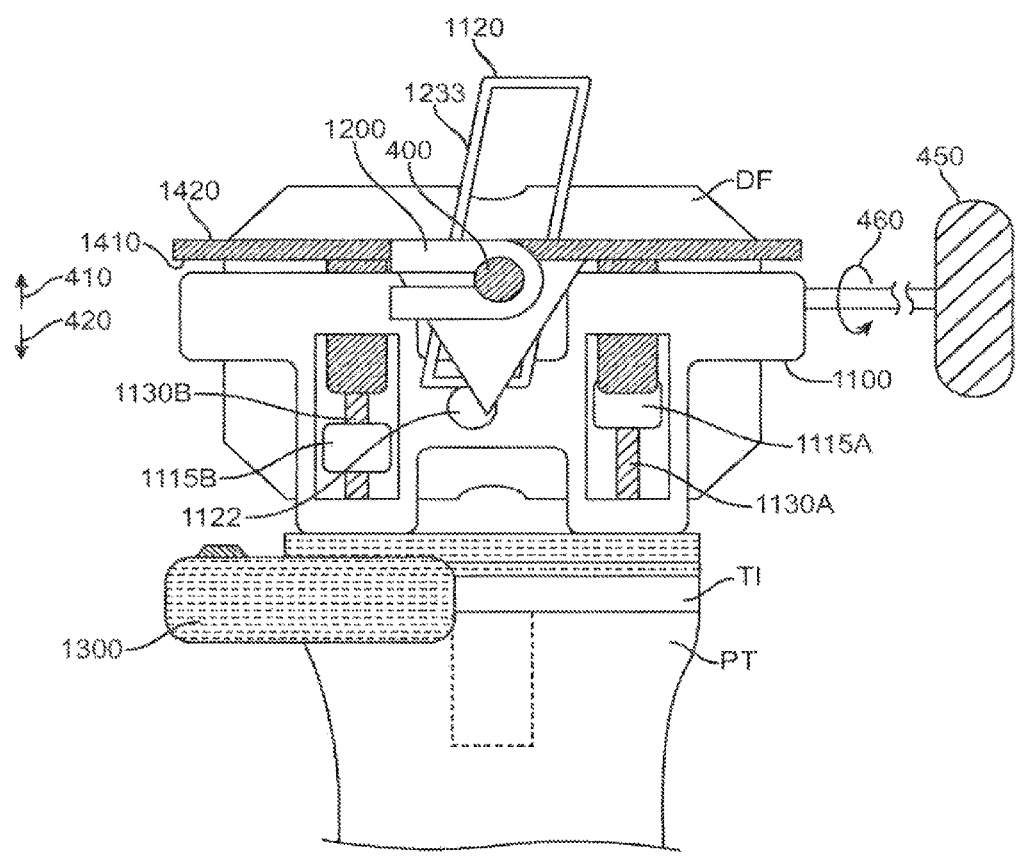
FIG. 4H2

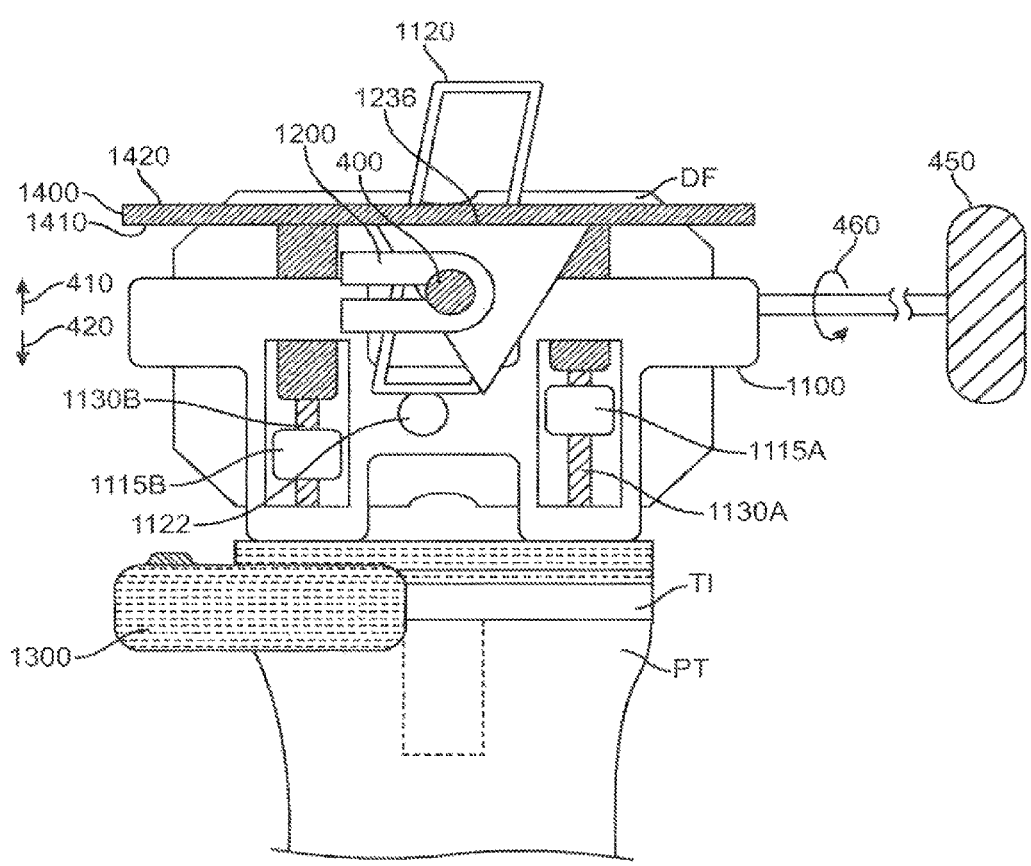
FIG. 4H3

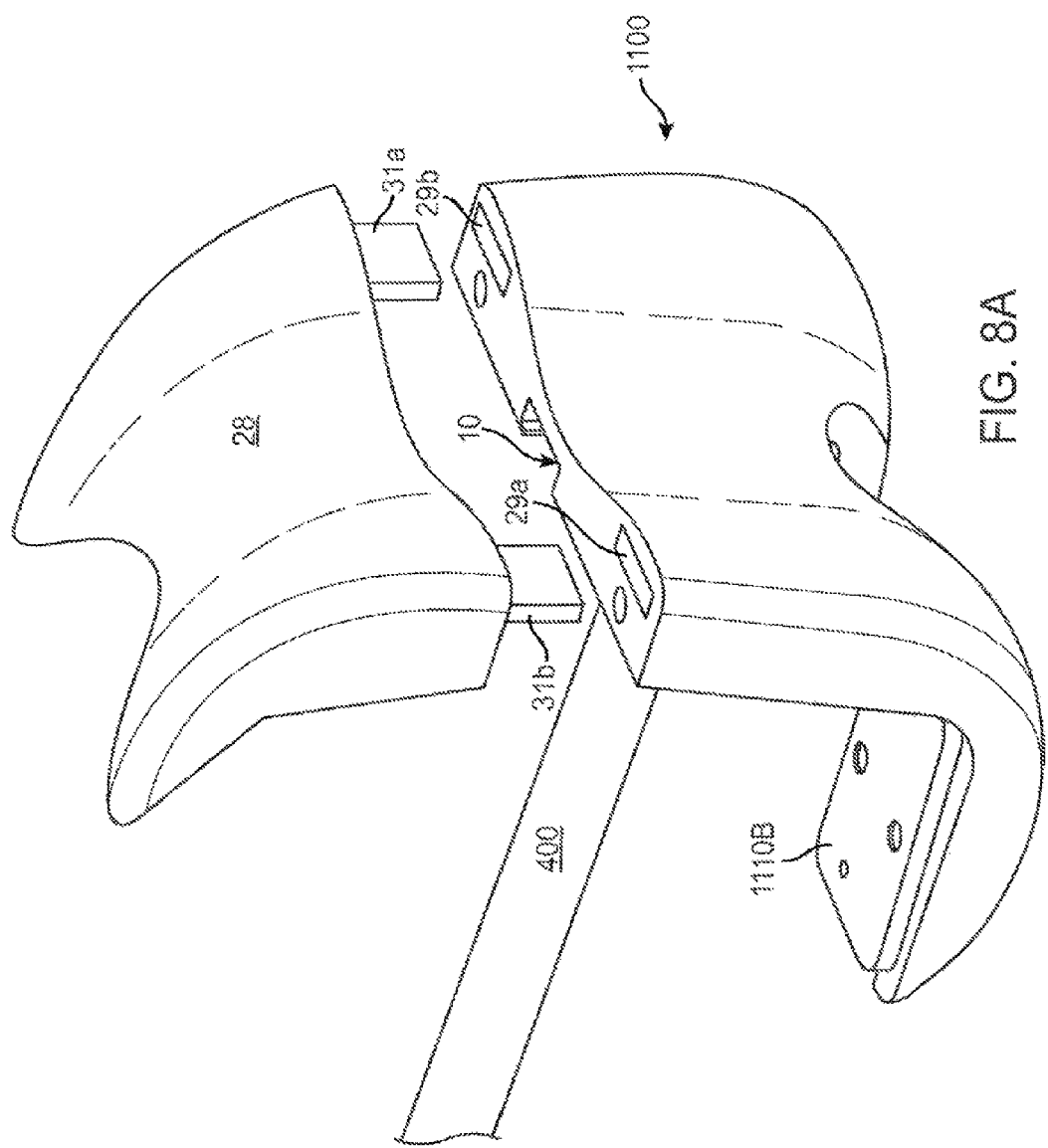

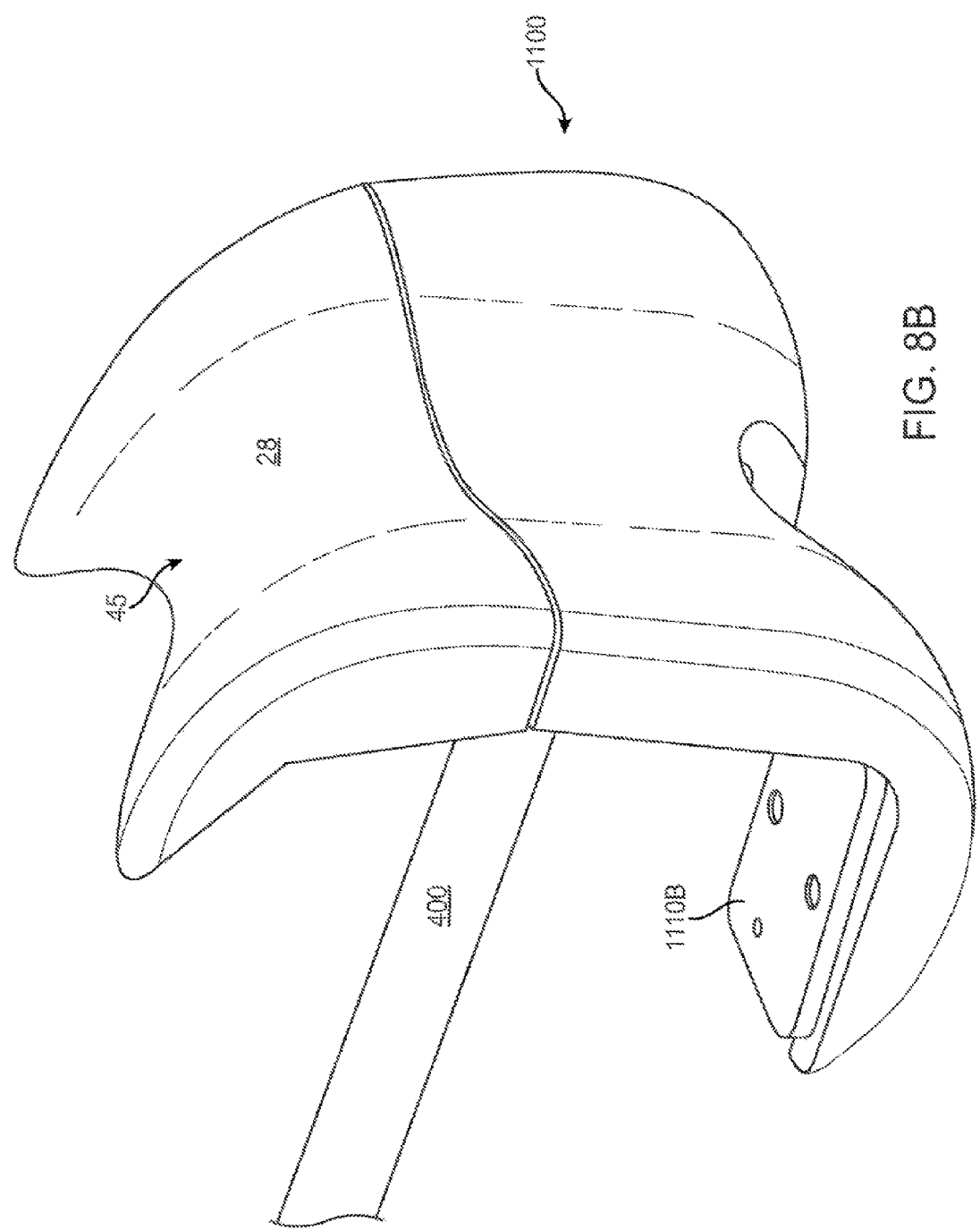

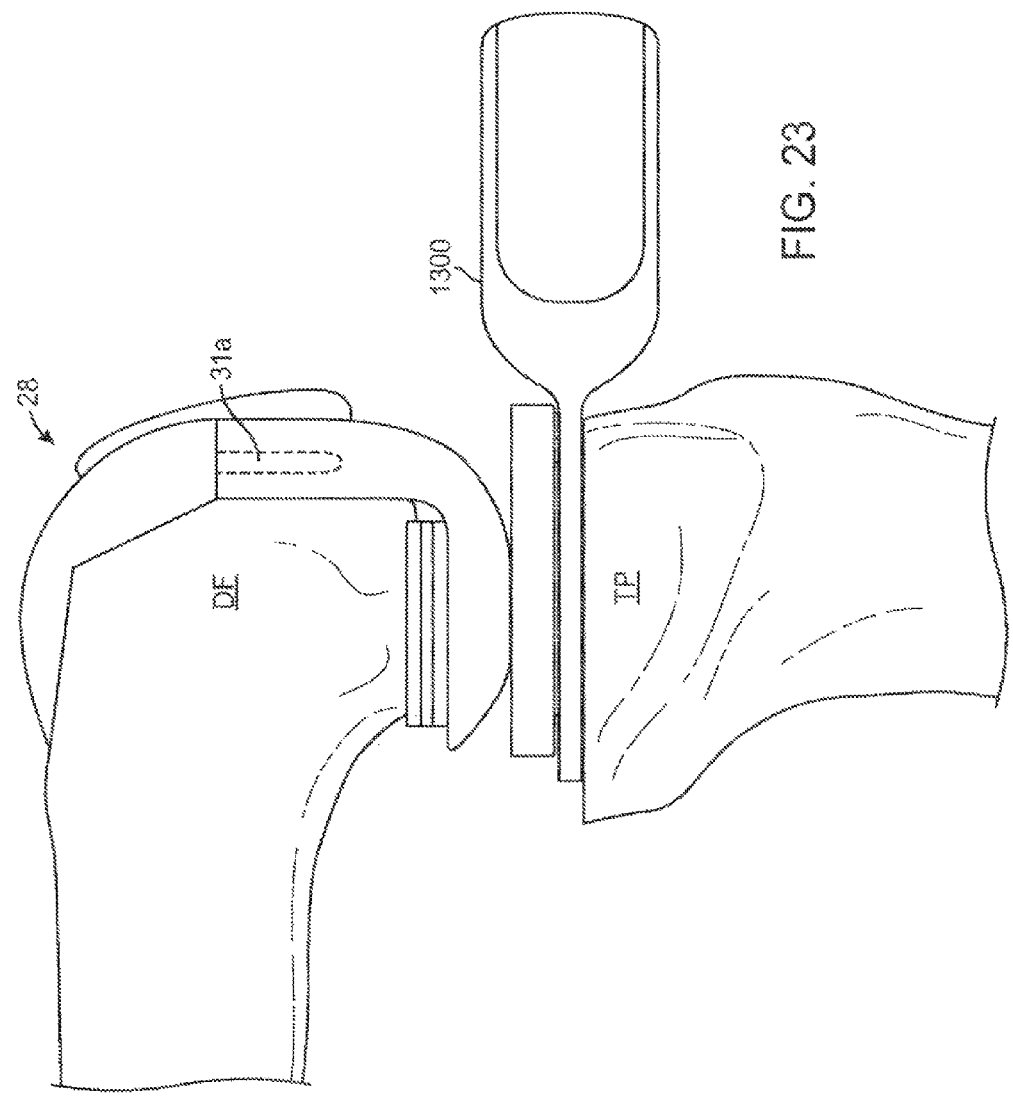

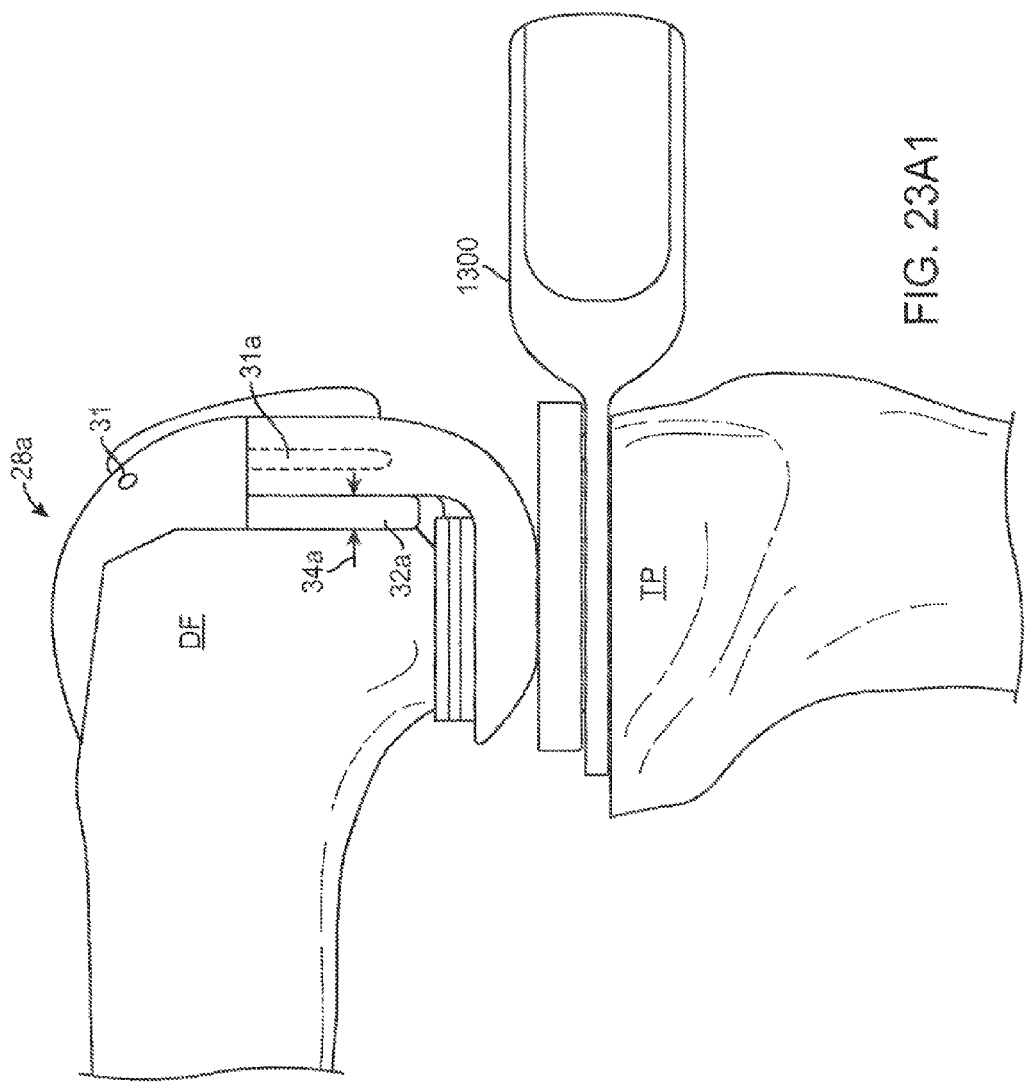

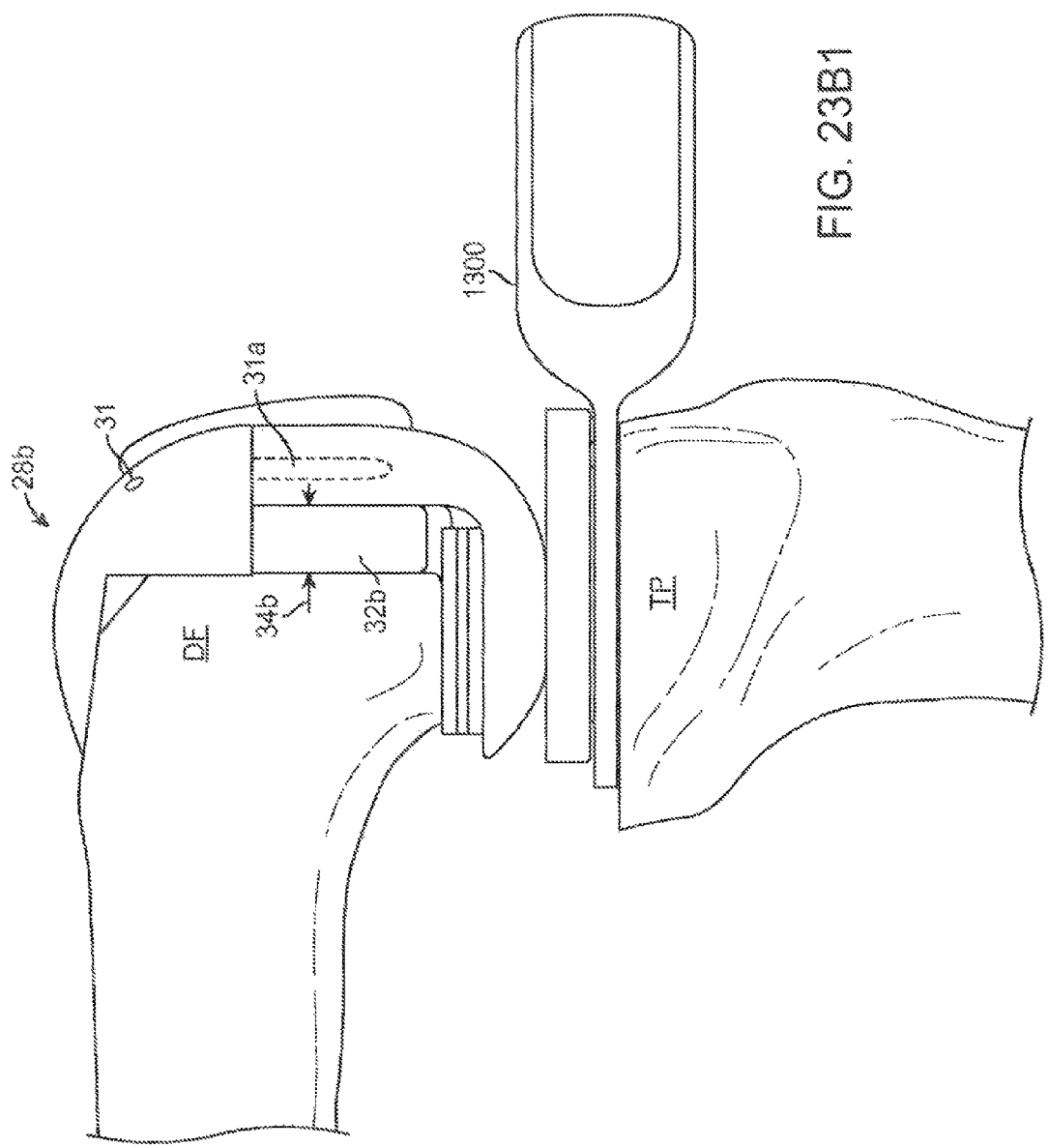
FIG. 23B1

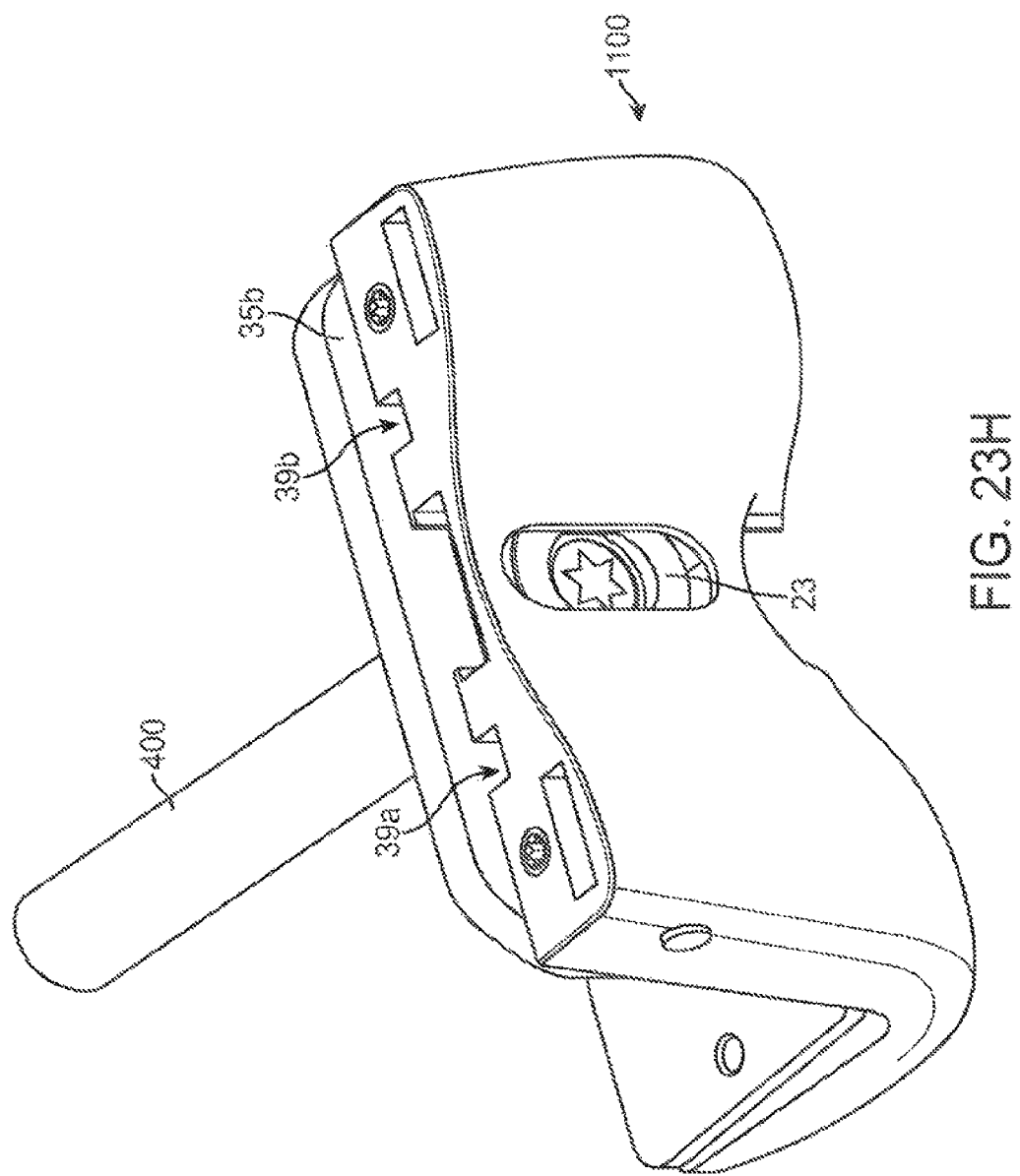

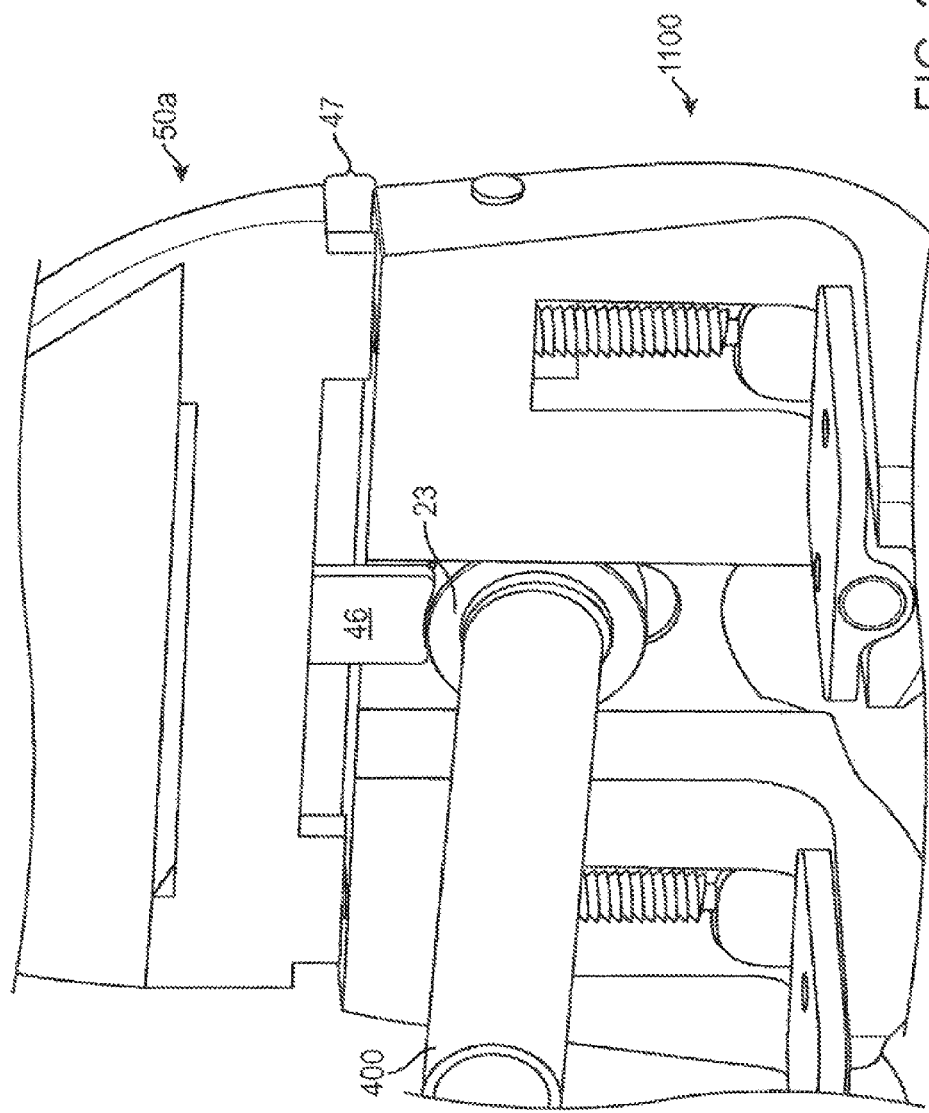

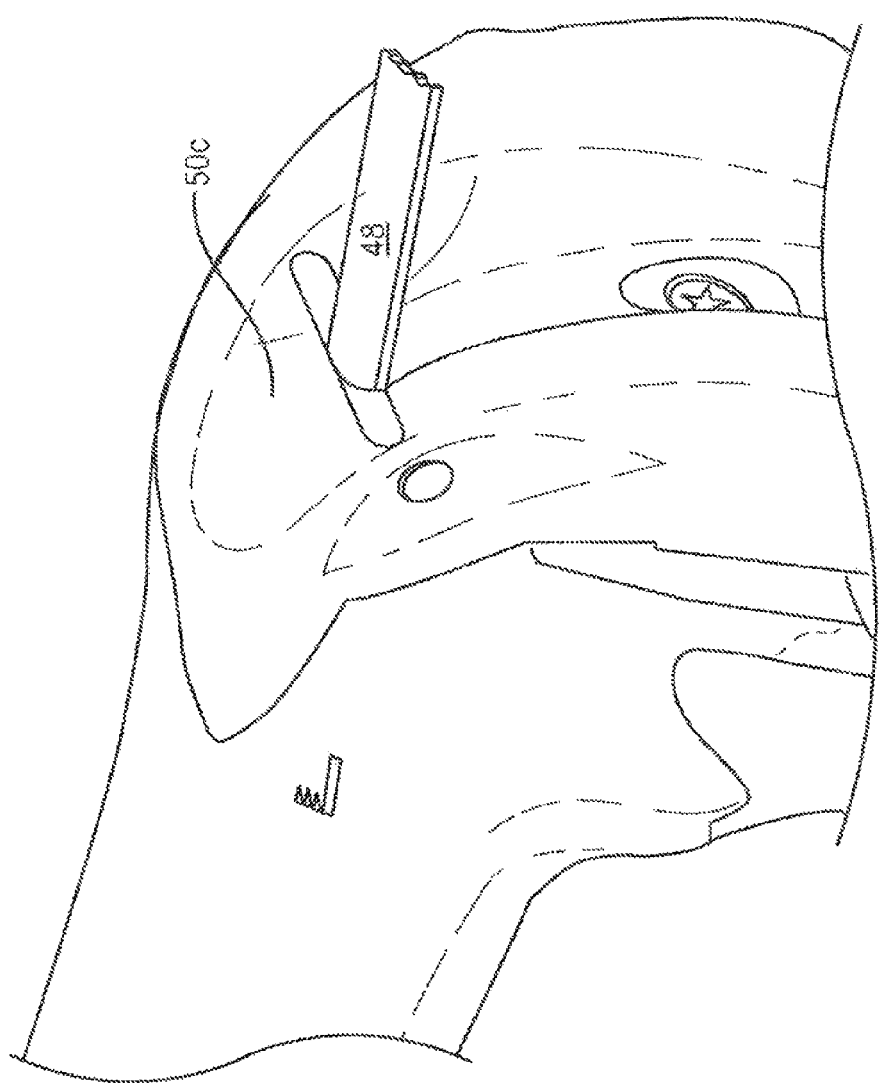

KNEE BALANCING FOR REVISION PROCEDURES

CROSS-REFERENCE TO RELATED APPLICATIONS

The present application is a continuation of U.S. application Ser. No. 13/937,749, filed on Jul. 9, 2013, which is a continuation of U.S. application Ser. No. 12/757,486, filed on Apr. 9, 2010, now issued as U.S. Pat. No. 8,506,571, which is continuation-in-part of U.S. application Ser. No. 12/605,259, filed Oct. 23, 2009, which is a non-provisional of U.S. Provisional Application No. 61/107,973 filed Oct. 23, 2008, the entire contents of which are incorporated herein by reference.

BACKGROUND OF THE INVENTION

The present invention relates generally to medical and surgical devices, systems and methods. More specifically, the invention relates to devices, systems and methods for enhancing knee surgery procedures, in particular, knee replacement procedures and specifically revision total knee replacement procedures.

The knee is generally defined as the point of articulation of the femur with the tibia. Structures that make up the knee include the distal femur, the proximal tibia, the patella, and the soft tissues, including ligaments, within and surrounding the knee joint. The knee is generally divided into three compartments: medial (the inside part of the knee), lateral (the outside part of the knee), and patellofemoral (the joint between the kneecap and the femur). The medial compartment comprises the medial joint surfaces of the femur, tibia, and the meniscus wedged therebetween. The lateral compartment comprises the lateral joint surfaces of the femur, tibia, and the meniscus wedged therebetween. The patellofemoral compartment comprises the joint between the undersurface of the kneecap or patella and the femur. Four ligaments are especially important in the stability, alignment and functioning of the knee: 1) the anterior cruciate ligament; 2) the posterior cruciate ligament; 3) the medial collateral ligament; and 4) the lateral collateral ligament. In an arthritic knee, protective cartilage at the point of articulation of the femur with the tibia is often worn away, allowing the femur to directly contact the tibia. This bone-on-bone contact can cause significant pain, discomfort, and disability for a patient and will often necessitate knee replacement or knee arthroplasty.

Under certain circumstances, a previously implanted prosthetic knee joint may need to be replaced by a new prosthetic knee joint in a procedure called knee revision surgery or revision TKA. Common causes for needing revision TKA include: infection, instability, including specifically flexion instability, femoral component mal-rotation causing poor patellar tracking, and loosening of the prosthetic implants from the bone to which they were attached. Instability is often attributable to poor balancing of the soft tissue during the index or primary TKA.

Revision TKA procedures share some similarities with TKA procedures with respect to components being implanted, such as the prosthetic femur, tibia, and patella. In revision TKA, the old femoral component and tibial component of the prosthetic knee joint are most often removed. Removing the old prosthetic components can be very time consuming, and often large segments of bone may come off with the removed prostheses. As such, empirical landmarks that might otherwise be used to reference proper balance and position for the revision TKA femoral and tibial components are often undistinguishable. The quality of the femoral bone uncovered during revision TKA is often severely osteoporotic, lacking external structural integrity often due to stress shielding caused by poor balancing. Bone quality is enhanced by normal compressive stress forces, conversely, bone quality will deplete if the bone is shielded from those same stress forces.

Like with TKA, a challenge in revision TKA is to properly balance ligament tension, especially in the medial and lateral collateral ligaments, through a full range of motion of the knee, for example, from a fully extended to a fully flexed position, or vice versa. The collateral ligaments, which connect the distal femur and the proximal tibia on the medial and lateral aspects of the knee, account for much of the stability and movement of the knee. If one of the collateral ligaments is too lax or too tight relative to the other collateral ligament, the knee will typically be unstable, range of motion may be limited, the patella may track improperly, and/or the femur and tibia may wear unevenly, leading to arthritis and pain which may often necessitate another repeat surgery. Thus, it is imperative for the short and long-term success of a revision TKA procedure to achieve balanced ligament tension in the knee through a full range of motion.

Balancing ligament tension during any knee replacement surgery is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur. Thus, the natural knee exhibits a rotary laxity that allows the tibia to rotate through a limited internal and external arc, during knee flexion. Additionally, the femur translates anteriorly and posteriorly as the tibia is being flexed about the femur, bringing yet another movement variable. Thus, the ligaments of the knee, along with the femur, tibia and patella create a dynamic bio-mechanism, making ligament tension balancing in knee replacement surgeries challenging. Many articles and studies have been devoted to ligament tension balancing in TKA, such as: Mihalko, W. H. et al., *Comparison of Ligament-Balancing Techniques During Total Knee Arthroplasty*, Jnl. Bone & Jt. Surg., Vol. 85-A, Supplement 4, 2003, 132-135; Eckhoff, D. G. et al., *Three-Dimensional Morphology and Kinematics of the Distal Part of the Femur Viewed in Virtual Reality*, Jnl. Bone & Jt. Surg., Vol. 85-A, Supplement 4, 2003, 97-104; and Ries, M. D. et al., *Soft-Tissue Balance in Revision Total Knee Arthroplasty*, Jnl. Bone & Jt. Surg., Vol. 85-A, Supplement 4, 2003, 38-42.

Balancing a knee specifically during revision TKA is further complicated by the poor quality of bone often encountered and/or missing portions of the bone itself. Balancing techniques and instruments for balancing a knee during revision TKA often reference from the femoral intramedullary canal, specifically due to the fact the external femoral bone quality is not suitable for fixating balancing instruments. Additionally, the femoral intramedullary canal is often used to establish the anterior-posterior location of the replacement femoral component.

The components of a revision TKA femoral knee prosthesis may be selected to have specific sizes and to be specifically positioned to balance ligament tension. Revision TKA procedures may involve making further distal cuts across the distal end of the femur, anterior and posterior cuts, and angled anterior and posterior chamfer cuts to help secure the femoral component solidly in place. The surgeon attempts to make these femoral bone cuts to achieve a position and orientation of the femoral prosthetic component so as to optimally balance ligament tension through a full range of motion of the knee, and to achieve balance specifically of and between the flexion axis and the extension axis. However, it is often very challenging to position the femoral bone cuts and femoral prosthetic component to provide ideal ligament tension through the full range of motion of the knee. This is due primarily to a "trade-off" often facing the surgeon between optimal fixation vs. optimal soft-tissue balancing. Secure fixation is required, but if chosen at the expense of proper balancing, there is a distinct possibility the revision TKA will also fail for some of the same reasons as the primary knee including poor balancing leading to flexion instability and/or stress shielding, for example. The human femur has a natural bow or radius of approximately 70-120 cm along its length. Due to the natural radius of the femur, placing a long intermedullary rod up the femoral intramedullary canal to establish the anterior-posterior (A-P) location of the femoral component often results in the rod skiving anteriorly as it is inserted deep into the femoral diaphysis while also shifting posteriorly outside the distal femur. Locating off of this rod, or establishing the A-P location of the femoral component off of the rod in such a skewed position, will compromise the balance of the knee between the flexion axis and the extension axis.

A number of devices and techniques have been described that attempt to facilitate ligament balancing during a TKA procedure. These devices and techniques may also find use for revision TKA procedures. Some techniques, such as those described in U.S. Pat. No. 5,733,292, involve trial prosthesis components which are used after femoral and tibial bone cuts are made to assess ligament tension. Some devices, such as those described in U.S. Pat. No. 6,758,850, are used to measure a gap between the distal femur and proximal tibia in extension and to help a surgeon recreate that same gap when the knee is in flexion. Other "gap checking" devices are described in U.S. Pat. No. 6,575,980. Other devices have been developed to help measure an amount of ligament tension or to apply a desired amount of tension to the ligaments. U.S. Pat. No. 4,501,266, for example, describes a knee distraction device for applying a desired amount of tension. Many paddle-like devices have been suggested for applying or measuring tension across a knee joint, such as the devices described in U.S. Pat. Nos. 5,597,379; 5,540,696; 5,800,438; 5,860,980; 5,911,723; and 6,022,377. Other methods and devices include those described in co-assigned U.S. Pat. Nos. 7,442,196, and 7,574,821, as well as co-assigned and co-pending U.S. application Ser. No. 11/149,944 , Ser. No. 12/544,897 , and Ser. No. 12/609,666 each of which are incorporated herein by reference.

Additional information relating to attempts to address the problems described above may be found in U.S. Pat. Nos. 5,470,354; 5,656,785; 7,104,996 and U.S. Patent Application Publication Nos. 2005/0209605; 2005/0240196; 2005/0267485; 2006/0241569; 2007/0219559; 2007/0232959; and PCT Publication Nos. WO 2005/089681; WO 2005/037121; WO 2006/047005, for example. However, each one of these references suffers from one or more of the above-identified disadvantages.

For at least the above reasons, a need exists for improved devices, systems and methods for enhancing knee replacement surgery and specifically for dynamically balancing ligaments during knee replacement to improve range of motion, stability, and patellar tracking of the prosthetic knee joint. Additionally, such devices would allow for secure fixation to the femur via the intramedullary canal, without being biased by the natural bow of the femoral canal, and without the intramedullary canal dictating the balance point of and between the flexion axis and the extension axis of the femur. Ideally, such devices and methods would allow a surgeon to achieve a desired ligament tension balance before committing to and making final bone cuts to the femur. Such devices would ideally be simple to use in conjunction with existing knee replacement procedures and equipment such as prosthesis templates, measurement guides, cutting guides, and saw blades or burs. At least some of these objectives will be met by the present invention.

BRIEF SUMMARY OF THE INVENTION

Methods, systems and devices are provided for facilitating a surgical procedure on a knee, in particular, a revision total knee replacement procedure. Prior femoral and at least a portion of the tibial prostheses are removed. A cut end of a distal femur is engaged with a femoral adjustment member. The lateral force and the medial force exerted by lateral and medial sides of the femoral adjustment member and tibial prosthesis against each other are measured. The femoral adjustment member is adjusted to apply and/or adjust tension to the lateral collateral ligament and/or the medial collateral ligament based on the measured forces, for example, so that the measured forces are matched. Thus, the invention provides a quantifiable and repeatable measurement of forces caused by knee ligaments. These measurements can facilitate the balancing of knee ligaments during surgical procedures on the knee. Based on the position of the adjusted femoral member, guide cuts for placement of a new femoral prosthesis may be made on the cut end of the distal femur. The new femoral prosthesis will therefore be implanted and positioned such that the adjacent knee ligaments are well balanced.

In a first aspect, embodiments of the invention provide a method for facilitating a surgical procedure on a knee. An intermedullary rod is inserted into the femoral intermedullary canal of a femur. Once inserted into the canal, a portion of the intermedullary rod extends distally outward from a cut distal end of the femur. A femoral adjustment member is slid over this distally extending portion so as to engage the cut distal end of the femur with the femoral adjustment member. The femoral adjustment member comprises a lateral femoral portion and a medial femoral portion, and may also provide a trochlear groove femoral member. A lateral force exerted by the lateral femoral portion and a lateral tibial portion of a tibial plateau against one another is measured. A medial three exerted by the medial femoral portion and a medial tibial portion of the tibial plateau against one another is measured. The femoral adjustment member is then adjusted based on the measured lateral and medial forces to apply and/or adjust tension to the lateral collateral ligament and/or the medial collateral ligament. The femoral adjustment member may be adjusted so that the measured lateral force matches the medial force.

Typically, the femoral adjustment member is adapted to self-adjust to allow for positioning flush upon the face of the recut distal femur, without being influenced by the interior-posterior insertion angle of the rod, when it is slid over the distally extending portion of the rod. The femoral adjustment member may position itself about the intermedullary rod while also maintaining moveable freedom to center itself about the rod. The femur may be rotated about the intermedullary rod, with the medial side of the femoral adjustment member as a balancing fulcrum.

The femoral adjustment member may be locked in a fixed position relative to the intermedullary rod, for example, by sliding a locking clamp over the distally extending portion of the intermedullary rod and tightening the locking clamp, or by locking the femoral adjustment member over a low-profile distally extending portion of the intermedullary rod via a short set screw or short cam lock screw. The trochlear groove femoral member may be integral to the adjustable femoral member, or removably attachable to the adjustable femoral member. Additionally, the trochlear groove femoral member may come in several thicknesses to allow for gap balancing the extension gap to the flexion gap.

A force sensor may be used to measure the medial and/or lateral forces. The force sensor is inserted between the engaged femoral adjustment member and the tibial plateau. A lateral side of the force sensor is disposed between as lateral tibial portion of the tibial plateau and the lateral femoral portion of the femoral adjustment member. A medial side of the force sensor is disposed between a medial tibial portion of the tibial plateau and the medial femoral portion of the femoral adjustment member. The force sensor may comprise a sensor selected from the group consisting of piezoelectric sensors, force sensing resistors, strain gauges, load cells, other pressure sensors and other three sensors. A visual display which displays the measured lateral force and/or the measured medial force may he coupled with the force sensor.

To measure the medial and/or lateral forces, the following procedure may be used. A voltage is transmitted to a sensor element of a thin force sensing portion of the force sensor. The voltage after having passed through the sensor element is measured. A percentage of the voltage passed through the sensor element relative to the voltage transmitted to the sensor element is measured. The measured force is derived from the percentage.

In some instances, the tibial plateau may be engaged with a tibial member. The tibial member and femoral adjustment member are engaged primarily within a joint space between the cut surfaces of the proximal tibial and the distal femur.

Adjusting the femoral member may comprise enlarging a joint space between at least part of the distal femur or the tibial plateau to apply tension to at least one of the medial collateral ligament or the lateral collateral ligament. The space primarily at a medial side of the knee and/or at a lateral side of the knee may be enlarged.

At least one of the lateral femoral portion or medial femoral portion of the femoral adjustment member may be adjustable. The femoral adjustment member may comprise at least one stationary member. At least one of the lateral adjustment portion or medial adjustment portion may be coupled with the at least one stationary member. The femoral adjustment member may be adjusted by adjusting the position of the lateral adjustment portion and/or the medial adjustment portion relative the at least one stationary member and the cut distal end of the femur. The lateral adjustment portion and/or the medial adjustment portion may comprise at least one screw which may be turned to adjust its relative position. Both the lateral femoral portion and the medial femoral portion may be adjustable and the lateral femoral portion and the medial femoral portion may be separately adjustable. The lateral femoral portion and medial femoral portion may be rotated relative to each other to adjust the femoral adjustment member.

Often times, a first cutting guide is engaged and aligned with the adjusted femoral adjustment member. The first cutting guide may be locked in place relative to the adjusted femoral adjustment member and distal femur. A position for placing a first at least one bone cut on the distal femur may be determined based on the relative position of the first cutting guide. A first at least one bone cut may be made on the distal femur based on the determined position. Then, the first cutting guide and the femoral adjustment member may be removed, and a second cutting guide may be engaged on the distal femur based on the first at least one bone cut. A reference tongue may be engaged with the first at least one bone cut and the second cutting guide may be positioned based on the position of the reference tongue. A second at least one bone cut on the distal femur may be then be made. The second cutting guide may then be removed and a femoral prosthesis may be attached to the cut distal femur.

In another aspect, embodiments of the invention provide a system for enhancing a surgical procedure on a knee. The system comprises a femoral adjustment member and a self-centering mechanism. The femoral adjustment member is removably engagable with a cut distal end of a femur and comprises a femoral body, a lateral adjustable member, a medial adjustable member, and a trochlear groove member. The femoral body has a lateral side and a medial side. The lateral adjustable member is disposed on the lateral side of the femoral body. The medial adjustable member is disposed on the medial side of the femoral body. The lateral adjustable member and medial adjustable member are separately adjustable to adjust the position of the femoral body relative to the cut distal end of the femur and to apply tension to the lateral collateral ligament and/or the medial collateral ligament of the knee. The self-centering sliding mechanism is disposed on the femoral body between the lateral side and medial side. The sliding mechanism is configured to slide over an intermedullary rod extending from the cut end of the distal femur and to position the femoral body about the cut end of the distal femur. The trochlear groove member is disposed between the medial and lateral adjustable members and is configured with a concave, radial shape.

The system typically further comprises a force sensor adapted to measure a lateral force exerted between the lateral side of the femoral body and a lateral side of the tibial plateau, and to measure a medial force exerted between the medial side of the femoral body and as medial side of the tibial plateau. The force sensor may comprise a sensor selected from the group consisting of piezoelectric sensors, force sensing resistors, strain gauges, load cells, other pressure sensors and other force sensors. The system may further comprise a visual display coupled to the force sensor. The visual display is adapted to display the measured lateral force and the measured medial force.

In many embodiments, the system further comprises a tibial member having a lateral side and a medial side.

In many embodiments, the sliding mechanism may comprise a sliding coupler. The sliding coupler may be translatable in a first anterior-posterior direction, rotatable in a second varus-valgus direction, and rotatable in a third flexion-extension direction and connected to a pivotable sliding mechanism frame.

In many embodiments, adjusting one adjustable member relative to the opposite adjustable member causes the femoral body to rotate relative to the posterior distal end of the femur when the femoral adjustment member is coupled thereto.

In many embodiments, the lateral-adjustment member comprises a lateral adjustment element and the medial adjustment member comprises a medial adjustment element. The lateral adjustment element and medial adjustment element may be selected from the group consisting of screws, pins, levers, rods, springs, spring-loaded mechanisms and shape memory materials.

In some embodiments, the lateral adjustable member comprises a lateral paddle and the medial adjustable member comprises a medial paddle. The system may further comprise as set of augmenting members adapted to couple to the lateral paddle or the medial paddle as to modify the size thickness of the paddles.

In some embodiments, the femoral body comprises at least one distal femoral portion emulating the cut distal surface of the femur and at least one posterior condylar portion emulating the posterior condylar surfaces of the femur. The at least one posterior condylar portion may comprise a lateral femoral posterior condylar member and a medial femoral posterior condylar member. At least a portion of the lateral adjustable element may extend from the lateral femoral posterior condylar member and at least a portion of the medial adjustable element may extend from the medial femoral posterior condylar member.

In many embodiments, the system further comprises a locking clamp slidable over a distally extending portion of the intermedullary rod. The locking clamp is adapted to lock the femoral adjustment member in a fixed position abutted flush against the cut distal end of the femur creating a balance plane from which to balance the extension axis to the flexion axis. The locking clamp may be further adapted to be tightened using a screwing tool, with the lateral adjustable member and medial adjustable member also adapted to be adjusted using the same screwing tool. The locking clamp may comprise a rotatable body having a lumen offset from the center of the rotatable body.

In many embodiments, the system further comprises a first cutting guide. The first cutting guide is engagable with the femoral adjustment member and is adapted to facilitate making one or more bone cuts on the cut distal end of the femur. The system may further comprise a reference tongue adapted to couple to the one or more bone cuts made on the cut distal end of the femur. The system may also comprise a second cutting guide engagable with the cut distal end of the femur based on the position of the one or more bone cuts made on the distal femur facilitated by the first cutting guide.

In a preferred embodiment of the invention, a method for balancing tension of ligaments during knee replacement surgery comprises inserting a first end of an intermedullary rod into an intermedullary canal of a femur such that the rod at least partially follows the bow of the femur to establish a first axis. A second end of the intermedullary rod is positioned to extend distally outward from a cut distal end of the femur. The second end has a coupling configured for movement in at least the first axis and a second axis. A femoral adjustment member, having a lateral femoral portion and a medial femoral portion, is slid over the second end to engage the cut distal end of the femur with the femoral adjustment member. The coupling moves about the second axis independent of influence from the first axis when the femoral adjustable member is flush against the cut distal end of the femur. A lateral force exerted by a lateral femoral portion of the femoral adjustment member and a lateral tibial portion of a tibial plateau is measured against one another and a medial force exerted by a medial femoral portion of the femoral adjustment member and a medial tibial portion of the tibial plateau are measured against one another. The femoral adjustment member is adjusted based on the measured lateral force and the measured medial force to apply tension to at least one of a first and a second knee ligament.

In many embodiments, the first axis is a flexion/extension direction and the second axis is a varus/valgus direction. The first knee ligament is the lateral collateral ligament and the second knee ligament is the medial collateral ligament.

In many embodiments, the coupling comprises an outer race and an inner race. The inner race is a portion of a ball configured to allow the outer race to rotate around the inner race in a varus/valgus direction and in a flexion/extension direction. Adjusting the femoral adjustment member allows full range patella tracking. The second end of the intermedullary rod is adjustable in at least the first axis and the second axis.

In other embodiments, the femoral adjustment member is adapted to self-adjust and position itself about the intermedullary rod when engaged with the distally extending portion of the intermedullary rod.

In other embodiments, measuring comprises inserting a force sensor having a lateral side and a medial side between the engaged femoral adjustment member and the tibial plateau so that the lateral side of the force sensor is disposed between the lateral tibial portion of the tibial plateau and the lateral femoral portion of the femoral adjustment member, and a medial side of the force sensor is disposed between the medial tibial portion of the tibial plateau and the medial femoral portion of the femoral adjustment member. The lateral force and the medial force are measured with the force sensor. At least one of measuring the lateral force or measuring the medial force comprises transmitting a voltage to a sensor element of a thin force sensing portion of the force sensor and measuring the voltage after it has passed through the sensor element. A percentage of the voltage passed through the sensor element relative to the voltage transmitted to the sensor element is determined. The measured force is derived from the percentage. At least one of the measured lateral force or measured medial force is displayed with a visual display coupled with or integral with the force sensor. In still other embodiments, adjusting the femoral adjustment member comprises adjusting the femoral adjustment member such that the measured lateral force matches the medial force.

In a preferred embodiment of the invention, a system for enhancing a surgical procedure on a knee comprises a femoral adjustment member removably engagable with a cut distal end of a femur. The femoral adjustment member includes a femoral body having a lateral side and a medial side as well as a lateral adjustable member disposed on the lateral side of the femoral body and a medial adjustable member disposed on the medial side of the femoral body. The lateral adjustable member and medial adjustable member are separately adjustable to adjust the position of the femoral body relative to the cut distal end of the femur and to apply tension to at least one of the lateral collateral ligament or the medial collateral ligament of the knee. A coupling mechanism is disposed on the distal end of an intermedullary rod that self-centers the femoral adjustment member when coupled together. The coupling mechanism is not influenced by the intermedullary rod when coupled to the femoral adjustment member. The coupling mechanism self-centers the femoral adjustment in at least a flexion/extension direction and a varus/valgus direction.

In other embodiments, a force sensor is adapted to measure a lateral force exerted between the lateral side of the femoral body and a lateral side of the tibial plateau, and to measure a medial force exerted between the medial side of the femoral body and a medial side of the tibial plateau. A visual display is coupled to the force sensor. The visual display is adapted to display the measured lateral force and the measured medial force.

In other embodiments, the lateral adjustable member and medial adjustable member are selected from the group consisting of screws, pins, levers, rods, springs, spring-loaded mechanisms and shape memory materials.

In other embodiments, a key is engaged with the distally extending portion of the intermedullary rod and adapted to rest atop the outer race of the intermedullary rod to create a balanced plane from which to establish a cutting guide.

BRIEF DESCRIPTION OF THE DRAWINGS

FIGS. 2A-2D show a femoral adjustment member of the system of FIG. 1. FIG. 2A shows a front view of the femoral adjustment member. FIG. 2B shows a back view of the femoral adjustment member. FIG. 2C shows an alternative embodiment of the femoral adjustment member with an anterior ball coupling. FIG. 2D shows an exploded view of the femoral adjustment member.

FIGS. 4A-4H3 show a method of facilitating a surgical procedure on the knee according to embodiments of the invention.

FIGS. 8A-8B show a perspective view of a low profile version including an anterior patellar groove section according to embodiments of the invention.

FIG. 23 shows a side view of the patellar groove section without an augment element.

FIGS. 23A1 and 23B1 show side views similar to FIGS. 23A and 23B, respectively, that include surrounding anatomical structures and devices.

FIGS. 23G-23I show perspective views of the augment element in FIG. 23E.

FIGS. 25A-25B show perspective views of positioning the cutting guide according to embodiments of the invention.

FIG. 26C shows a perspective view of a cutting guide positioned too low to make a nominal clean-up cut on the femoral head according to embodiments of the invention.

DETAILED DESCRIPTION OF THE INVENTION

Figure 1:
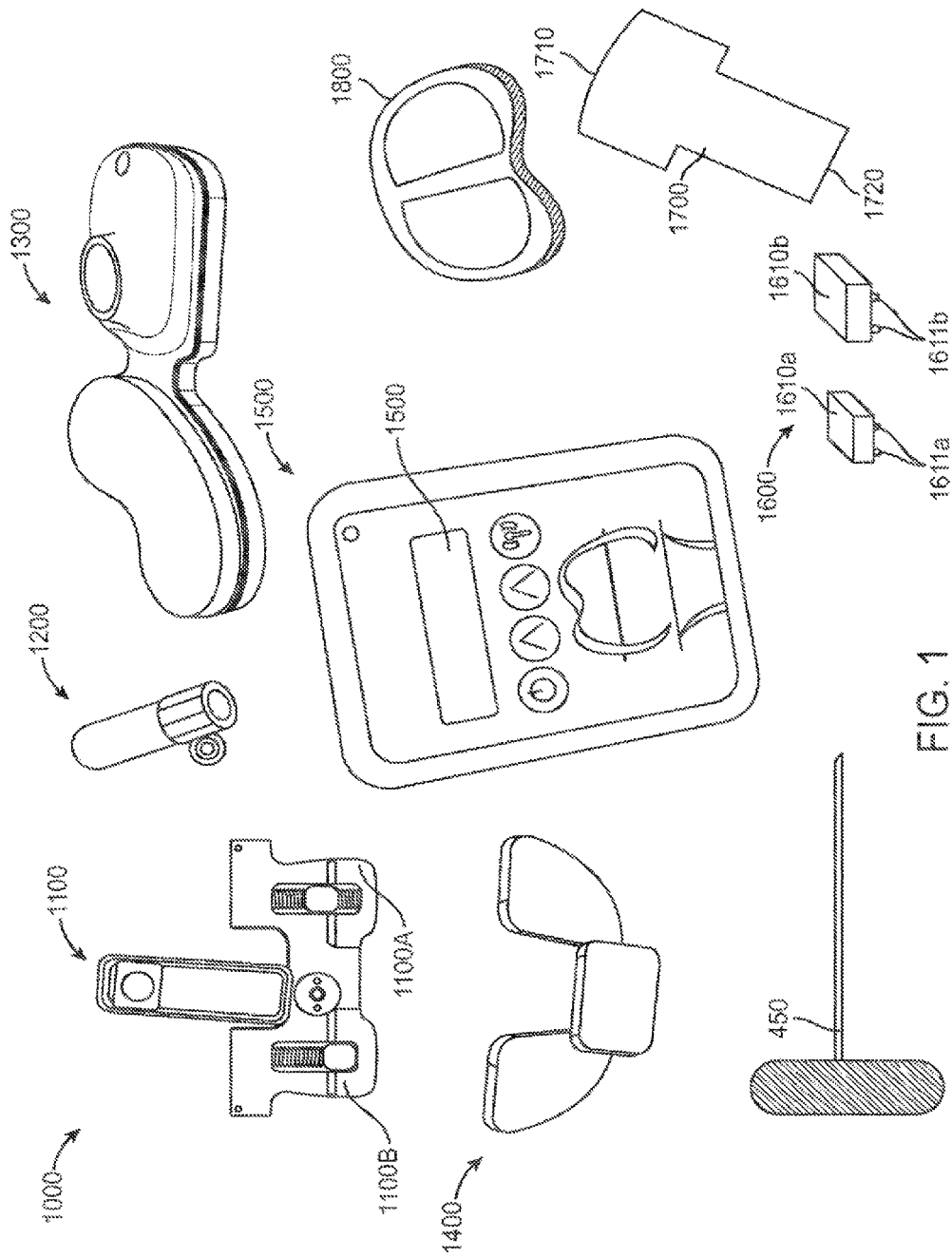
FIG. 1 shows a system for facilitating a surgical procedure on the knee according to embodiments of the invention.

FIG. 1 shows a revision TKA knee balancing system 1000 according to an embodiment of the invention. System 1000 comprises a femoral adjustment member 1100, a locking clamp 1200, a force sensor 1300, a reference cutting guide 1400 and a visual display 1500 comprising a screen 1510. Femoral adjustment member 1100 comprises a lateral first adjustable portion 1100A and a medial second adjustable portion 11008. Knee balancing system 1000 may further comprise a screwing tool 450, femoral adjustment member augmenting members 1600, reference tongue 1700, and tibial tray 1800. Femoral adjustment member posterior augmenting members 1600 may comprise a first augmenting element 1610a having feet 1611a and as second augmenting element 1610b having feet 1611b. Reference tongue 1700 has a distal end 1710 and a proximal end 1720.

Figure 2C:
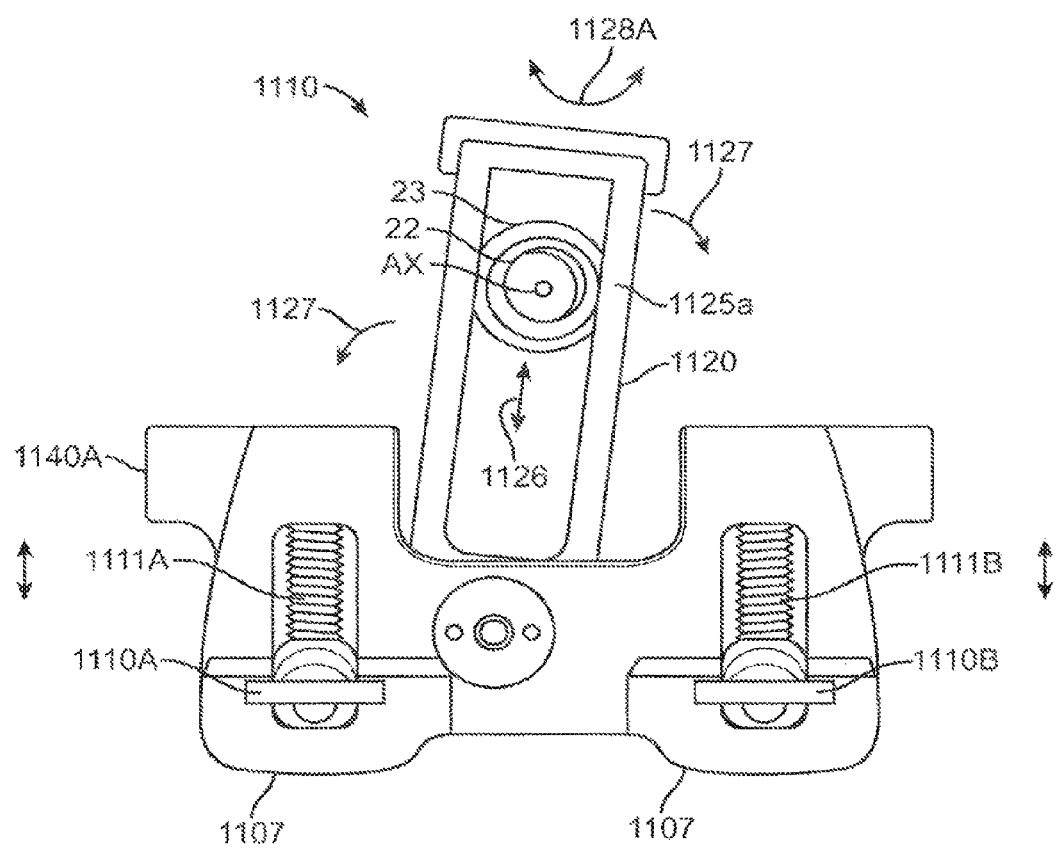

FIGS. 2A-2D show femoral adjustment member 1100 adapted for use with a left knee. It will be apparent to those skilled in the art that similar embodiments of femoral adjustment members may be adapted for use with a right knee. FIGS. 2A and 2B show a front view and a back perspective view, respectively, of femoral adjustment member 1100. Femoral adjustment member 1100 comprises a femoral adjustment member body 1105 having a tibial facing surface 1107. Adjustable lateral portion 1100A comprises a lateral first condylar paddle 1110A coupled to as lateral first paddle screw 1130A. Adjustable medial portion 1100B comprises a medial second condylar paddle 1110B coupled to a medial second lateral screw 1130A. Lateral condylar paddle 1110A and medial condylar paddle 1110B can be rotated and adjusted using screwing tool 450. Lateral first condylar paddle 1110A comprises slots 1112A and medial condylar paddle 1110A comprises slots 1112B. Slots 1112A and 1112B are adapted to couple with feet 1611A and 1611B to adjust the heights of medial condylar paddle 1110A and/or lateral condylar paddle 1110B, respectively. Femoral adjustment member 1100 further comprises a self-centering slider assembly 1120. Slider assembly 1120 comprises a slider frame 1121 and a slider bolt 1125 disposed within slider frame 1121. Slider assembly 1120 is coupled to femoral adjustment member body 1105 toward its medial side or medial second adjustable portion 1100B. Femoral adjustment member 1100 further comprises a lateral first locking screw 1140A and a medial second locking screw 1140B for locking reference cutting guide 1400 in place relative to femoral adjustment member 1100. Lateral locking screw 1140A and medial locking screw 1140B can be rotated and adjusted using screwing tool 450.

FIG. 2C shows a back view of the femoral adjustment member 1100 including a slider bolt 1125*a* with an inner race 22 and an outer race 23 that swivels about axis AX.

Figure 2D:
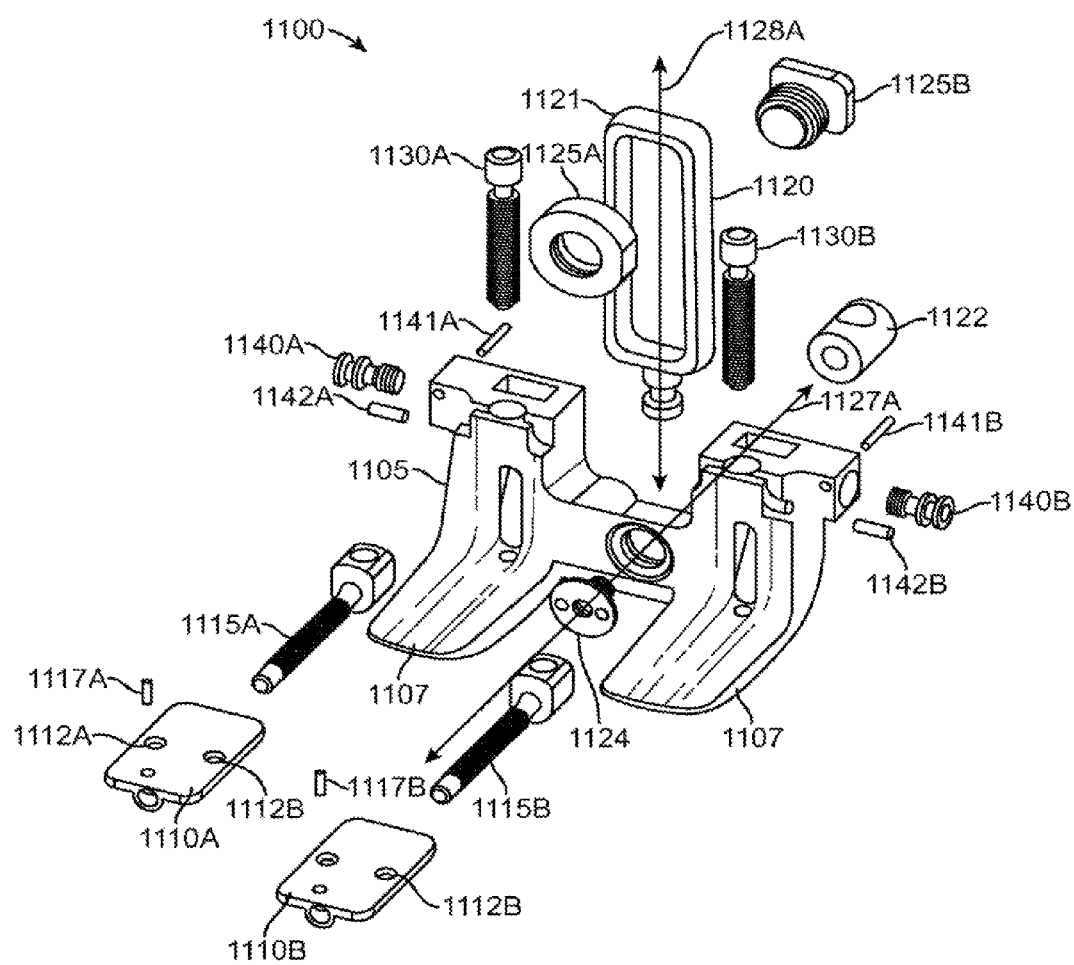

FIG. 2D shows an exploded view of femoral adjustment member 1100. Femoral adjustment member 1100 further comprises a lateral first coupling element 1115A, a medial second coupling element 1115B, a lateral first fastener 1117A, a medial second fastener 1117B, a lateral first paddle screw fastener 1142A, a medial second paddle screw fastener 1142B, a lateral first screw locking fastener 1141A, and a medial second screw locking fastener 1141B. Slider bolt 1125 may comprise a cap 1125A and a bolt 1125B.

Lateral coupling element 1115A can couple lateral condylar paddle 1110A with lateral paddle screw 1130A. Lateral fastener 1117A can couple lateral coupling element 1115A with lateral condylar paddle 1110A. Lateral paddle screw fastener 1142A can couple lateral paddle screw 1130A with femoral adjustment member body 1105. Medial coupling element 1115B can couple medial condylar paddle 1110B with medial paddle screw 1130B. Medial fastener 1117B can couple lateral coupling element 1115B with lateral condylar paddle 1110B. Medial paddle screw fastener 1142B can couple medial paddle screw 1130B with femoral adjustment member body 1105. Lateral screw locking fastener 1141A can couple lateral locking screw 1140A with femoral adjustment member body 1105. Medial screw locking fastener 1141B can couple medial locking screw 1140B with femoral adjustment member body 1105.

Self-centering slider assembly 1120 can be coupled to femoral adjustment member body 1105 with slider holders 1122 and 1124. When a rod, for instance, an intermedullary rod placed into a femur, is threaded into slider bolt 1125, self-centering slider assembly 1120 can center femoral adjustment member body 1105 about the rod and the distal femur. As shown in FIGS. 2B-2D, slider assembly 1120 can have certain degrees of freedom of movement relative to femoral adjustment member body 1105 to perform such self-centering. Slider bolt 1125 can linearly translate within slider frame 1121 in a first direction shown by arrows 1126. Slider frame 1121 can rotate about an axis 1127A defined by slider holders 1122 and 1124 in a second direction shown by curved arrows 1127. Slider frame 1121 can rotate about an axis 1128A orthogonal to both axis 1127A and arrows 1126 in a third direction shown by curved arrows 1128.

Femoral adjustment member 1100 may be adjusted by adjusting the position of at least one of lateral condylar paddle 1110A and medial condylar paddle 1110B relative to femoral adjustment member body 1105. The relative position of lateral condylar paddle 1110A can be adjusted by turning or rotating lateral paddle screw 1130A, for example, with screwing tool 450, which moves paddle 1110A in the directions specified by arrows 1111A. Likewise, the relative position of medial condylar paddle 1110B can be adjusted by turning or rotating medial paddle screw 1130B, for example, with screwing tool 450, which moves paddle 1110B in the directions specified by arrows 1111B. Lateral paddle screw 1130A and medial paddle screw 1130B may be threaded. Alternatively, other arrangements of screws, pins, levers, rods, springs, spring-loaded mechanisms and shape memory materials may be used to adjust femoral adjustment member 1100.

Figure 3A:
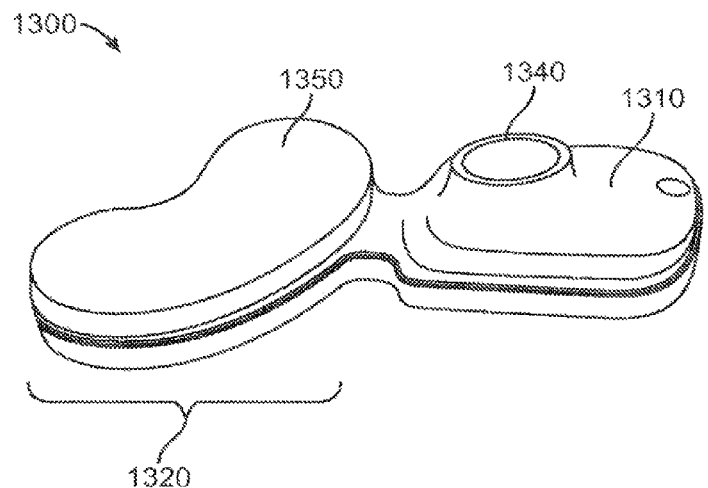
FIG. 3A shows a perspective view of the force sensor of the system in FIG. 1.
Figure 3B:
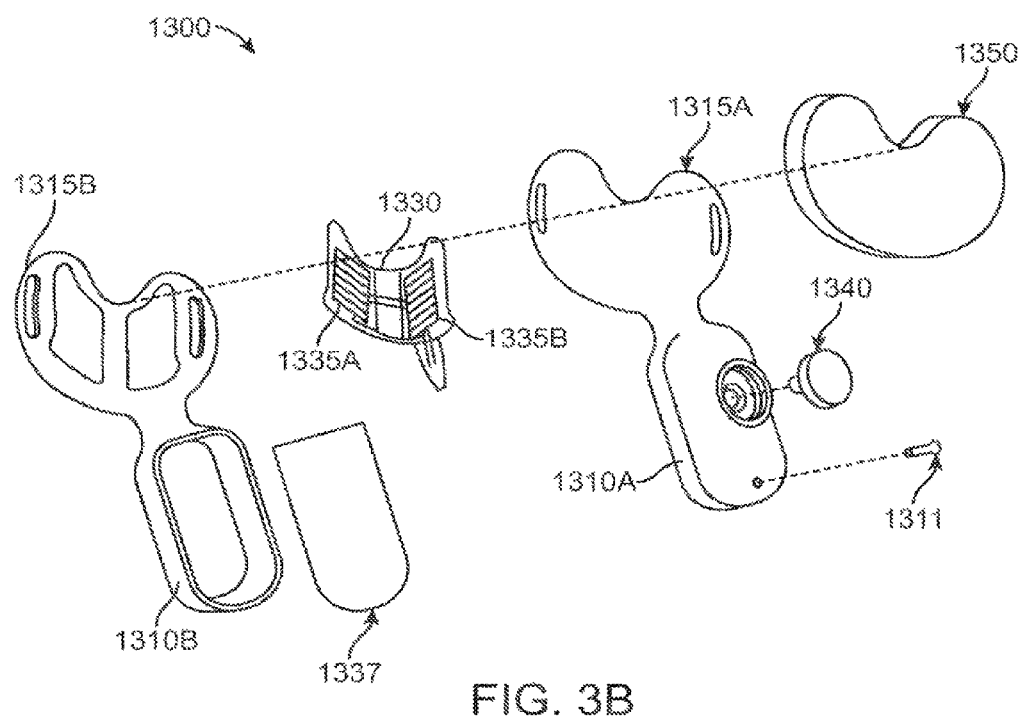
FIG. 3B shows an exploded view of the force sensor of the system in FIG. 1.

FIGS. 3A and 3B show a force sensor 1300. Force sensor 1300 comprises a force sensor body 1310, a force sensing portion 1320, a button or switch 1340, and a pad 1350. FIG. 3B shows an exploded view of force sensor 1300. Force sensor body 1310 comprises a first body portion 1310A and a second body portion 1310B. First body portion 1310A may be coupled to second body portion 1310B with body fastener 1311. First body portion 1310A comprises a first force sensing surface 1315A. Second body portion 1310B comprises a second force sensing surface 1315B. A force sensing element 1330 is disposed between first three sensing surface 1315A and second force sensing surface 1315B. Force sensing element 1330 may comprise a first three sensing region 1335A and a second three sensing region 1335B. Force sensing element 1330 is coupled to processor 1337. Force sensing element 1330 can sense force or pressure thereon and may send signals indicative of measured force or pressure to processor 1337. Processor 1337 may receive these signals and may process them into usable data for display on visual display 1500.

Force sensing element 1330 may compose a layer of pressure or force sensing material. Any suitable pressure or force sensing material or combination of materials may be used to form force sensing element 1330. Some examples that may be used include, but are not limited to piezoelectric sensors, force sensing resistors, force sensing capacitors, strain gauges, load cells, other pressure sensors and other force sensors.

Force sensing element 1330 may comprise any of a number of suitable pressure and/or three sensors. In an exemplary embodiment, processor 1337 transmits a known voltage to force sensing element 1330, the voltage or current out of force sensing element 1330 is measured by processor 1337, and processor 1337 calculates a percentage of the voltage leaving force sensing element 1330 to the known voltage. From this percentage, pressure and/or force can be calculated. Processor 1337 may convert an analog signal representing the pressure and/or force into a digital signal with an analog-to-digital (A/D) convertor, and the A/D converter can provide the digital signal to a look-up table that determines a display value (or values) representing the pressure and or force. The processor 1337 of force sensing element 1300 may be coupled to the display 1500 through any one of a variety of wired or wireless connections, for example. As shown in FIG. 1, the sensor 1300 and display 1500 can be separate devices connected via wireless interface, for example. In an alternative embodiment, depicted in FIGS. 18-22 and 24, the sensor 1300*b* and display 1500*b* can be combined together into a single device and packaged sterile for single use.

A user may use the display value as an absolute number on display 1500 (or 1500*b*). Display may comprise for example, an LCD or LED display. The A/D converter, as well as any additional processing modules for processing sensed data into usable data may all be housed in as single processor such as processor 1337. Alternative methods for sensing and displaying sensed data are also contemplated.

Figure 4A:
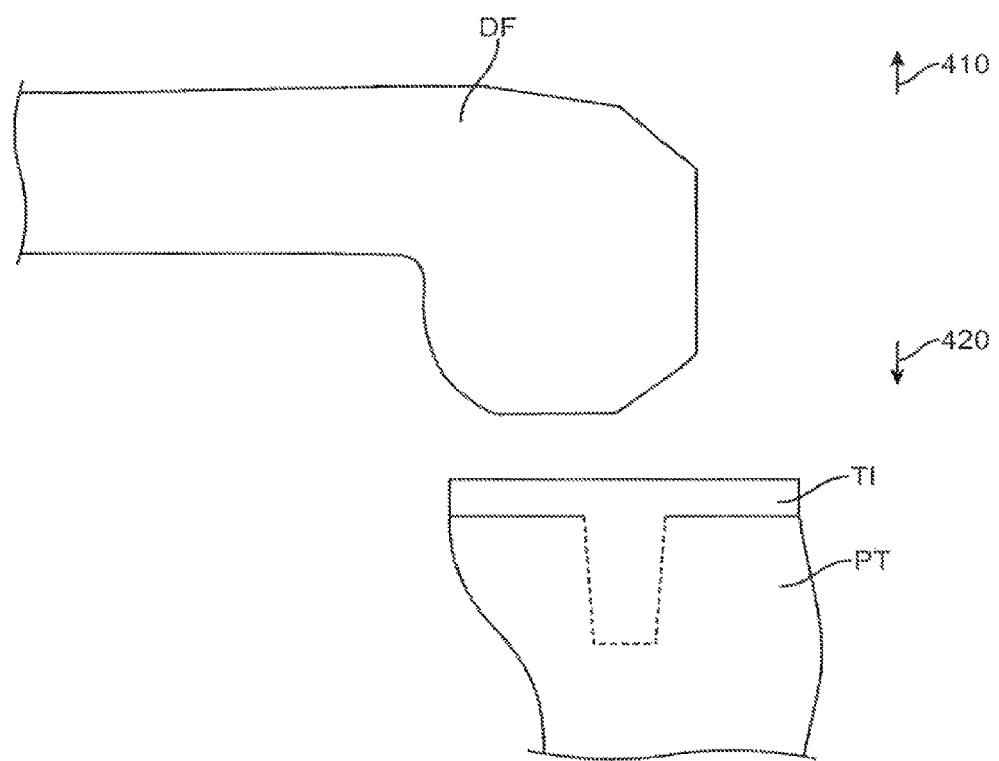

FIGS. 4A-4H3 show a method of facilitating a revision TKA procedure on the knee with system 1100 according to embodiments of the invention. Revision TKA procedures involve removing components of an old or existing artificial knee joint, the reshaping of the end of the distal femur and proximal tibia, and the implantation of new or replacement components. The old femoral component of the existing artificial knee joint is removed using, for example, thin saw blades and osteotomes. For example, a thin saw blade such as those described in co-pending and recently allowed U.S. patent application Ser. No. 11/234,754, Patent Application Publication No. US-2007-0083209-A1, the entirety of which is incorporated herein by reference, may be used to break the interface between the old femoral component and bone. The old tibial component is similarly removed. The proximal tibia can be reshaped or recut, and the tibial intermedullary canal can be reamed. Typically, the replacement tibial component is first implanted and secured on the proximal tibia so that most if not all of the adjustments to knee ligament tension during the surgical procedure need only be made on the femoral side of the knee joint.

System 1000 can find use far steps of the revision TKA procedure involving the femoral side of the knee joint. FIG. 4A shows a knee joint in approximately 90° of flexion during the revision TKA procedure after a new tibial component TI has been implanted on the proximal tibia PT. Tibial component TI may completely cover the tibial plateau of the proximal tibia PT and has a lateral portion and a medial portion. Alternatively, a tibial tray 1800 may be temporarily placed over the tibial plateau of the proximal tibia PT or the tibial plateau of the proximal tibia PT may be left uncovered before tibial component TI is permanently installed. The old femoral component has been removed from the distal femur DF. Distal femur DF has preexisting cuts to its distal end and condylar ends from the original TKA procedure. Anterior arrow 410 defines the anterior direction and posterior arrow 420 defines the posterior direction. As shown in FIG. 4B, the femoral intermedullary canal of the distal femur DF is reamed and broached with a intermedullary rod 400.

Figure 4C:
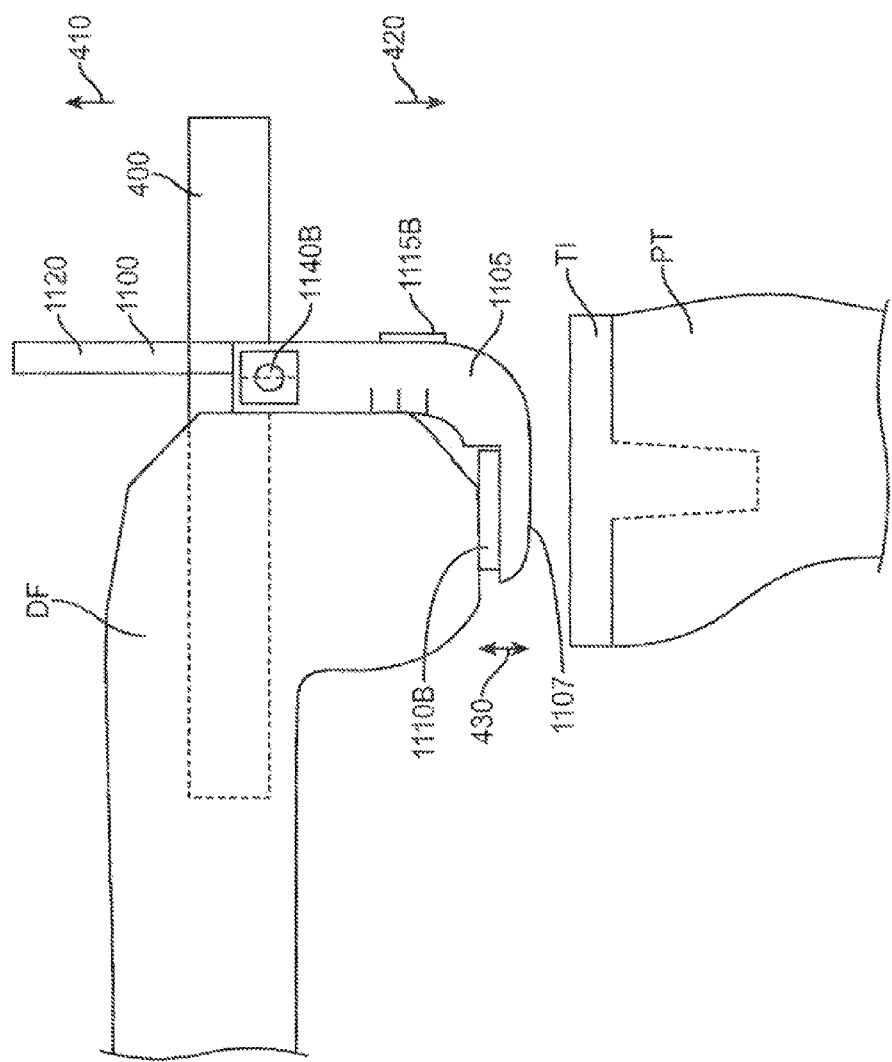

As shown in FIG. 4C, femoral adjustment member 1100 can be slid over intermedullary rod 400 through slider bolt 1125 of slider assembly 1120 to couple with the end of distal femur DF. As previously described, slider assembly 1120 can center femoral adjustment member 1100 about intermedullary rod 400. The femur may be rotated with the medial adjustable portion 1100B as the fulcrum. The femur facing side of femoral adjustment member 1100 may compliment the shape of the distal end and the condylar portion of distal femur DF. Tibial facing surface 1107 of femoral adjustment member 1100 faces the surface of tibial component TI. Lateral condylar paddle 1110A and medial condylar paddle 1110B are respectively engaged against the cut ends of the lateral condyle and medial condyle of distal femur DF. The positions of lateral condylar paddle 1110A and medial condylar paddle 1110B may be adjusted relative to femoral adjustment member body 1105 in a directions indicated by arrows 430. Femoral adjustment posterior augmenting members 1600 may be coupled to lateral condylar paddle 1110A and/or medial condylar paddle 1110B to increase the thickness of lateral condylar paddle 1110A and/or medial condylar paddle 1110B.

Figure 4D:
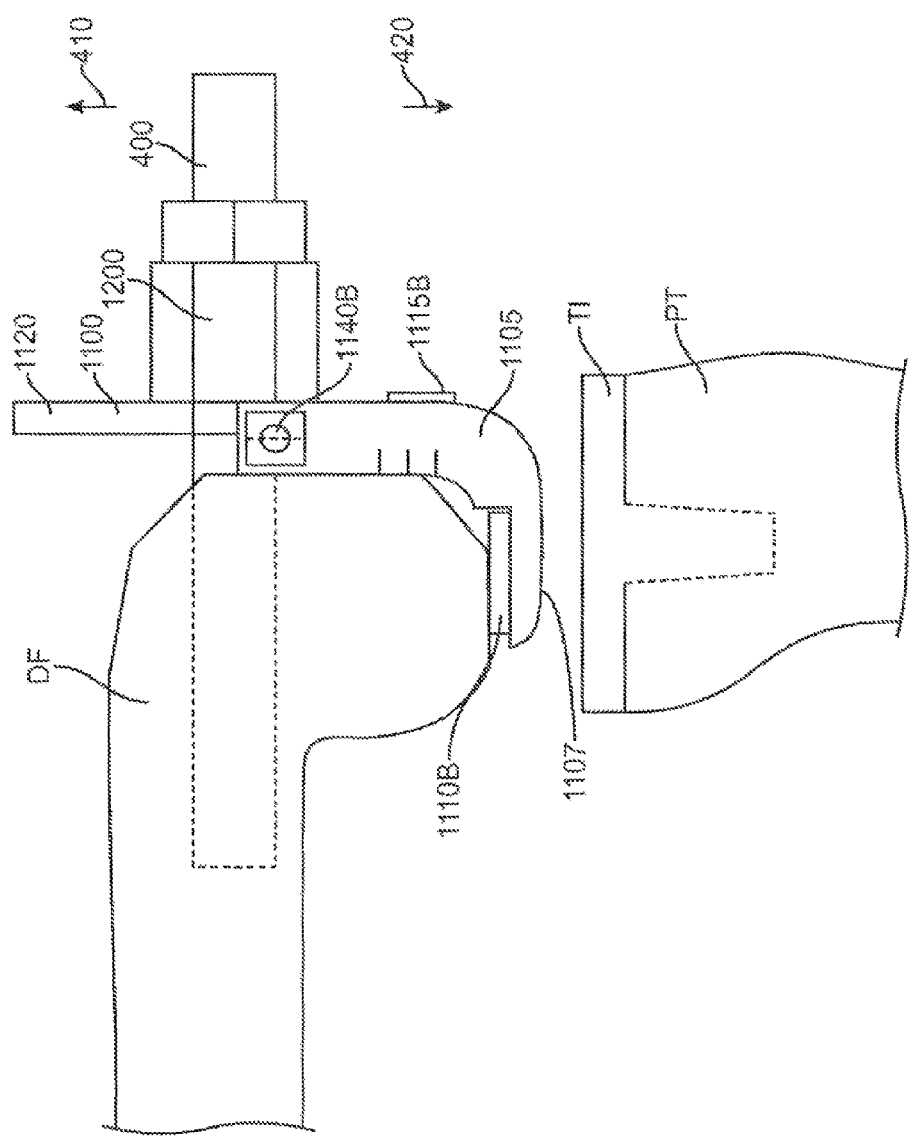

As shown in FIG. 4D, once femoral adjustment member 1100 is engaged against the distal femur DF, locking clamp 1200 can be slid over intermedullary rod 400 and engaged with femoral adjustment member 1100 to lock and secure femoral adjustment member 1100. FIGS. 4D1 and 4D2-4D4 respectively show locking clamp 1200 in a perspective view and a front view. Locking clamp 1200 has a central lumen 1225 and comprises a clamping mechanism 1240 coupled to a locking clamp main body 1210. Locking clamp 1200 can be slid over intermedullary rod 400 through central lumen 1225. Clamping mechanism 1230 comprises a screw 1227 which can be turned, for example, with screwing tool 450, to tighten or loosen clamping mechanism 1230. Clamping mechanism 1230 is disposed partially within clamp main body 1210, which as shown is triangular. However, in other embodiments, clamp main body 1210 may have any number of sides. Triangular main body 1210 can rotate about clamping mechanism 1230 to adjust which sides of main body 1210 face anteriorly or posteriorly. As shown in FIG. 4D2, central lumen 1225 is offset from the center of triangular main body 1210. Because of this offset, triangular main body 1210 comprises a neutral side 1230, a negative side 1233 and a positive side 1236. As shown in FIG. 4D2, triangular main body 1210 may be placed in a first position in which neutral side 1230 faces anteriorly while negative side 1233 and positive side 1236 face posteriorly. As shown in FIG. 4D3, triangular main body 1210 may be placed in a second position in which negative side 1233 faces anteriorly while, neutral side 1230 and positive side 1236 face posteriorly. As shown in FIG. 404, triangular main body 1210 may be placed in a third position in which positive side 1236 faces anteriorly while neutral side 1230 and negative side 1233 face posteriorly. Depending on which one of these sides faces the anterior direction, the anterior face of triangular main body 1210 may be higher or lower relative to intermedullary rod 400 and femoral adjustment body. The second position is lower than the first position which is lower than the third position. For example, main body 1210 may be shaped so that the second position may be 1, 2 or 3 mm lower than the first position which may be 1, 2 or 3 mm lower than the third position.

Figure 5:
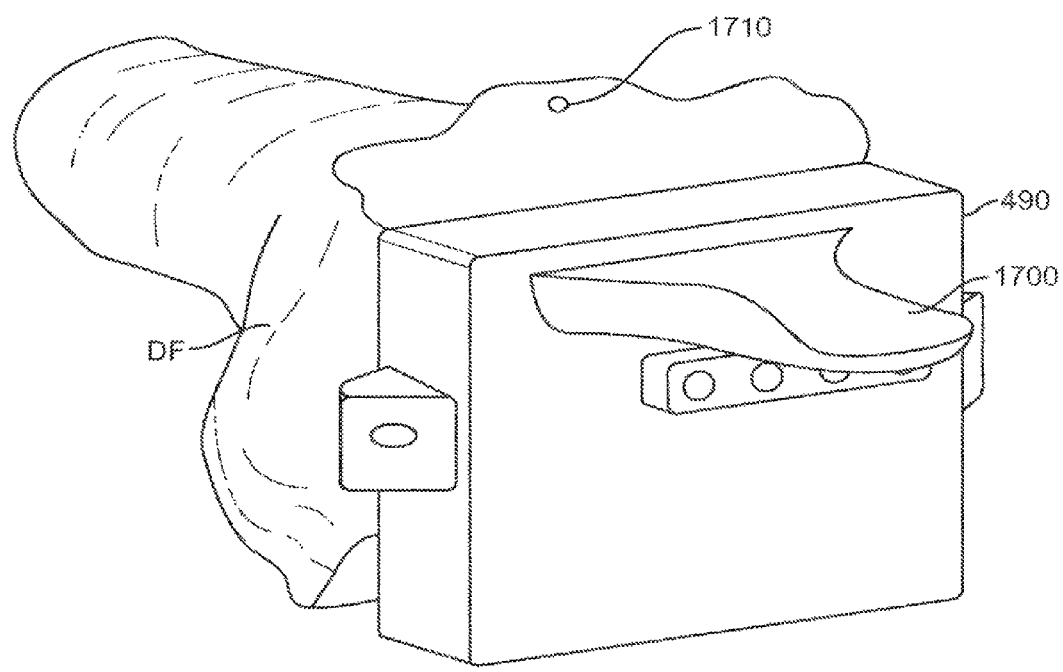
FIG. 5 shows a method of facilitating a clean-up cut on the knee according to embodiments of the invention.
Figure 6:
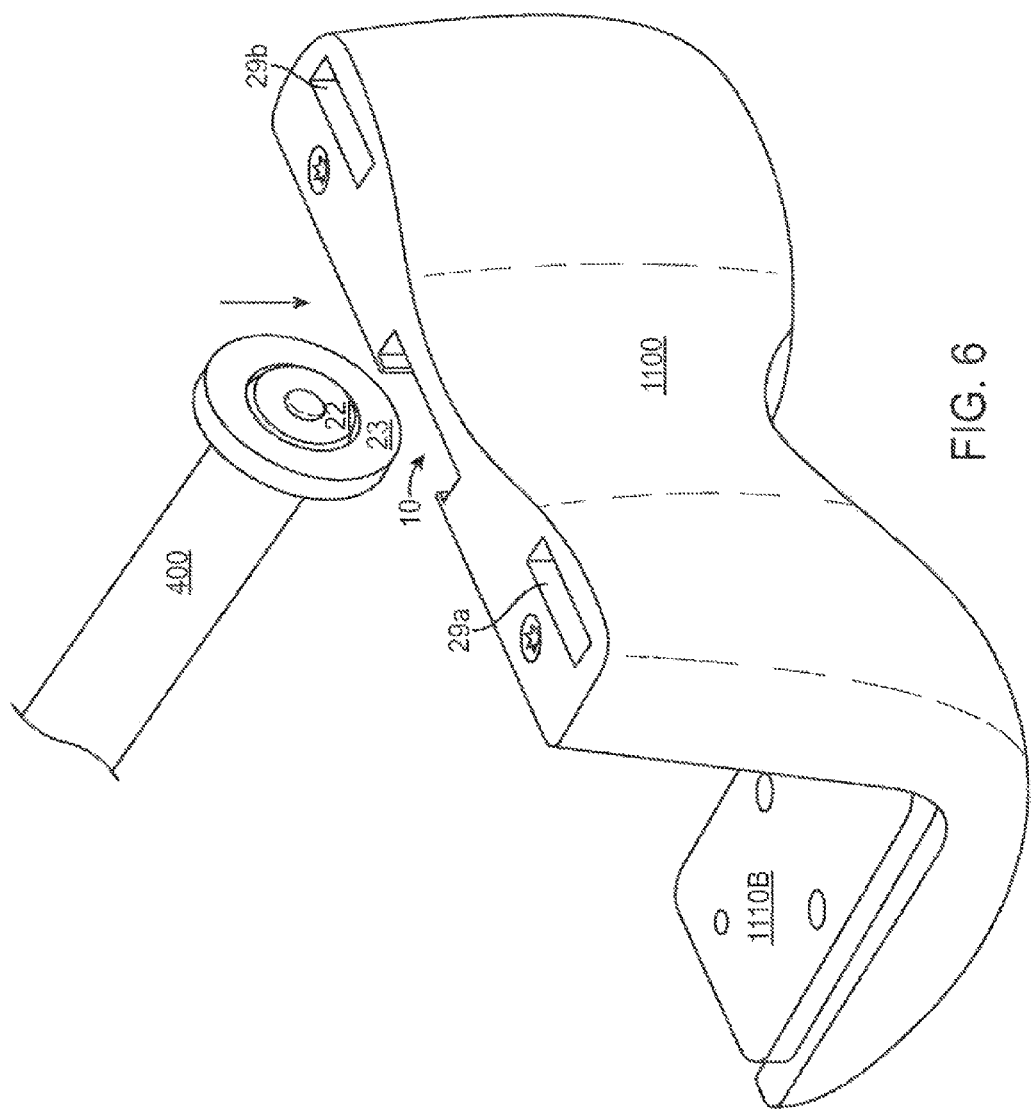
FIG. 6 shows a perspective view of a low profile version according to embodiments of the invention.
Figure 7:
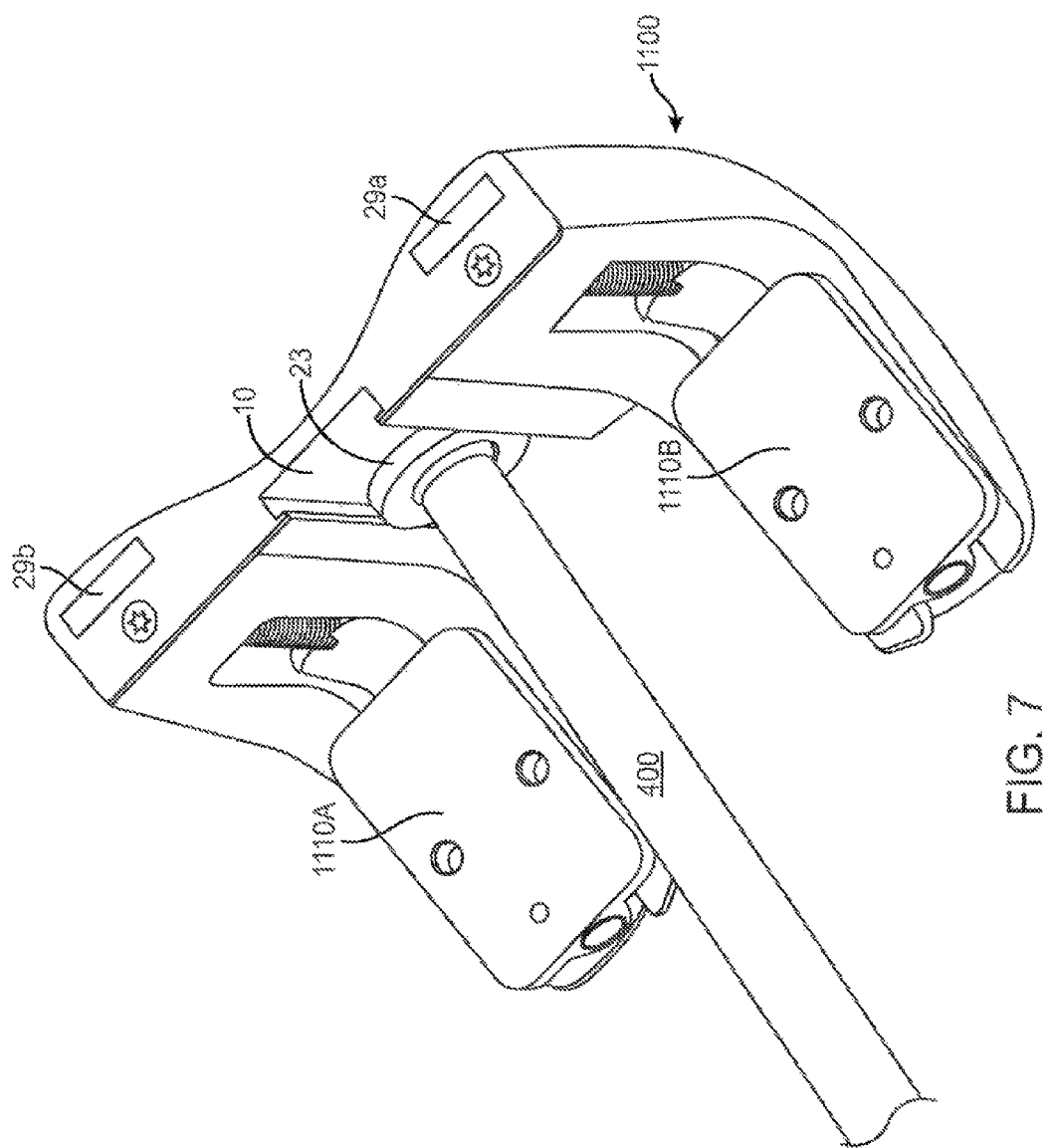
FIG. 7 shows a perspective view of a low profile version according to embodiments of the invention.

As discussed above, a locking clamp may have any number of sides, for example 5, 6, 7, 8 or more sides. FIGS. 4D5 and 4D6 show a locking clamp 1201 having 5 sides in a perspective view and a front view, respectively. Locking clamp 1201 has a central lumen 1226 and comprises a clamping mechanism 1241 coupled to a locking clamp main body 1211. Main body 1211 can rotate about clamping mechanism 1231 to adjust which sides of main body 1211 face anteriorly or posteriorly. Main body has a first side 1260, a second side 1262, a third side 1264, a fourth side 1258, and a fifth side 1257. Second side 1262 may be 2 mm higher than first side 1260 when facing anteriorly. Third side 1264 may be 4 mm higher than first side 1260 when facing anteriorly. Fourth side 1258 may be 2 mm lower than first side 1260 when facing anteriorly. Fifth side 1258 may be 2 mm lower than first side 1260 when facing anteriorly.

Figure 4E:
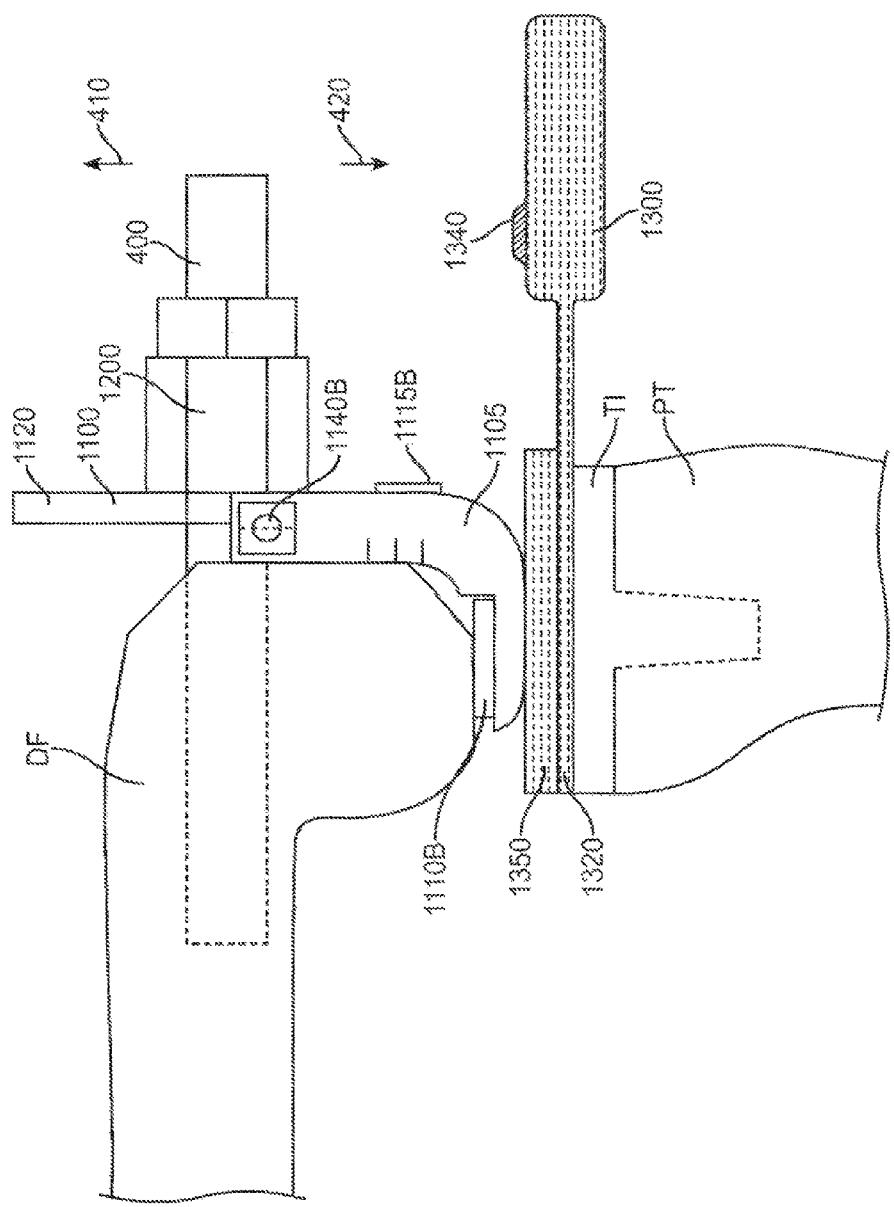
Figure 4F:
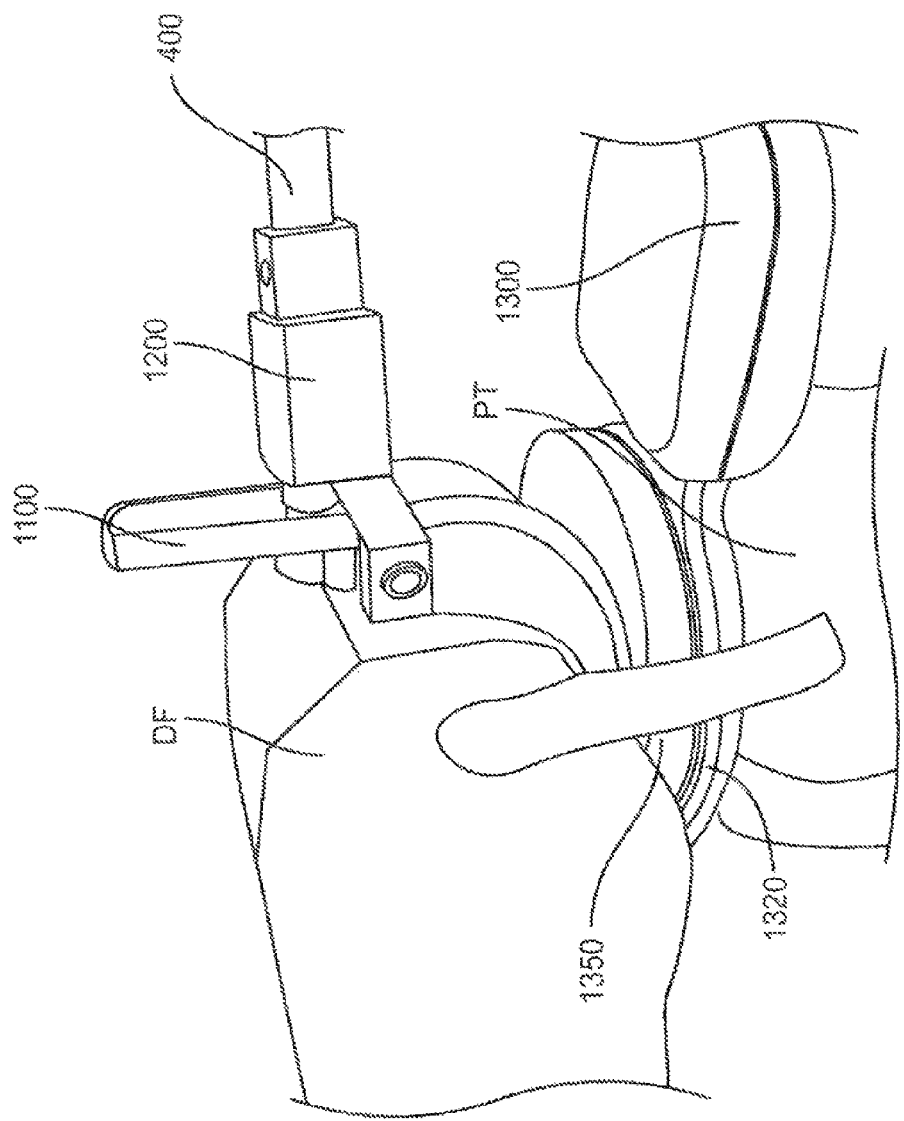

As shown in FIGS. 4E and 4F, force sensing portion 1320 and pad 1350 of force sensor 1300 may then be placed between femoral adjustment member 1100 and tibial component TI. In alternative procedures, force sensing portion 1320 and pad 1350 of force sensor 1300 may be placed between the tibial component TI and the tibial plateau, between femoral adjustment member 1100 and tibial tray

1800, between tibial tray 1800 and the tibial plateau, or between femoral adjustment member 1100 and the tibial plateau. In other alternative procedures, force sensor 1300 may not be used at all and femoral adjustment member 1100 may be based on the manual "feel" of a surgeon. Force sensor 1300 can sense and measure the distal and medial force exerted between the femoral adjustment member 1100 and tibial component TI. The distal and medial forces are cause by tension in the ligaments of the knee, particularly the lateral collateral ligament and medial collateral ligament. Visual display 1500 can then display the measured lateral and medial forces. Femoral adjustment member 1100 can then be adjusted based on the measured lateral and medial forces and/or pressures. For example, if the measured medial and lateral forces are not equal, the position at least one of the lateral condylar paddle 1110A and the medial condylar paddle 1110B may be adjusted so that the measured medial and lateral forces are matched and tension in the knee ligaments is balanced. For example, as shown in FIGS. 4G1-4G3, the position of lateral condylar paddle 1110A may be adjusted by coupling lateral paddle screw 1130A with screwing tool 450 and then turning or rotating screwing tool 450 along with lateral paddle screw 1130A in a rotation 460. The position of medial condylar paddle 1110B can likewise be adjusted in the same manner. Adjusting the position of one of lateral condylar paddle 1110A and medial condylar paddle 1110B while the position of the other condylar paddle is fixed can rotate femoral adjustment member 1100 about the distal femur DF. FIG. 4G1 shows locking clamp 1200 in the first position in which neutral side 1230 faces the anterior direction 410. FIG. 4G2 shows locking clamp 1200 in the second position in which negative side 1233 faces the anterior direction 410. FIG. 4G3 shows locking damp 1200 in the third position in which positive side 1236 faces the posterior direction 410. Locking clamp 1200 may be switched between any of these three positions without the need to reconfigure or reposition any component of femoral adjustment member 1100 and intermedullary rod 400.

As shown in FIGS. 4H1-4H3, after the femoral adjustment member 1100 has been adjusted as described above, reference cutting guide 1400 can be engaged with femoral adjustment member 1100, for example, by being slid into femoral adjustment member body 1105. The posterior side of reference cutting guide 1400 abuts the anterior face of locking clamp 1200. Depending on which of neutral side 1230, negative side 1233, and positive side 1236 of locking clamp 1200 faces anteriorly, reference cutting guide 1400 can be positioned either higher or lower. As shown in FIG. 4H1, locking clamp 1200 is in the first position and neutral side 1230 faces anteriorly. As shown in FIG. 4H2, locking clamp 1200 is in the second position and negative side 1233 faces anteriorly. Reference cutting guide 1400 is relatively lower when locking clamp 1200 is in the second position than when locking clamp 1200 is in the first position. As shown in FIG. 4H3, locking clamp 1200 is in the third position and positive side 1236 faces anteriorly. Reference cutting guide 1400 is relatively higher when locking clamp 1200 is in the third position than when locking clamp 1200 is in the first position. Reference cutting guide 1400 can be secured in place relative to femoral adjustment member 1100 by screwing in lateral locking screw 1140A and or medial locking screw 1140B with screwing tool 450. After removing force sensor 1300, a first series of cuts, for example, an anterior clean-up cut, can then be made on the distal femur DF, for example, with the anterior side 1420 of reference cutting guide 1400 as a reference. Anterior clean-up cuts may be made to correct cuts previously made to the anterior side of the distal femur in a previous knee replacement surgery procedure. A plurality of reference cutting guides 1400 may be provided, each having a different anterior-posterior height and/or slope, which may be used based on the dimensions of as patient's distal femur.

Reference cutting guide 1400, locking clamp 1200, femoral adjustment member 1100 and intermedullary rod 400 can then be disengaged and removed from distal femur DF. A surgical cutting guide 490 can then be positioned and secured on the distal femur DF based on the prior cuts made with reference cutting guide 1400 as a guide. For example, as shown in FIG. 5, distal side 1710 of reference tongue 1700 may be placed on an anterior clean-up cut, and reference cutting guide 1400 can be slid over reference tongue 1700 to position guide 1400 on the distal femur. Alternatively, reference cutting guide 1400 may comprise a tabbed section or bill which can be used to position reference cutting guide on an anterior cleanup guide. A second series of cuts, for example, comprising anterior cuts and/or posterior cuts, can then be made on the distal femur DF using surgical cutting guide 490 as a reference guide. Surgical cutting guide 490 can then be disengaged and the cut end of the distal femur DF can be fit with a replacement femoral component. The femoral component of the prosthetic knee joint may be positioned on the distal femur DF based on the cuts made with cutting guides 1400 and 490 as guides. Thus, the femoral component can be implanted and positioned such that knee ligament tension is well balanced.

Figure 8C:
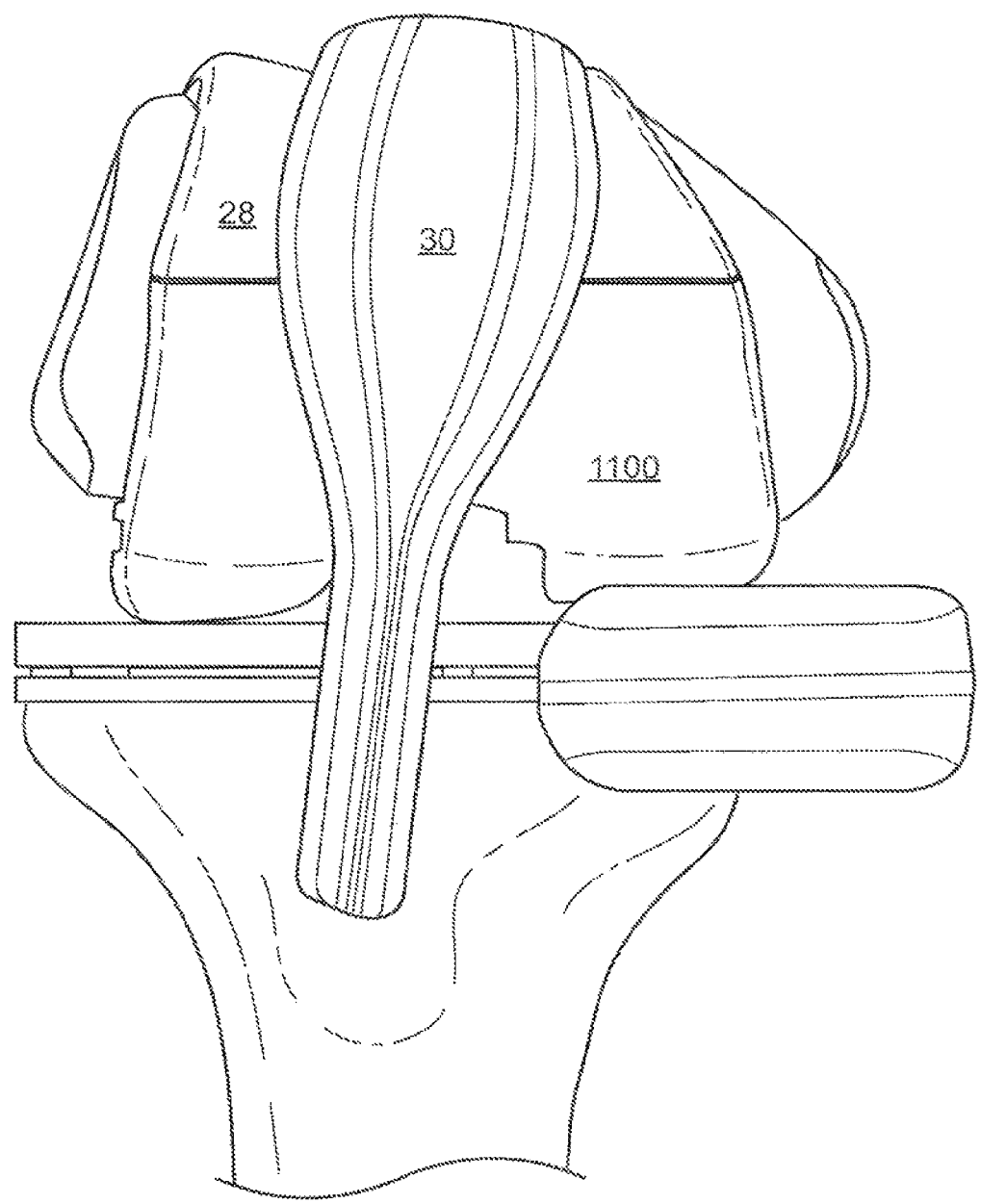
FIG. 8C shows a shows a top view of a knee joint in extension with the patella reduced according to embodiments of the invention.

Beginning with FIG. 6, an preferred embodiment of the invention, including a low profile intermedullary rod 400, is shown. Unlike FIGS. 4B to 4H3, a low profile intermedullary IM rod allows for reducing the patella because there is no hardware, like locking clamp 1200 in FIG. 4F, for example, protruding from the femoral member 1100. This allows the femoral member to be adjusted with full range of patella tracking. FIG. 6 shows a perspective view of the intermedullary rod 400 with the femoral adjustment member 1100 lined up underneath. The low profile intermedullary rod includes an outer race 23 and an inner race 22 on the end of the rod that protrudes from the distal femur. In this embodiment, the rod does not extend posteriorly past the femoral member 1100. The outer race 23 slides into the T slot 10 as seen from an anterior position looking toward the posterior in FIG. 7. The outer race 23 swivels or pivots about the inner race 22. As shown in FIG. 8A (and also in FIG. 18), the tangs 31a and 31b of the anterior patellar groove section 28 can slip into the femoral adjustment member 1100 through openings 29a and 29b, respectively. FIG. 8B shows the patellar groove section 28 in place with the trochlear groove 45 established between section 28 and femoral adjustment member 1100. FIG. 8C shows a front view of the knee joint in extension. The patella is reduced and the patella tendon 30 has been moved into place. FIGS. 6-8C provide a general overview of the low profile embodiment. Additional details now follow.

Figure 9:
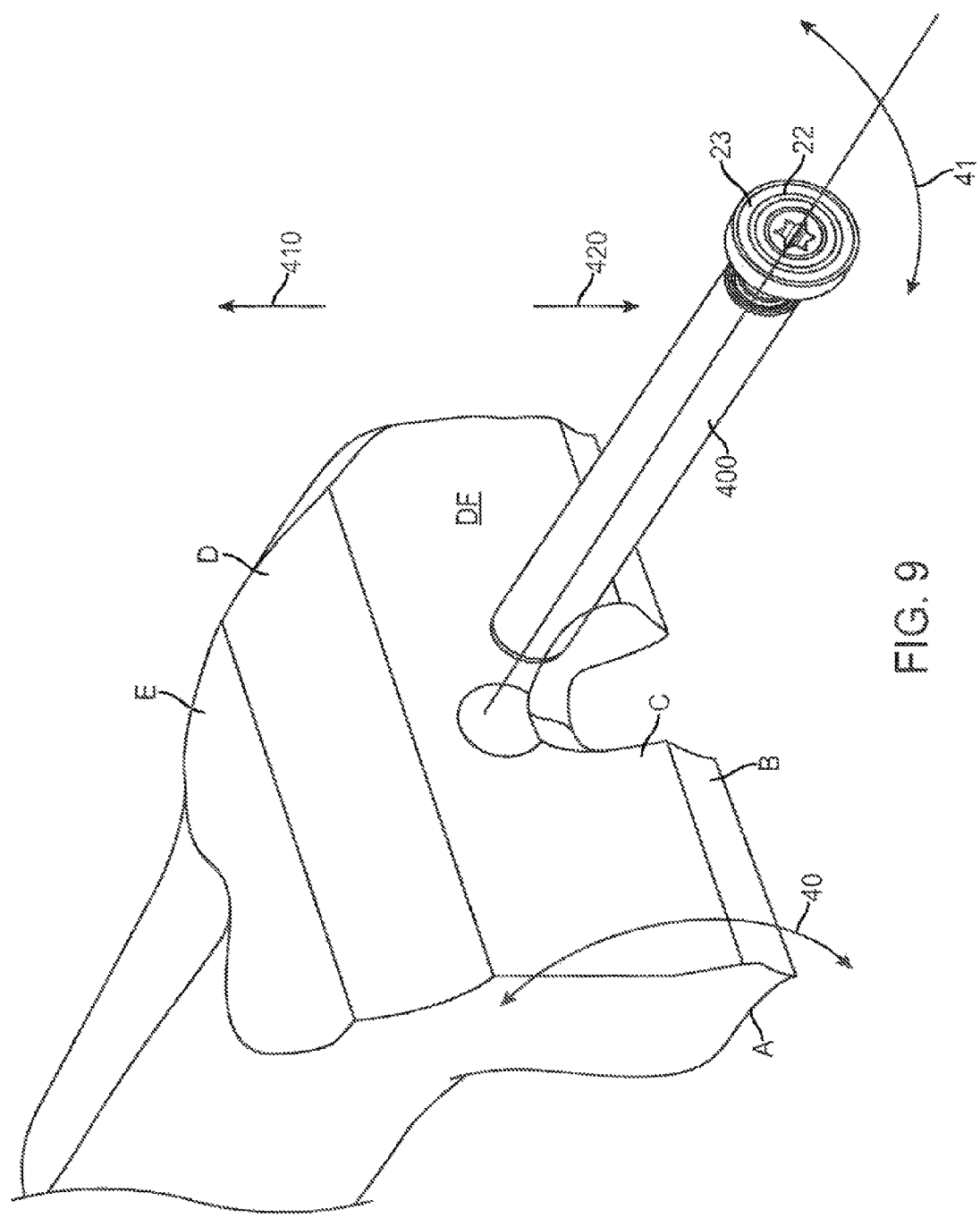
FIG. 9 shows a perspective view of a distal femur with five completed cuts.

FIG. 9 shows a distal femur DF with five completed cut surfaces A-E. Directional arrow 410 is anterior and directional arrow 420 is posterior. The distal femoral surface is perpendicular to the long axis of the femur and is typically at a valgus angle of about six degrees from the anatomical axis of the femur. Directional arrow 40 indicates the flexion/extension axes (i.e the axes that the tibia, articulates about the femur). The femur is fundamentally stationary with the exception of the movement in the hip. The intermedullary rod 400 is an axis centerline going through the centerline in the intermedullary (IM) canal. Varus/valgus movement is along direction 41.

Figure 10:
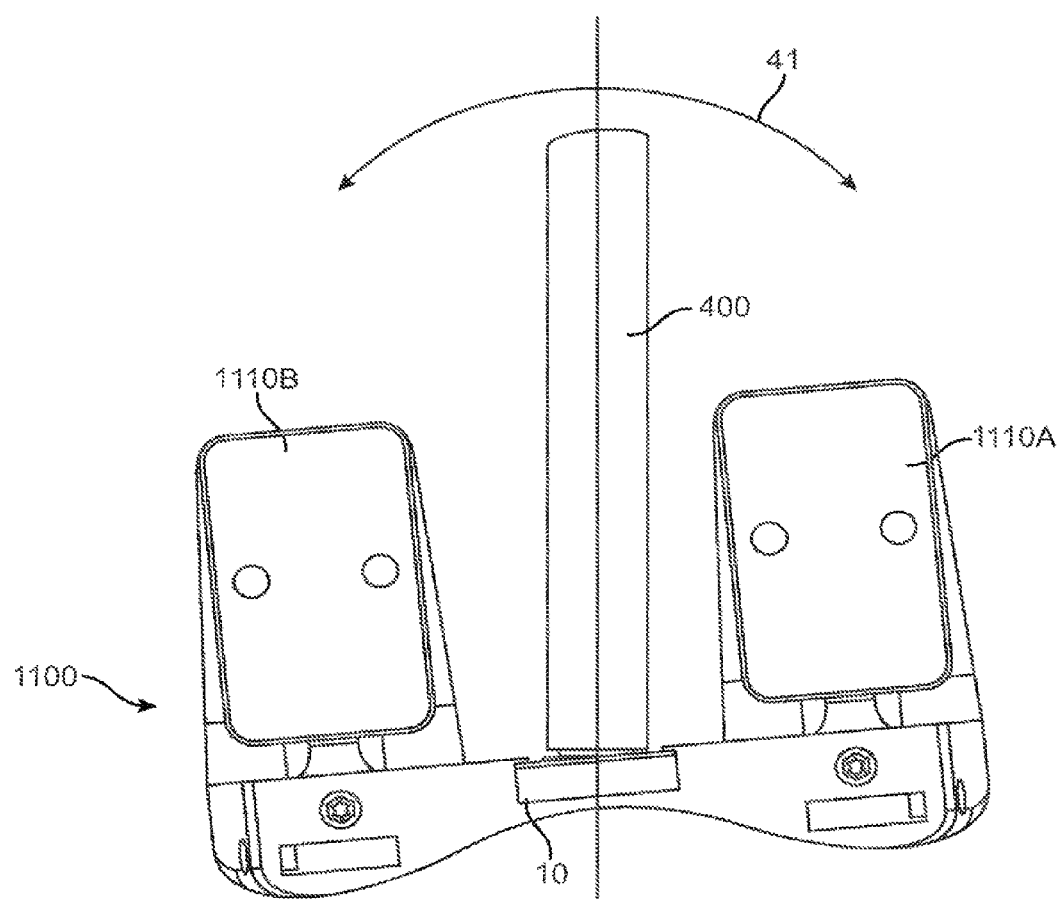
FIG. 10 shows a top view of the intermedullary rod attached to the femoral adjustment component.

FIG. 10 shows a top view of the intermedullary rod 400 with several components attached. The same varus/valgus direction 41 as previously shown in FIG. 9 is now shown with the ball-shaped coupling, including races 22 and 23, attached where the intermedullary rod 400 connects to the femoral adjustment member 1100. The intermedullary rod 400 connects to the femoral adjustment member 1100 by sliding into T slot 10.

Figure 11:
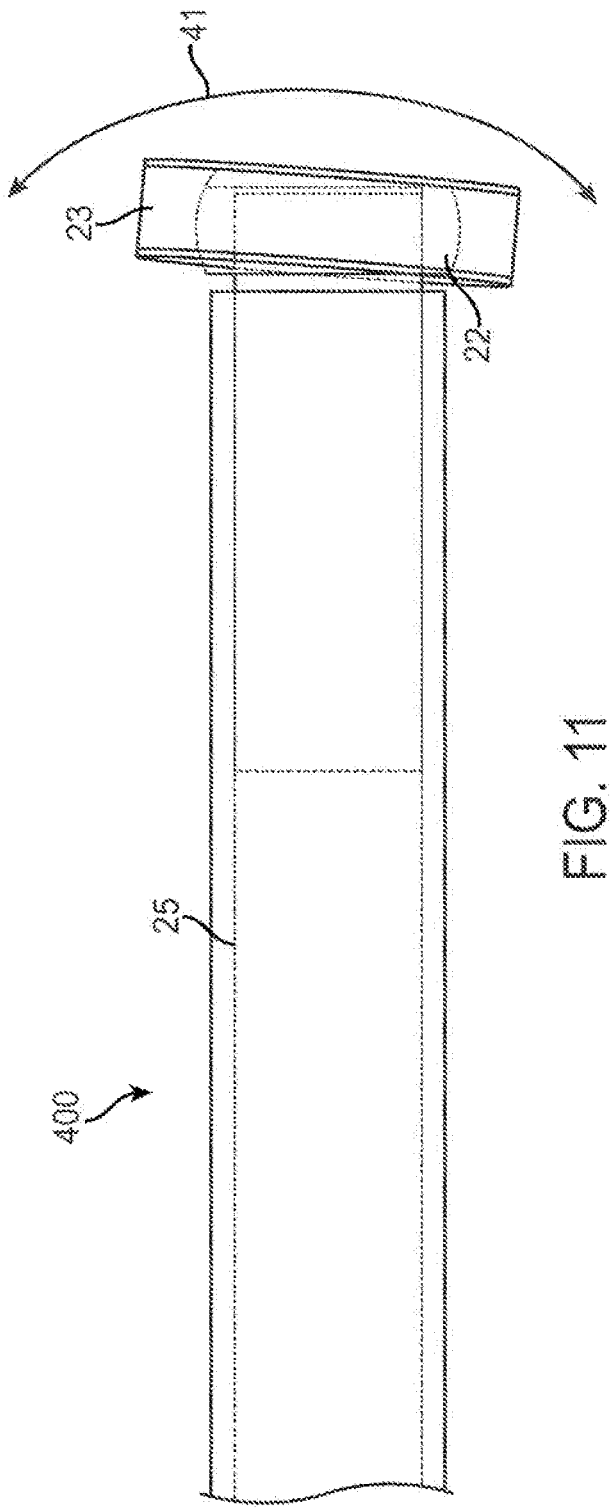
FIG. 11 shows a top view of the intermedullary rod with movement in the varus/valgus direction.

FIG. 11 shows a top view of the intermedullary rod 400 as viewed from an anterior vantage with movement in the varus/valgus direction 41. Internal telescoping mechanism 25 and rotating race 23 are also shown. The dotted lines of the couplings depict an inner race 22 of the ball coupling. The outer race 23 slides into the T slot 10 of the femoral component of the femoral adjustment member 1100 (not shown in FIG. 11). The inner race 22 is a portion of a ball so that the outer race 23 can rotate 360 degrees about the inner race in a varus/valgus direction and pivots approximately 12 degrees on each side. This serves as a passive self-centering, self-locating mechanism coming off of the cut distal surface at a valgus angle to the intermedullary canal. It is assumed that the valgus angle is within approximately plus or minus five degrees of nominal. The solid line on the outside of the intermedullary rod 400 would be the part of the rod in the femur (not shown in FIG. 11). The dotted line represents a telescoping mechanism 25 that allows expansion away from the distal femur. The telescoping mechanism 25 may be a spring-loaded member, a hydraulically driven member, or any one of various other members that allow for telescopic extension, for example.

Figure 12:
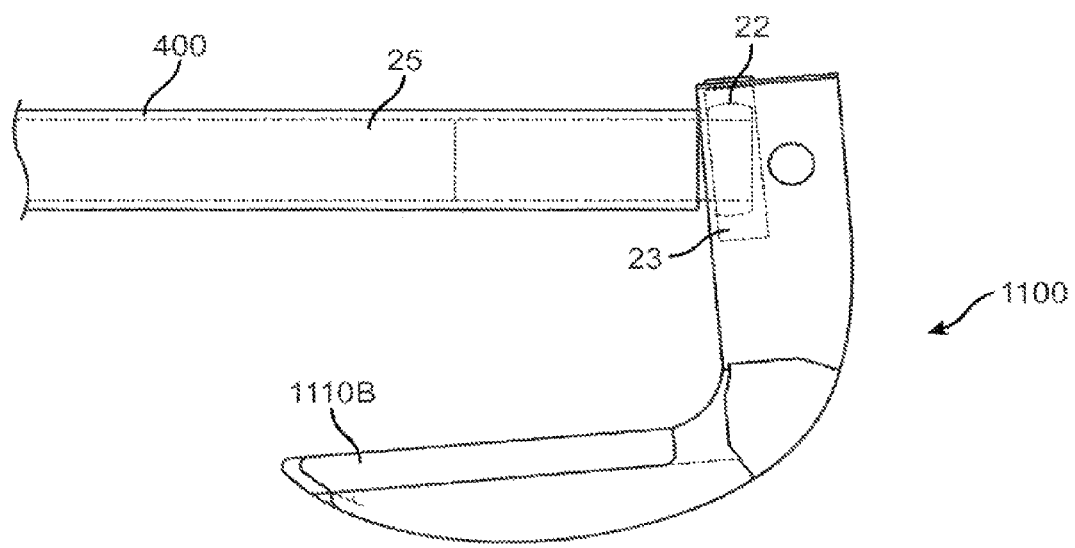
FIG. 12 shows a side view of the femoral adjustment member coupled to the anterior ball of the intermedullary rod.

FIG. 12 shows a side view of the femoral component, including races 22 and 23 on the end of the intermedullary rod 400, slipped into the T-slot 10 of the femoral adjustment member 1100. The inner race 22 and outer race 23 of the ball coupling of the distal end of the intermedullary rod 400 are identified with dotted lines.

Figure 13A:
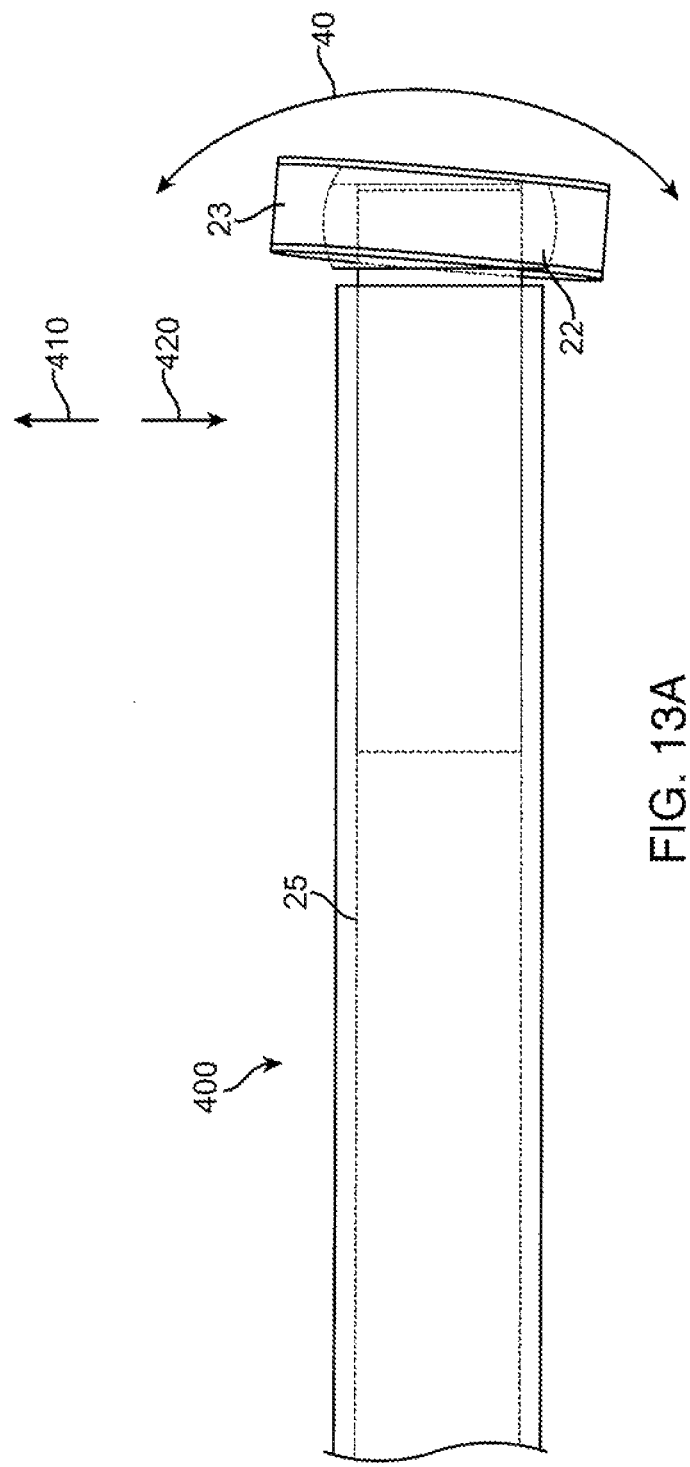
FIG. 13A shows a side view of the intermedullary rod with movement in the flexion/extension direction.

FIG. 13 shows a side view of the intermedullary rod 400 with movement in the flexion/extension direction 40. The movement of the coupling mechanism in direction 40 is particularly noteworthy because the bow of the intermedullary (IM) canal often influences the angular trajectory or protection of the intermedullary rod 400 itself. Anatomically, the canal is naturally bowed to the point that when a rod is inserted therein, the rod is influenced because of this very gradual natural bow of the femur (and the associated femoral canal). The human femur has a radius of approximately 78-80 cm. This influence has a propensity to put the femur into extension.

Figure 13B:
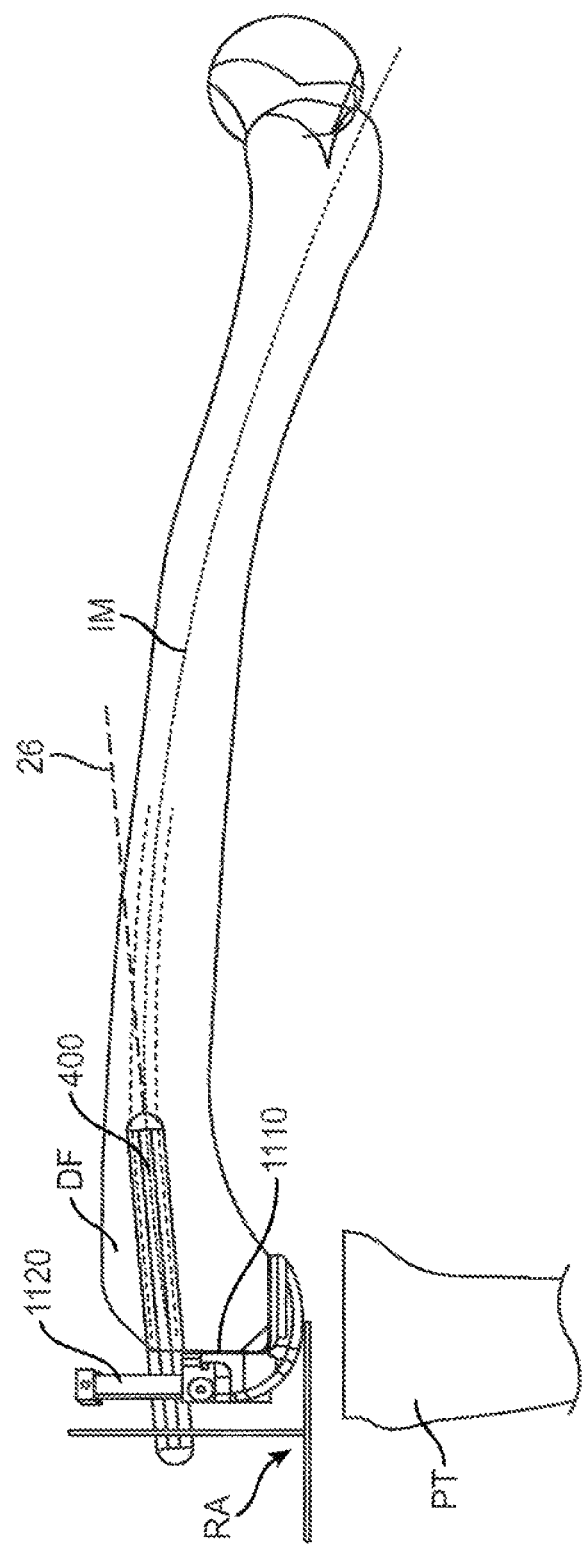
FIG. 13B shows the femoral adjustment member flush against the distal face of femur with the intermedullary rod placed in the femur.

FIG. 13B shows the femoral adjustment member 1100 flush against the distal face of the of the femur. The ball coupling in the vertical frame tilts posteriorly irrespective of flexion/extension angle of the intermedullary rod 400. The rod 400 enters the intermedullary (IM) canal which ascends anteriorly. The ball has freedom of motion to pivot in T slot 10. This allows the frame to sit flush against the distal face of the femur. If the frame was not pivotable, it would not sit flush against the face of the distal femur. As shown in FIG. 13B, the influence of intermedullary (IM) canal causes the intermedullary rod to tangentially track 26 the radius of the distal femur and intermedullary canal IM for an initial length but, because the rod is straight and relatively rigid, it cannot completely track the curvature of the femur. If the rod were flexible, it may be able to better track the radius on the femur; however, this results in an unbalanced knee. Specifically, this positions the knee in extension and closes down the femoral component up on the anterior flange instead of the anterior flange having an anterior-directed cant. This causes a mismatch of the posterior femoral condyle resulting in a "flexion state" in which flexion and extension are not well-balanced. In this unbalanced state, patients have reported "tightness" in their knee when the femur is placed in extension. In reality, the "tightness" is caused by an unbalanced knee pivoting about the incorrect axis. To mitigate this, the rod goes in the canal and is influenced. The coupling, including races 22 and 23, allows the femoral component to butt up against the distal femoral cut and the pivot mechanism self-centers. The surgeon is able to use the distal femoral cut as a reliable reference plane without any kind of obscure angle produced by the influence of the rod. Thus, it is possible to balance flexion space and extension space which are theoretically 90° perpendicular to each other. All intermedullary rod influence (and the effect of the bow of the femur in establishing the flexion extension gap) is mitigated.

Figure 14:
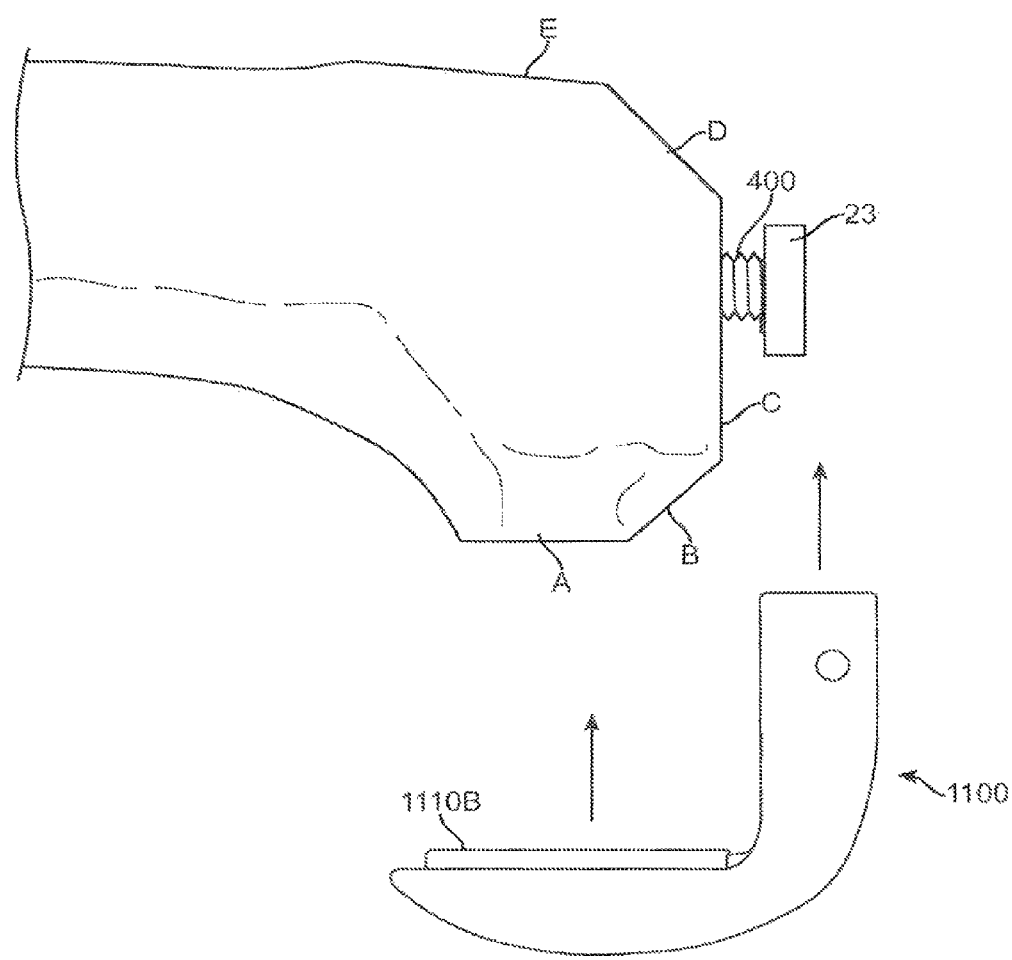
FIG. 14 shows a side view the intermedullary rod projecting out of the distal end of the femur with the femoral adjustment member positioned under the femur.
Figure 15:
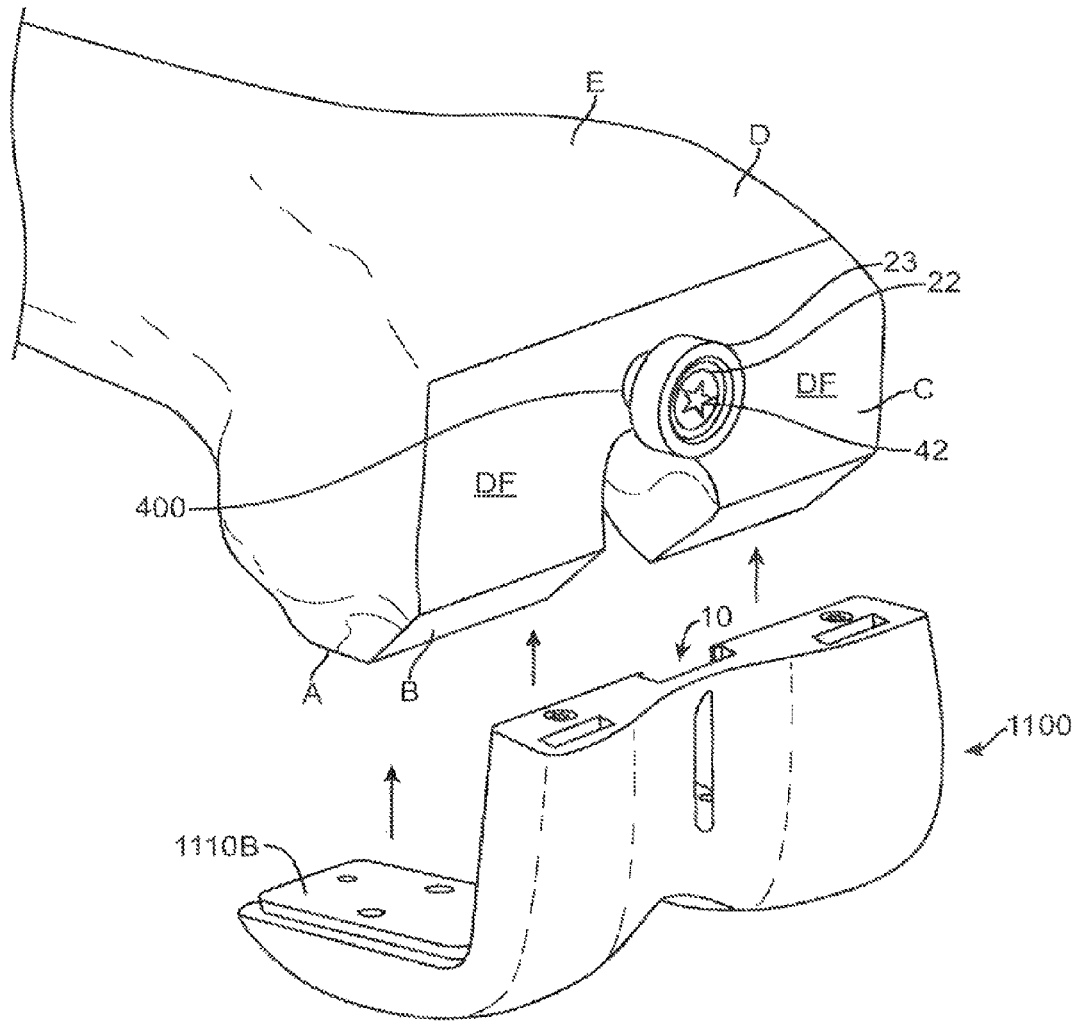
FIG. 15 shows a perspective view the intermedullary rod projecting out of the distal end of the femur with the femoral adjustment member positioned under the femur.

FIG. 14 shows a side view the intermedullary rod 400 projecting out the end of the distal femur with the femoral adjustment member 1100 positioned underneath the femur. The five cuts A-E made on the distal femur are also shown. The femoral adjustment member 1100 slides toward the femur until the condylar paddles 1110B (and 1110A obscured in this view) butt against femoral cut surface A while the outer race 23 slides into the T slot 10. The outer race 23 pivots about the inner race 22. FIG. 15 shows a perspective view of FIG. 14.

Figure 16:
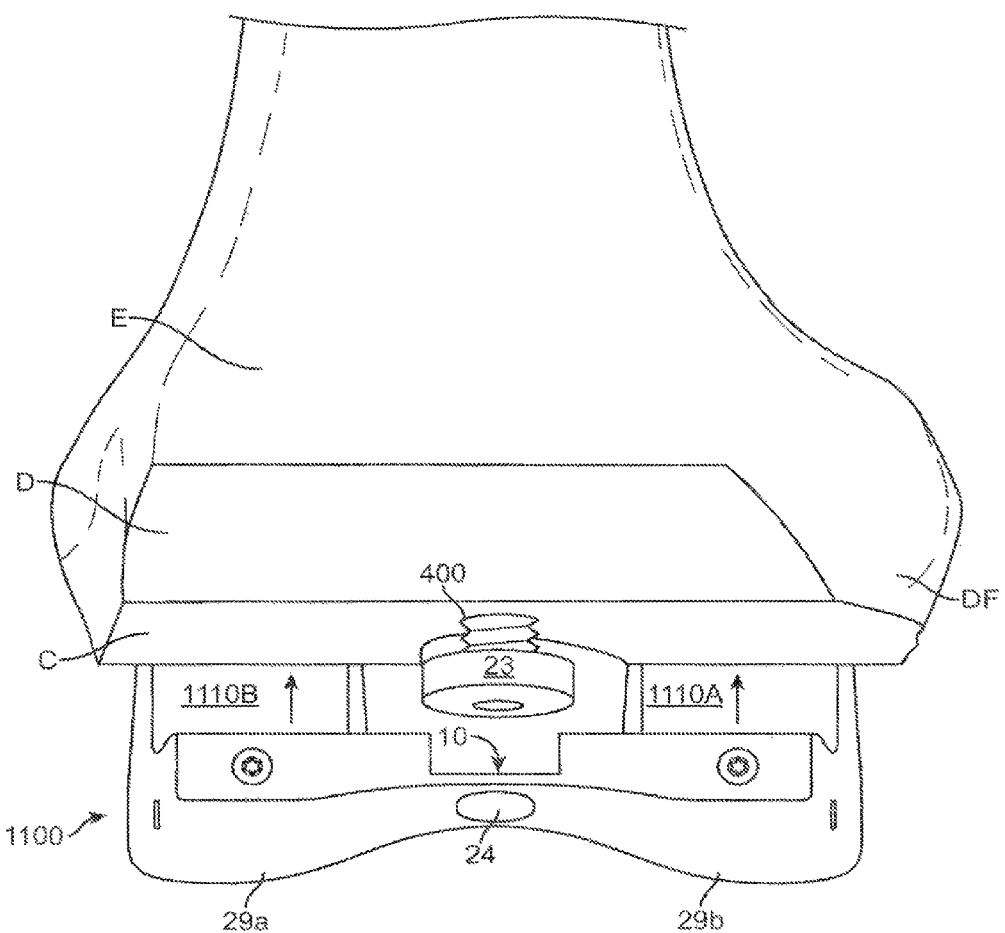
FIG. 16 shows a top view of the intermedullary rod projecting out the distal end of the femur with the femoral adjustment member positioned for attachment.

FIG. 16 shows a top view of the intermedullary rod 400 projecting out of the distal end of the femur. The distal femoral member 1100 is positioned to slide anteriorly toward the distal femur DF and the outer race 23 is positioned to slide into the T slot 10. This connects the distal femoral member to the distal end of the femur.

Figure 17:
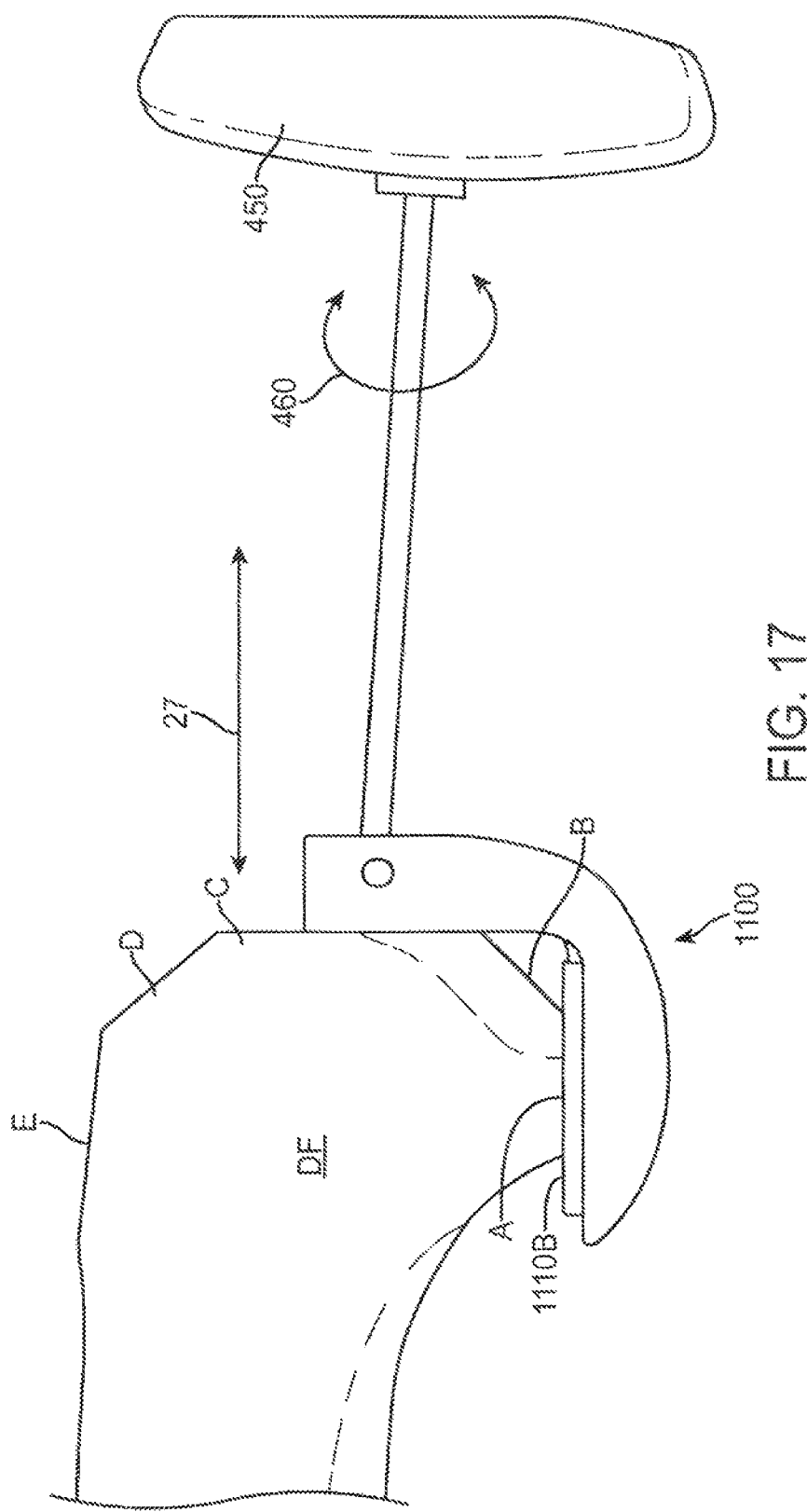
FIG. 17 shows a side view of the intermedullary rod attached to the femoral adjustment member and a screwing tool.

FIG. 17 is a side view after the outer race 23 has engaged the T slot 10 and femoral cut surface A rests against each condylar paddle 1110A, 1110B. A screwing tool 450 is interchangeably engaged 27 with a screw member 42 (shown in FIG. 15). The screwing tool 450 rotates screw member 42 which adjusts the intermedullary rod 400. This adjustment causes the rod 400 to move further into the IM canal to the point that the distal femoral surface is now butted against the distal femur surface cut C and also up against the posterior condyles of the cut surface A with no visible space between the cut surfaces and the femoral adjustment member 1100.

Figure 18:
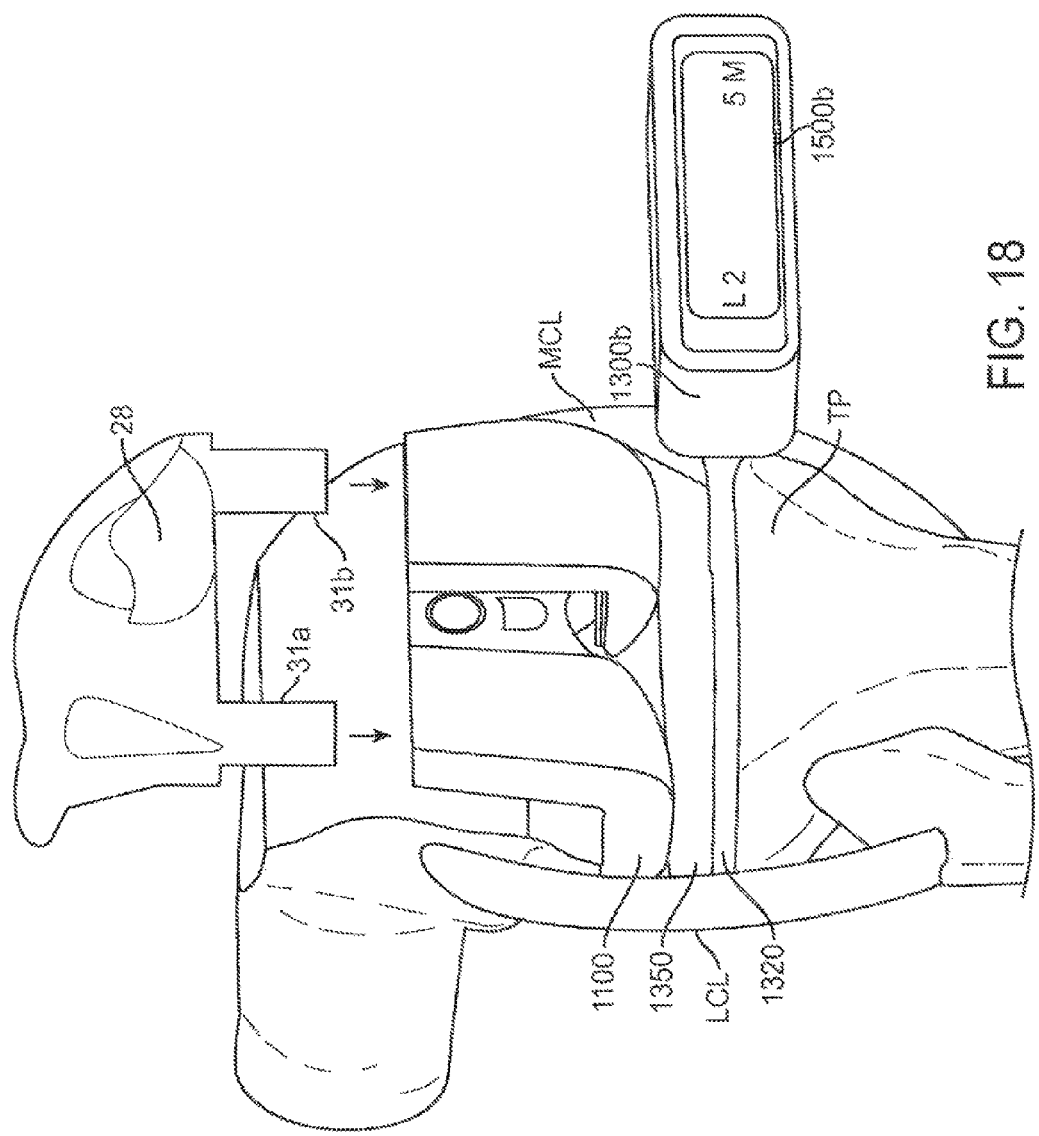
FIG. 18 shows a perspective view of a knee joint in flexion.

FIG. 18 shows a perspective view of a knee joint in 90 degrees of flexion. The patella and patella tendon have been removed from this view for clarity. A force sensor 1300b is shown including a force sensing portion 1320 and pad 1350 inserted between the tibial plateau TP and the femoral adjustment member 1100. For purposes of demonstration, initial force readings of two lateral (L2) and five medial (5M) are shown on integrated display 1500b. This indicates the lateral side has less force (i.e. is more lax) than the medial side, in this example. The lateral collateral ligament LCL and the medial collateral ligament MCL are currently unbalanced. The tangs 31a and 31b of the anterior patellar groove 28 section can now slip into the femoral adjustment member 1100 through grooves 29a and 29b, respectively (shown in FIG. 16).

Figure 19:
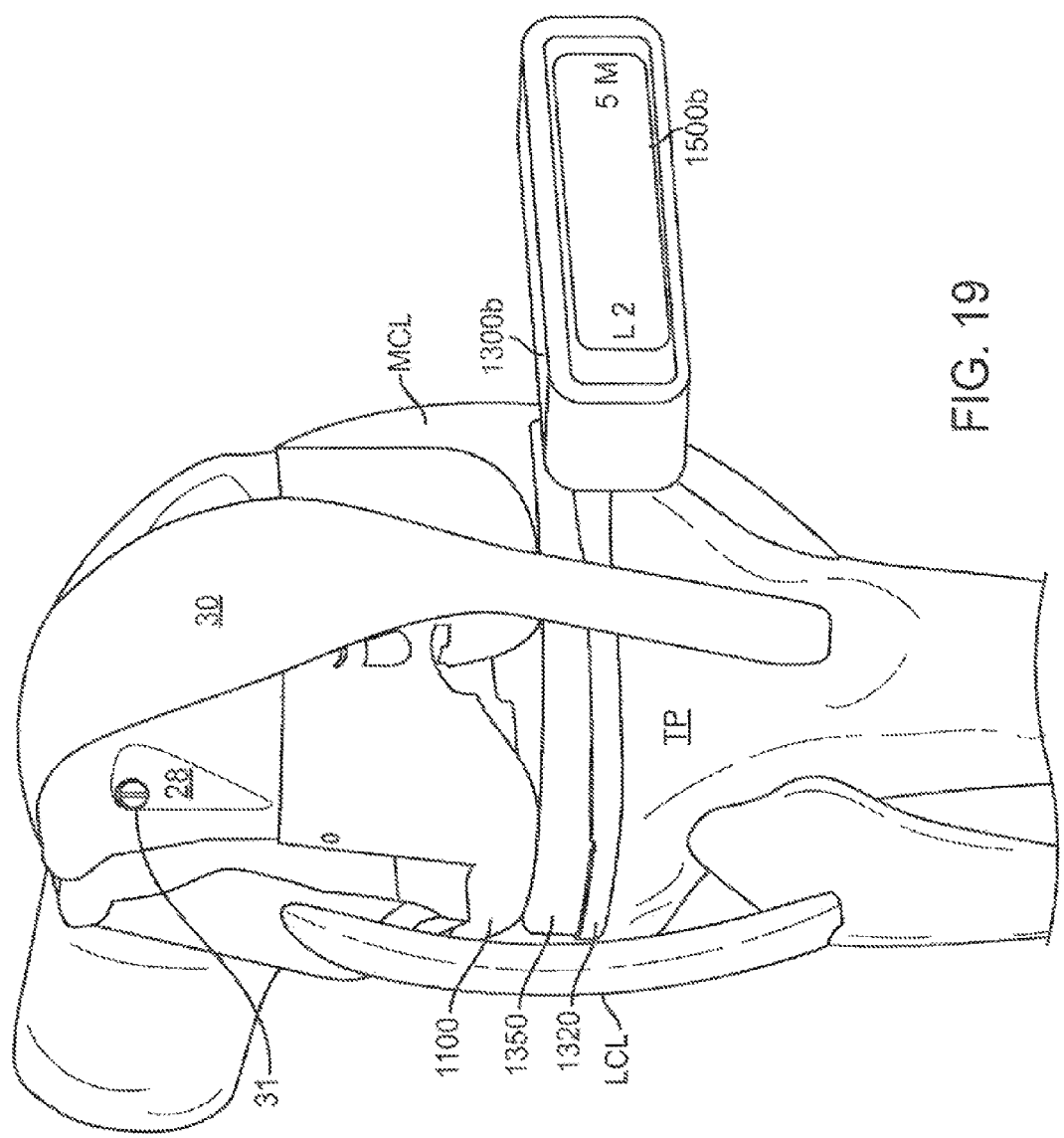
FIG. 19 shows a perspective view of at knee joint in flexion with the anterior patella groove section and patella tendon in place.

FIG. 19 shows a perspective view of a knee joint in 90 degrees of inflexion with the anterior patella groove section 28 and the patella tendon in place 30. Although the patella has been reduced, the force sensor 1300b displays the same reading, namely, two lateral (L2) and five medial (5M) as before patella reduction.

Figure 20:
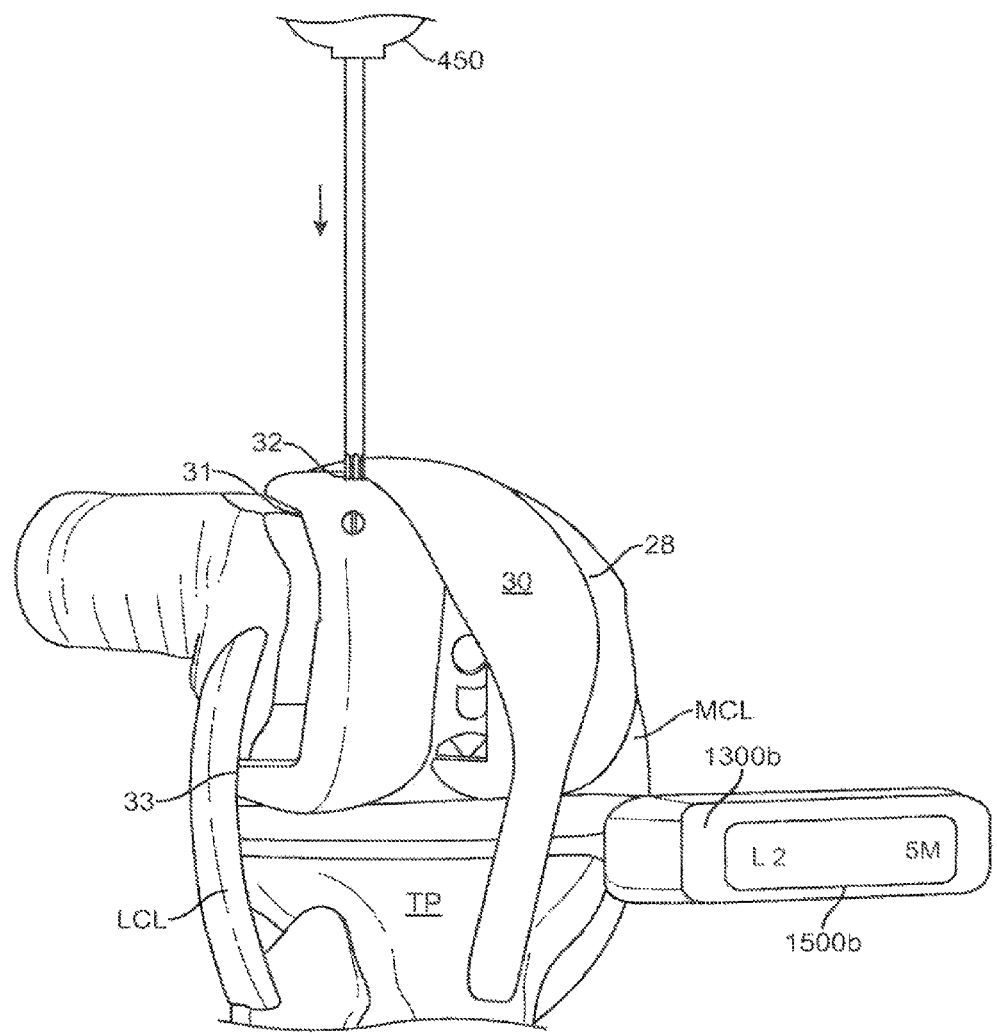
FIG. 20 shows the screwing tool positioned toward an adjustment aperture.

FIG. 20 shows the wrench tip 32 of screwing tool 450 moving to engage an adjustment aperture 31. The adjustment aperture 31 accesses the lateral side of the patella groove section 28. FIG. 20 shows the knee joint remaining in 90 degrees of flexion just prior to adjustment. The knee remains unbalanced and the screwing tool has not yet been rotated to adjust the lateral collateral ligament.

Figure 21:
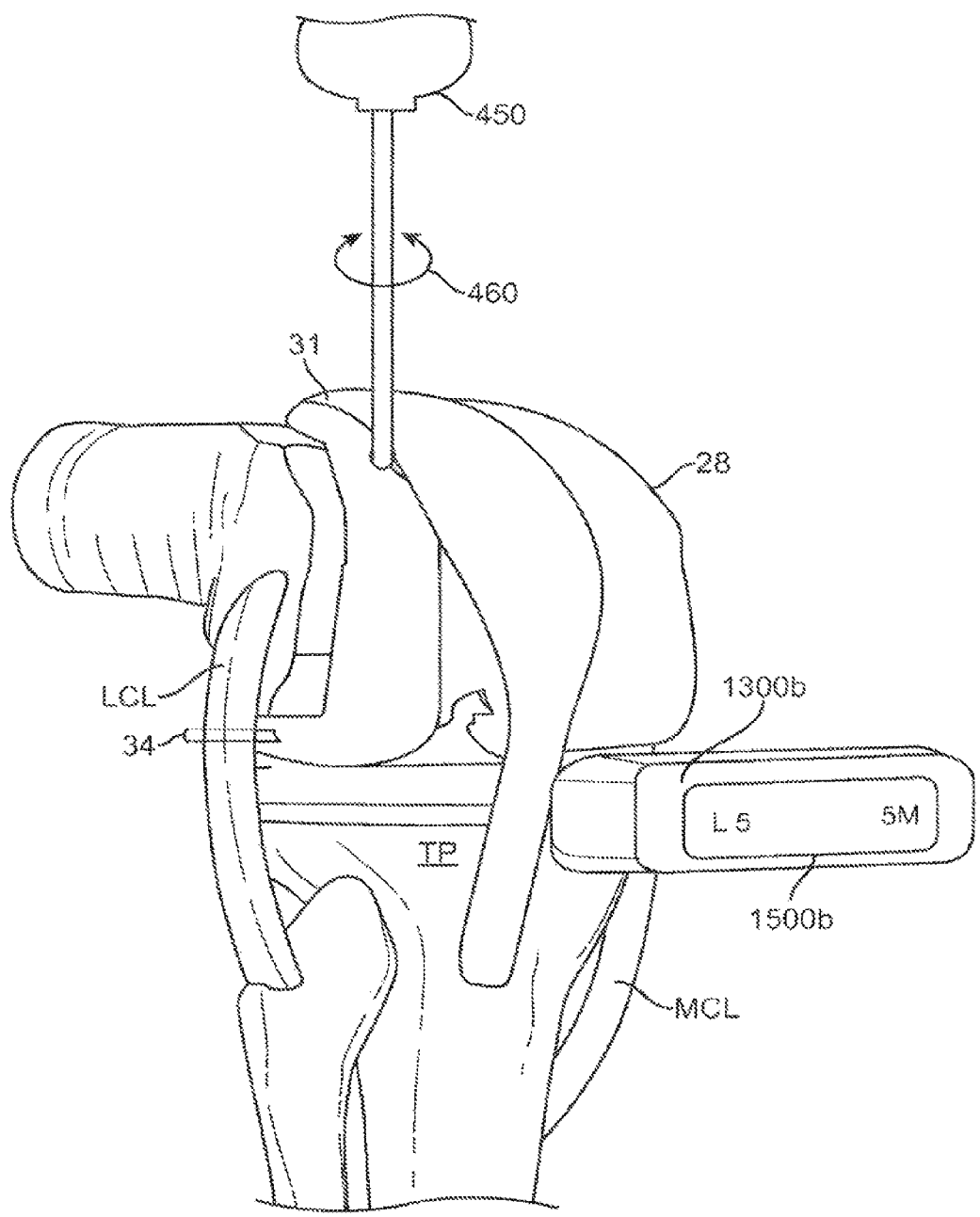
FIG. 21 shows the screwing tool engaged with the adjustment aperture.

FIG. 21 shows screwing tool 450 now engaged with an adjustment aperture 31. Adjustment is accomplished by turning the screwing tool 450 clockwise or counterclockwise 460 to adjust ligament tension as indicated by the force sensor display 1500b. In this example, the lateral side has now been adjusted so the medial collateral ligament MCL and the lateral collateral ligament LCL are balanced in tension as can be verified by the force sensor display 1500b reading of five lateral (L5) and five medial (5M). By comparing the lateral skid space 33 in FIG. 20 (before adjustment) and the lateral skid space 34 in FIG. 21 (after adjustment), the lateral space has increased to bring the knee ligaments in balance by externally rotating the femoral component (i.e. the lateral side of the femur has been raised). Anatomically, knee stability originates on the medial side of the knee joint. Therefore, it is preferred to register a force reading on the medial side. Sometimes this may require one or more shims to be inserted between the tibial plateau TP and the femoral adjustment member 1100, for example. The lateral side is brought in balance with the medial. If a reading on the medial side cannot be obtained even after inserting shims between the tibial plateau TP and the femoral adjustment member 1100, the medial structure is incompetent and the patient is not a candidate for soft tissue balancing, as described herewith.

Figure 22:
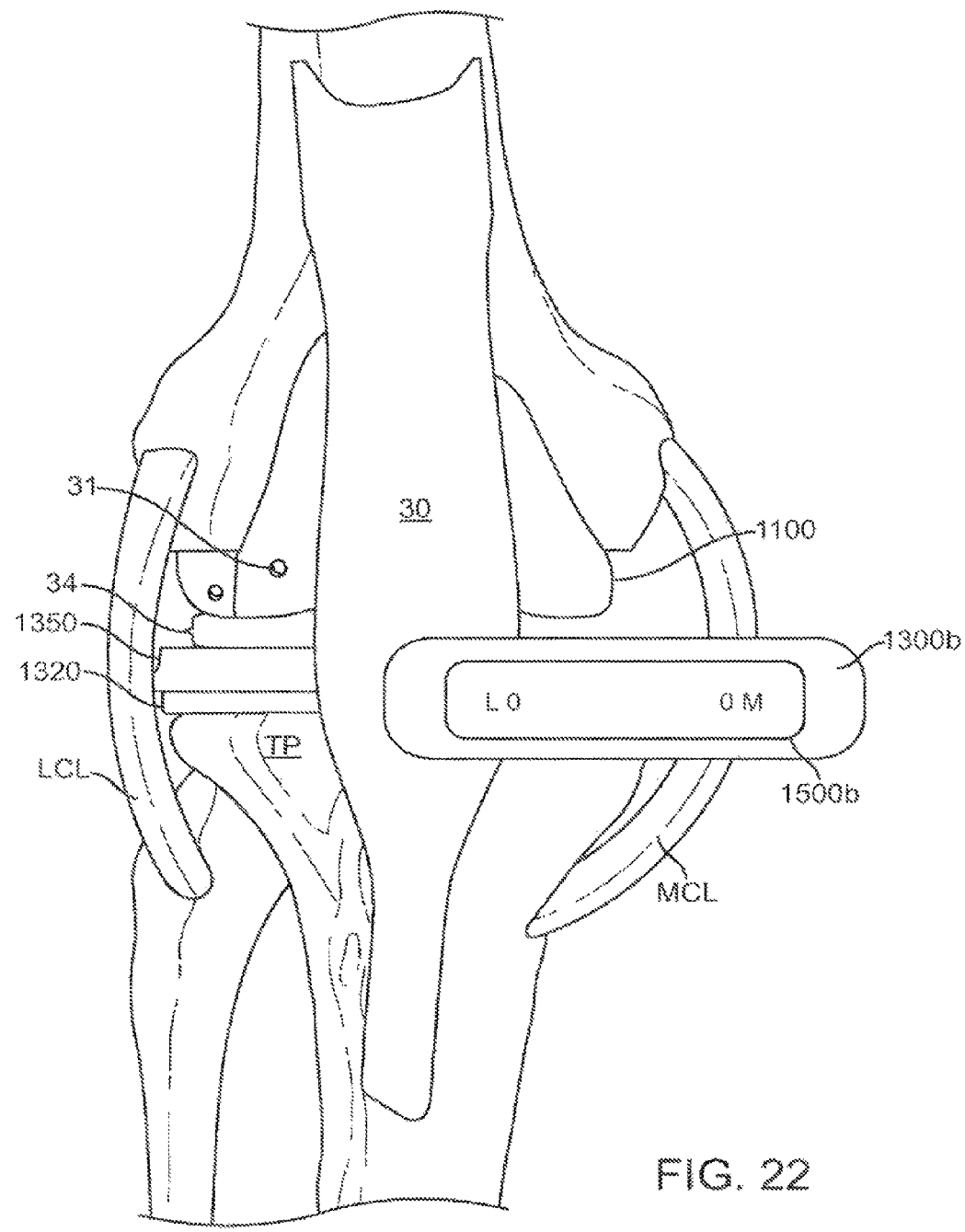
FIG. 22 shows a top view of a lax knee joint in extension.

FIG. 22 shows a top view of a knee brought into extension by raising the lower leg. A lax medial collateral ligament MCL and a lax lateral collateral ligament LCL are verified by the force sensor display 1500b reading of zero lateral (L0) and zero medial (0M). This reading is also consistent with a noticeable space 34 that now exists between the pad 1350 inserted between the tibial plateau TP and the femoral adjustment member 1100. Note that this space 34 did not exist when the knee was in 90 degrees of flexion and the ligaments were in balance (FIG. 21). This space 34 in extension is often caused because the joint lines in the primary knee have often been made too far in the proximal direction. This may result in a plethora of issues including patella tracking problems, for example. To avoid these issues, a correctly chosen augment element thickness is used to close the extension space 34 and reestablish the joint line.

This is done by first positioning the extended leg back into flexion. The patella tendon 30 is moved to access screw member 26. An screwing tool 450 is interchangeably engaged with a screw member 26 (shown in FIG. 17). The screwing tool 450 rotates to adjust the in intermedullary rod 400. This adjustment causes the rod 400 to move in a telescopic fashion out of the intermedullary canal to allow the anterior patella groove section 28 to be removed and replaced with a thicker augment element. This provides a shim between the backside of the femoral adjustment member and cut C on the distal femur. Thus, the distal femoral surface is now butted against the augment element of anterior patella groove section 28. The leg is placed back into extension to determine if the space 34 has been filled. These steps may be repeated until as properly sized augment element has been chosen such that the space 34 is closed in extension.

For comparison, a side view of a patellar groove 28 section without an augment element is shown in FIG. 23.

Figure 23A:
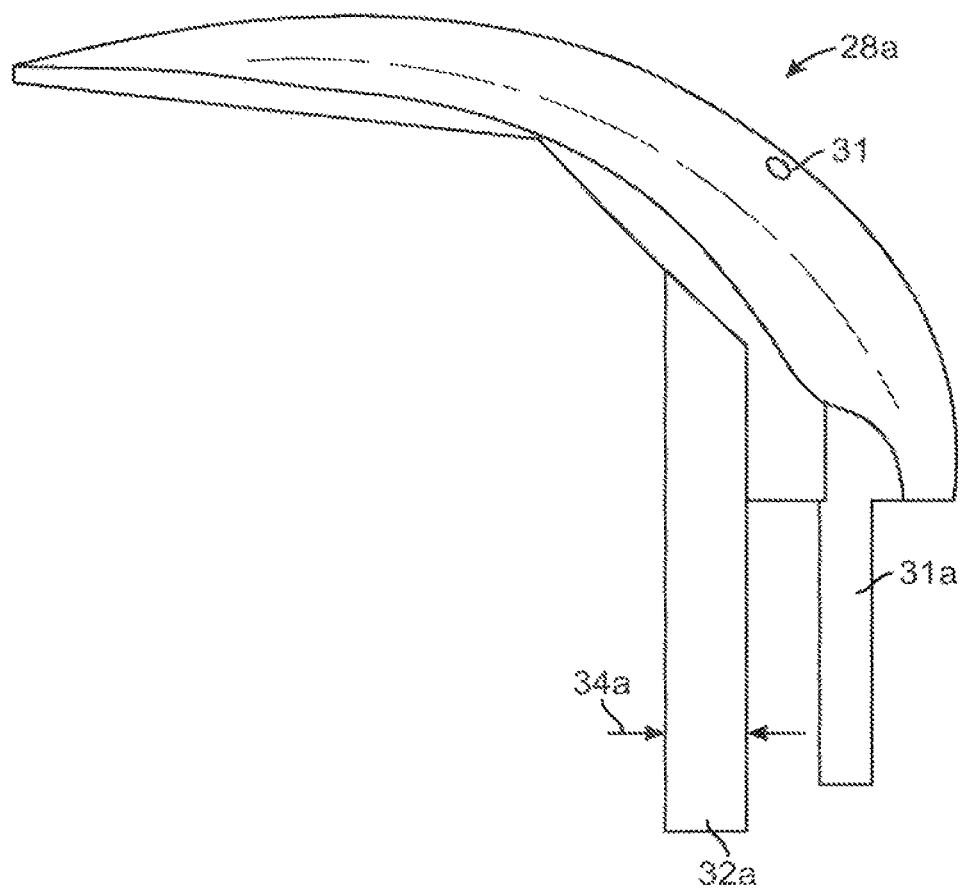
FIGS. 23A, 23B and 23C show a series of patellar groove sections with augment elements of varying thickness.
Figure 23B:
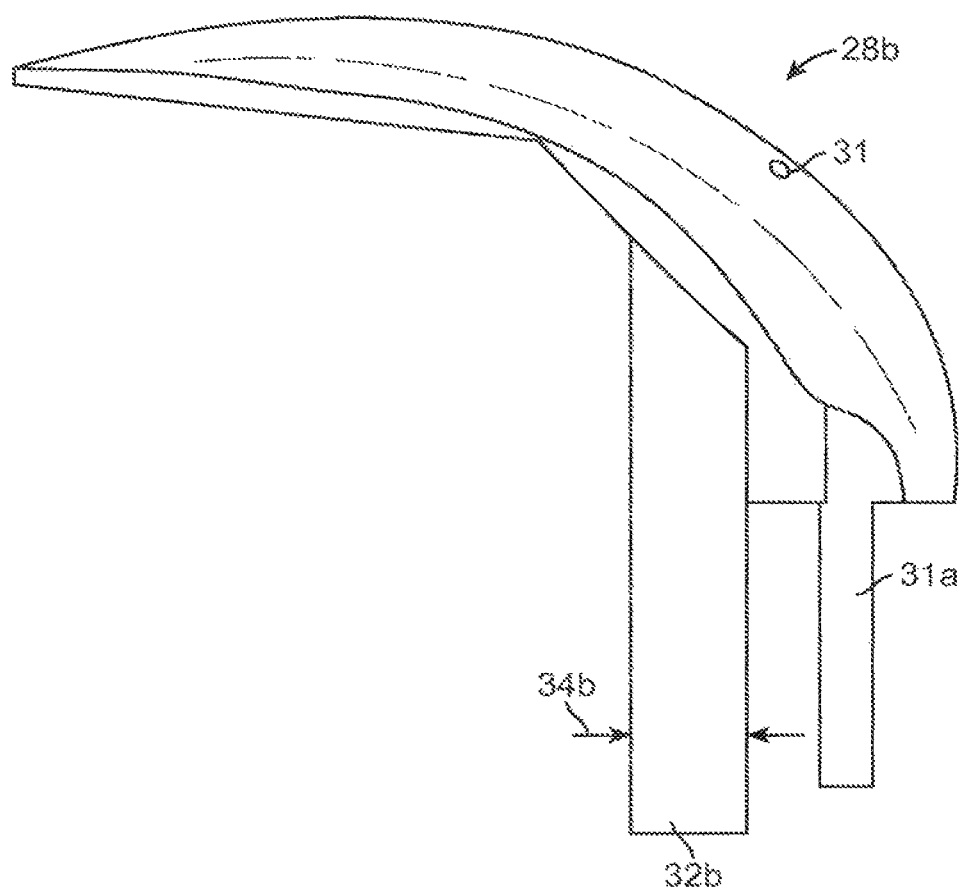
Figure 23C:
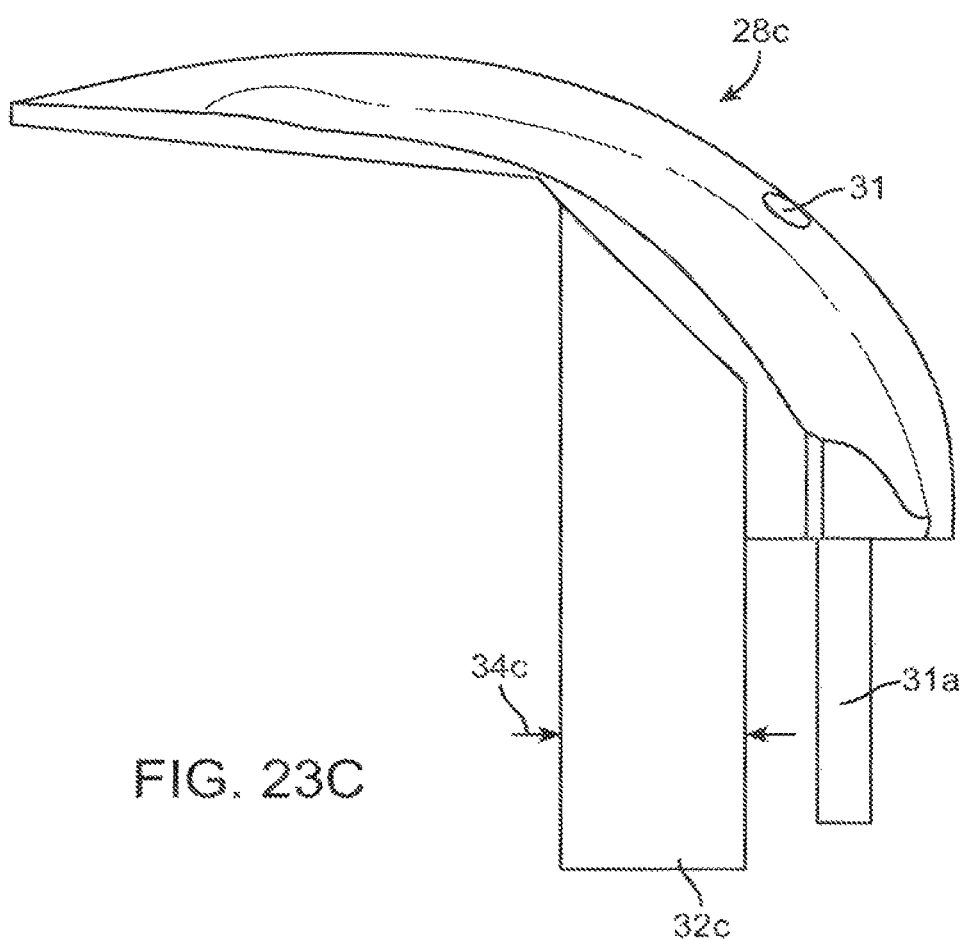

FIGS. 23A-23C show side views of a series of three patellar groove sections with progressively thicker widths 34a-34c of augment elements 32a-32c, respectively, attached. The augment elements 32a-32c are thickened anterior patella femoral pieces. Many thicknesses or combinations of thicknesses may be used and are not necessarily limited to these three exemplary sizes. Regardless of the thickness, the augment abuts the distal femur. FIG. 23A shows a side view of the patellar groove 28a section of the original anterior patella femoral piece that was in place when the knee was balanced in flexion (FIG. 21). Thus, augment element 32a represents the nominal/minimal thickness. To achieve a force reading in extension, a thicker augment will need to be introduced to fill the space 34 shown in FIG. 22. The augment elements are loaded into the femoral adjustment member with the same two tangs 31a and 31b positioned on the front of the patellar groove section and still slide into the femoral adjustment member in the same slots 29a and 29b. The augment elements function like shims. They are integral with the patellar groove 28 section in this example. FIGS. 23A1-23B1 show a side view of FIGS. 23A and 23B in context with surrounding related anatomical structures and the femoral adjustment member.

Figure 23D:
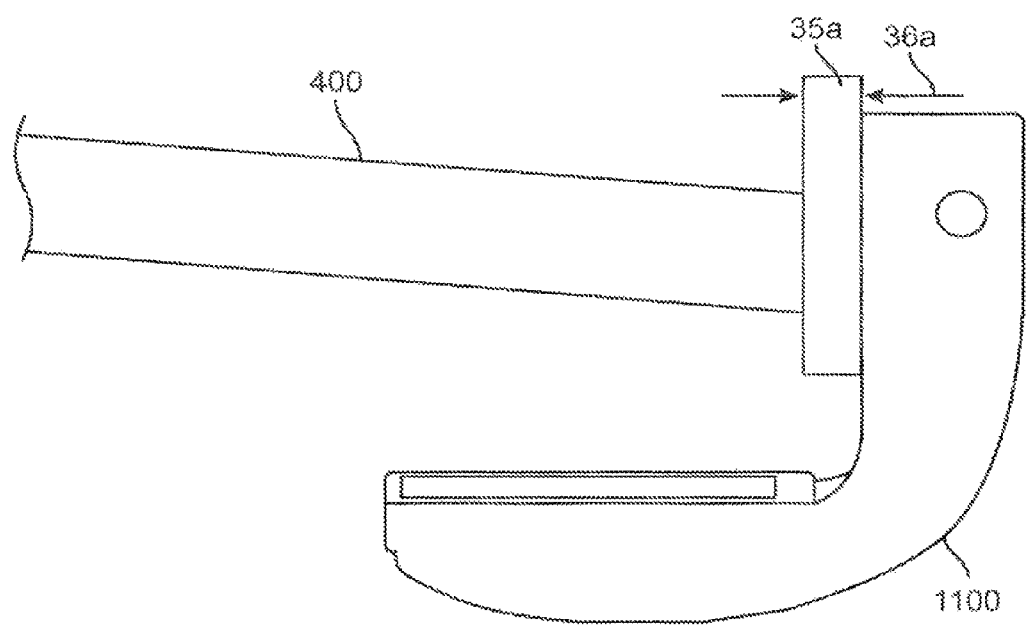
FIGS. 23D-23F show a side view of augment elements according to embodiments of the invention.
Figure 23E:
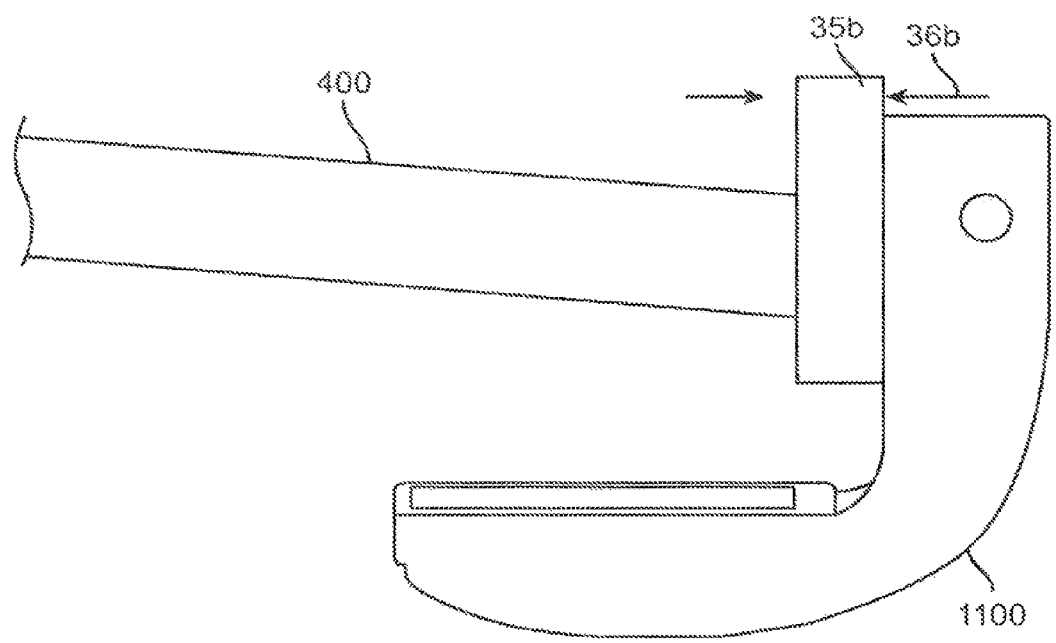
Figure 23F:
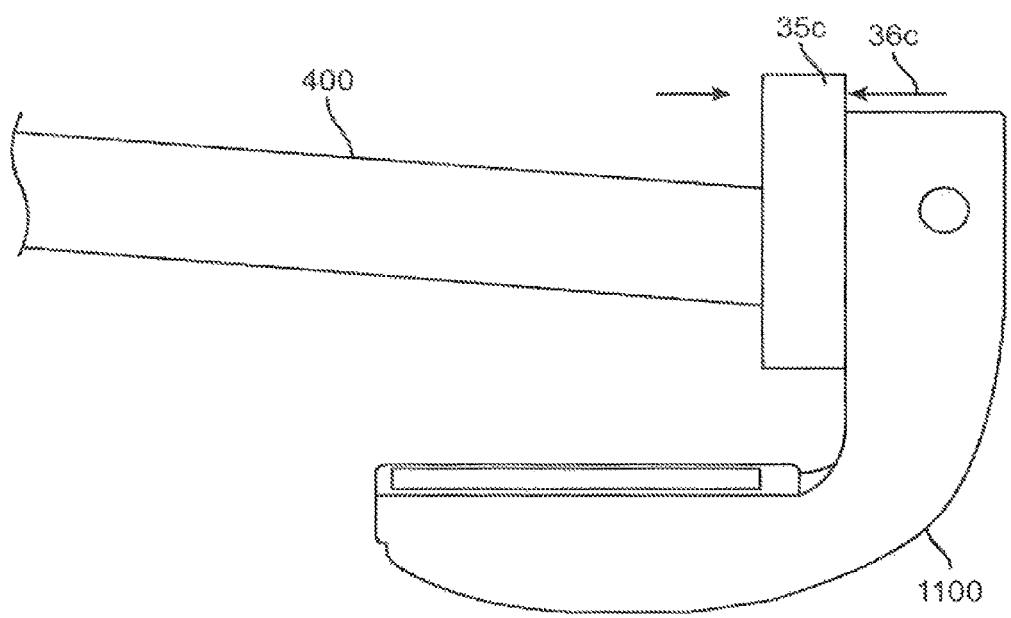

FIGS. 23D-23F show side views of an alternative embodiment of the augment elements in which they are separately attachable to the femoral adjustment member 1100. The augment elements may attach to the femoral adjustment member 1100 magnetically or slide or clip into place, for example. Progressively thicker widths 36a-36c of augment elements 35a-35c are attached to femoral adjustment member 1100 and straddle the intermedullary rod 400.

Figure 23G:
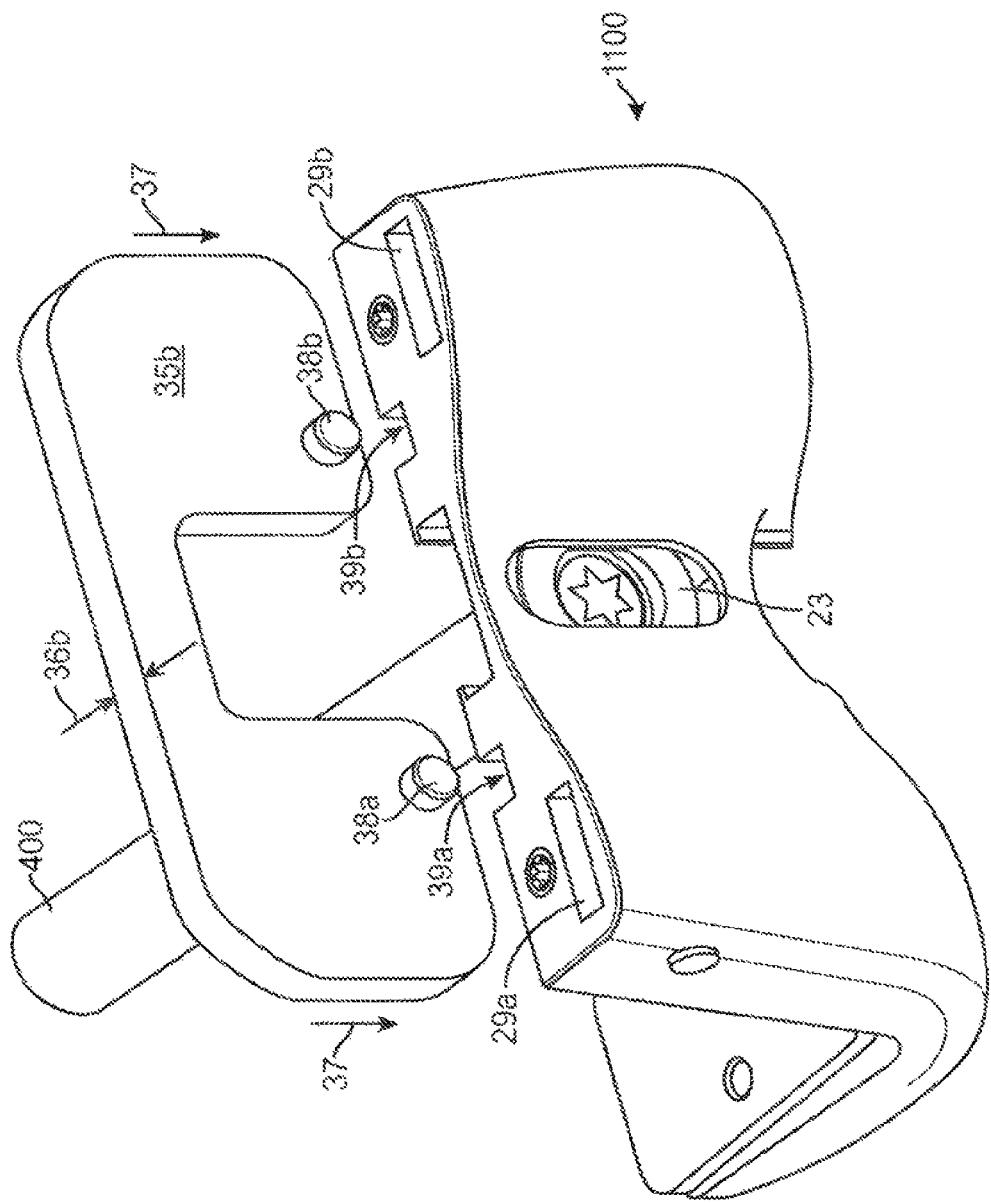
Figure 23I:
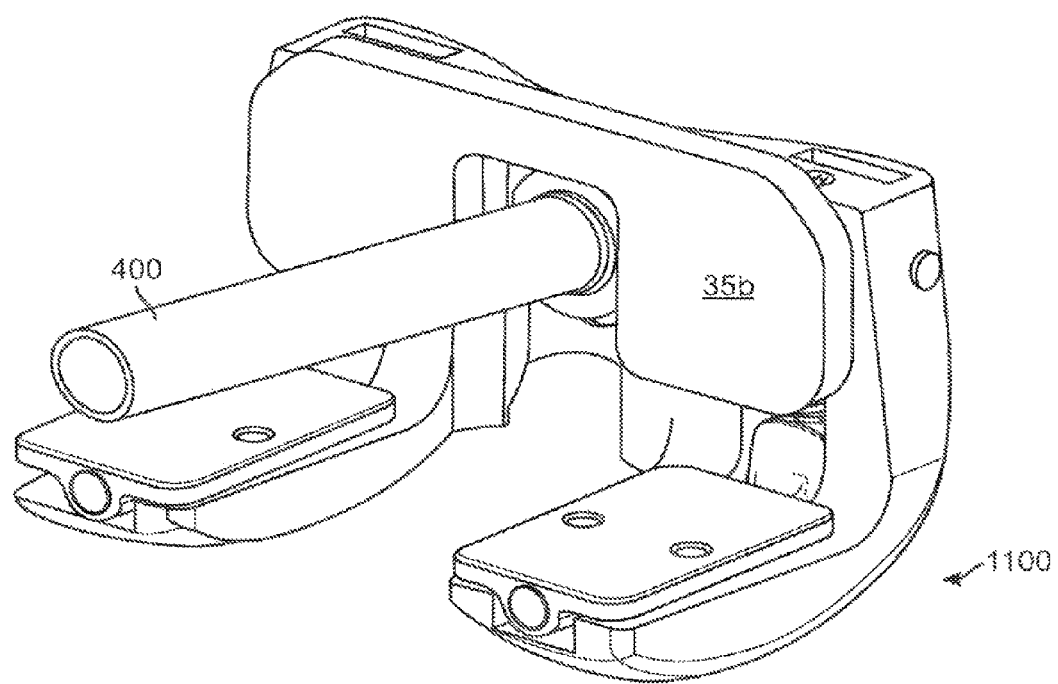

FIGS. 23G-23I show perspective views of yet another alternative embodiment of the augment element in FIG. 23E. FIG. 23G shows protrusions 38a and 38b of augment element 35b sliding in direction 37 into engagement tracks 39a and 39b, respectively, of femoral adjustment member 1100. FIG. 23H is the same perspective after the augment element has been attached to the femoral member. Augment element 35b straddles the intermedullary rod 400 and abuts the distal femoral cut C (not shown in FIGS. 23G-23I).

Figure 24:
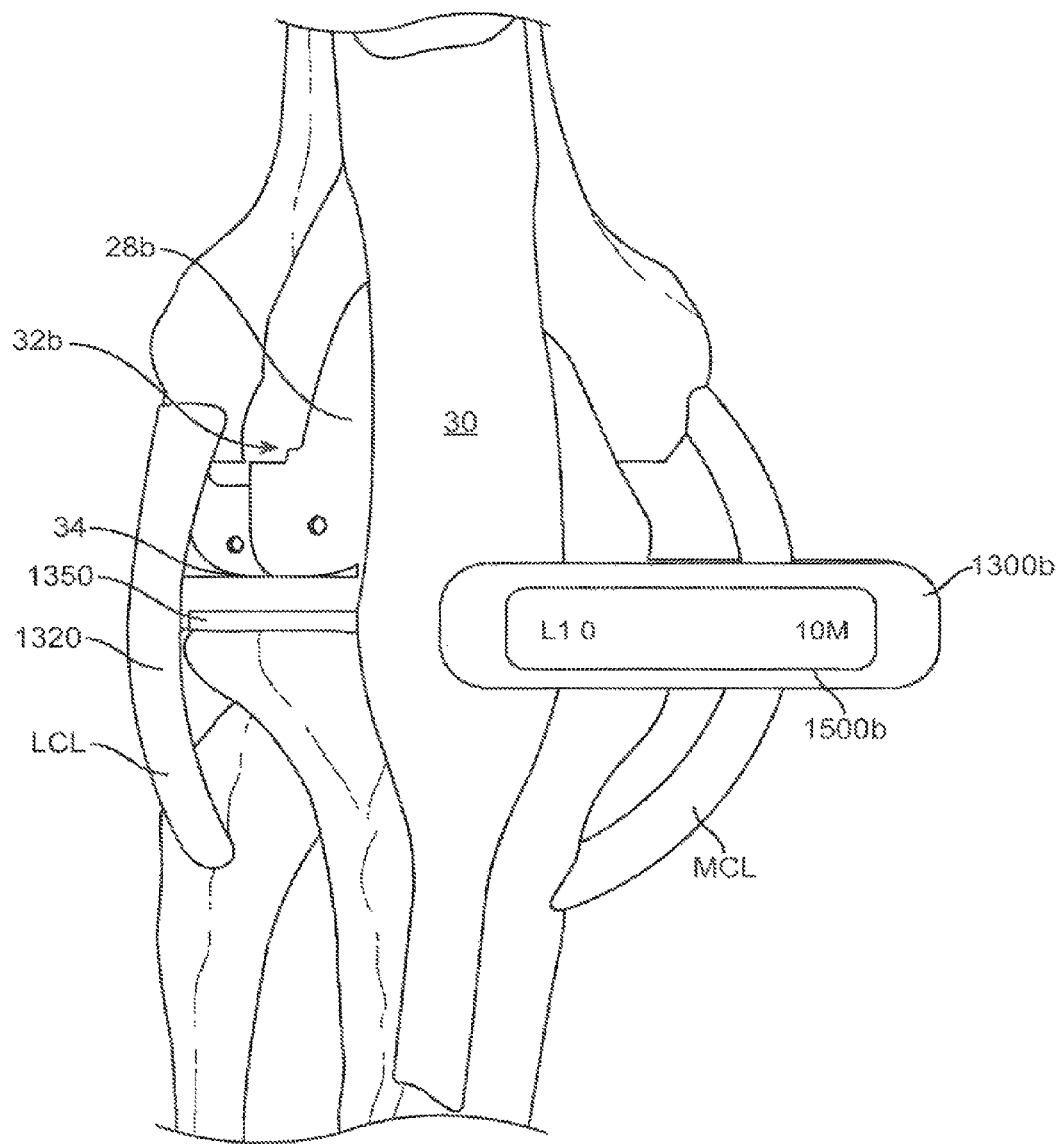
FIG. 24 shows a top view of a balanced knee joint according to embodiments of the invention.

FIG. 24 shows top view of a knee in extension. The medial collateral ligament MCL and lateral collateral ligament LCL are verified by the force sensor display 1500b reading of ten lateral (L10) and ten medial (10M) indicating that the knee is in balance in extension (as well as flexion) and the joint line has successfully been reestablished by choosing the correct augment element thickness. The patella tendon comes into balance when the joint line is established. This reading is also consistent with the space 34 that has now been closed between the pad 1350 located between the tibial plateau TP and the femoral adjustment member 1100. While a well balanced knee with an extension space may be approximately 2× the flexion space, in this example, it does not necessarily have to be this relationship. The preferred factor is that the medial collateral ligament MCL and the lateral collateral ligament LCL are in balanced in tension with lateral and medial force sensor readings being very close or equal to one another.

Once the medial collateral ligament MCL and lateral collateral ligament LCL are in balance in extension and flexion and the joint line has been reestablished, a clean-up cut on the anterior surface of the femur can be made. The clean-up cut up is taken at an angle so as to properly account for the influence of the femoral curve and correct cuts previously made to the anterior side of the distal femur in previous knee replacement surgery procedure(s).

Figure 25A:
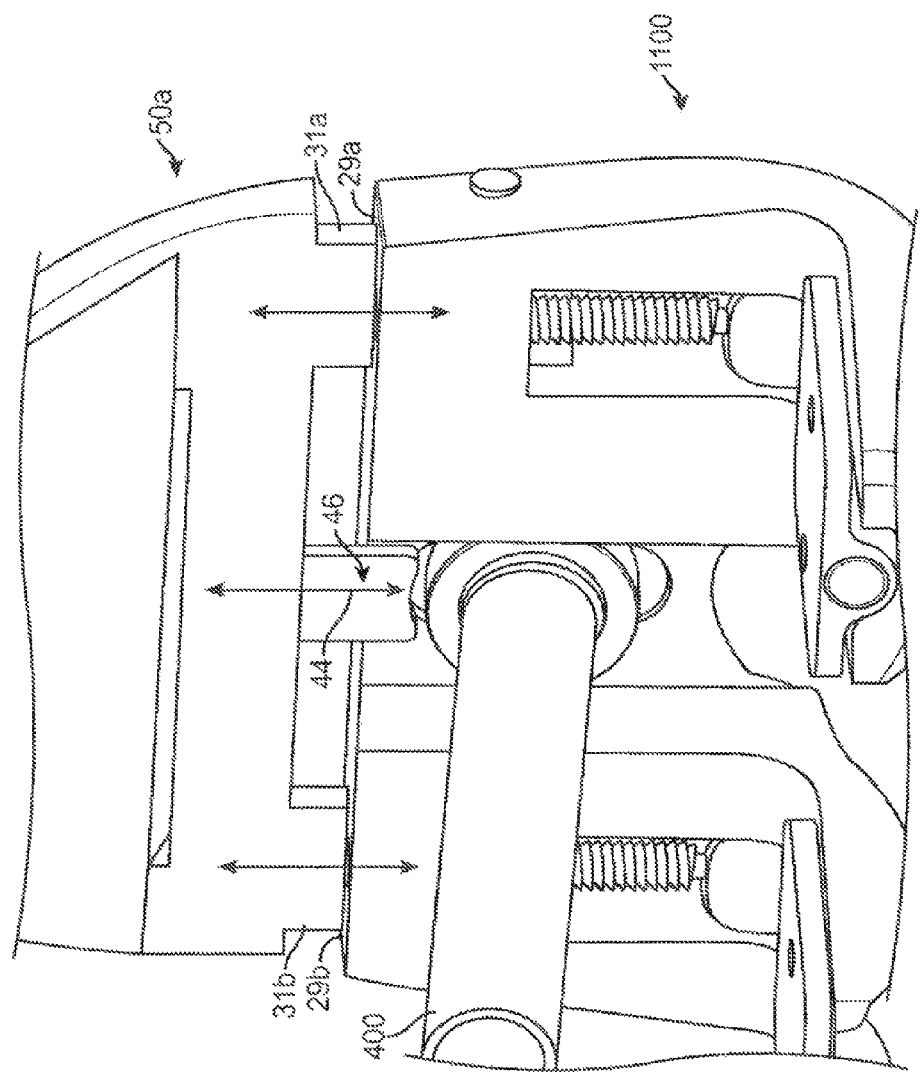
Figure 26A:
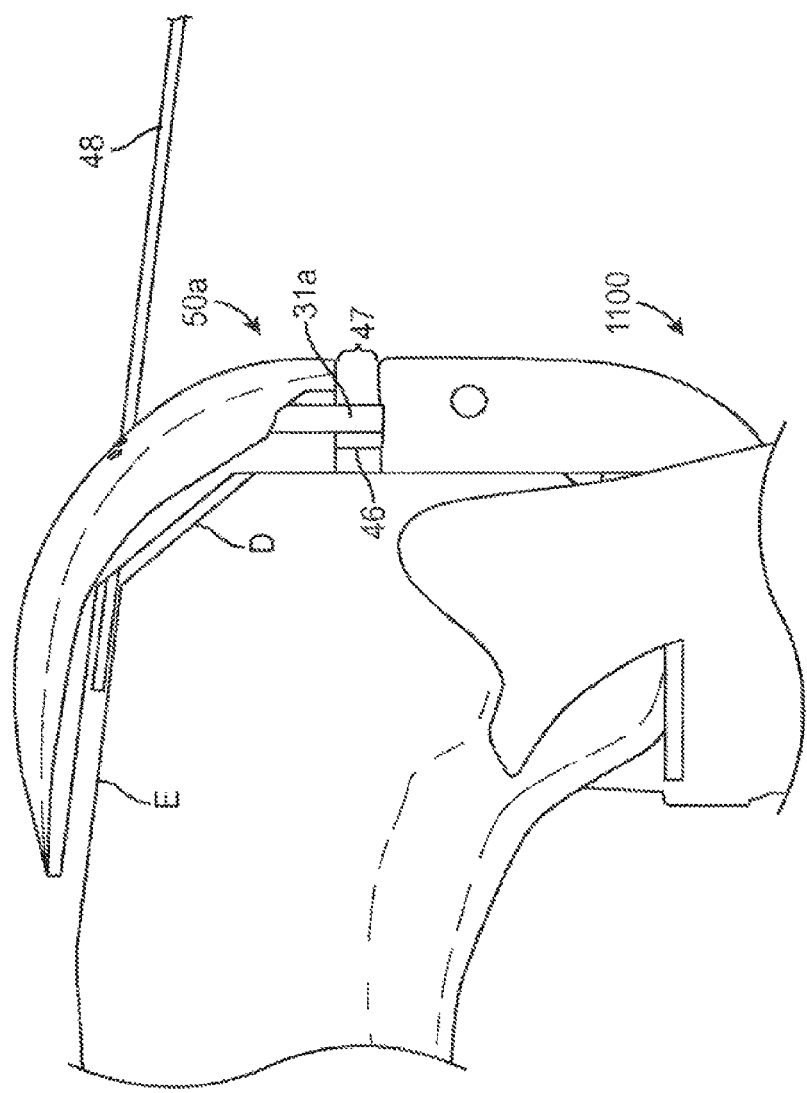
FIG. 26A shows a side view of as cutting guide positioned too high to make a nominal clean-up cut on the femoral bead according to embodiments of the invention.
Figure 26B:
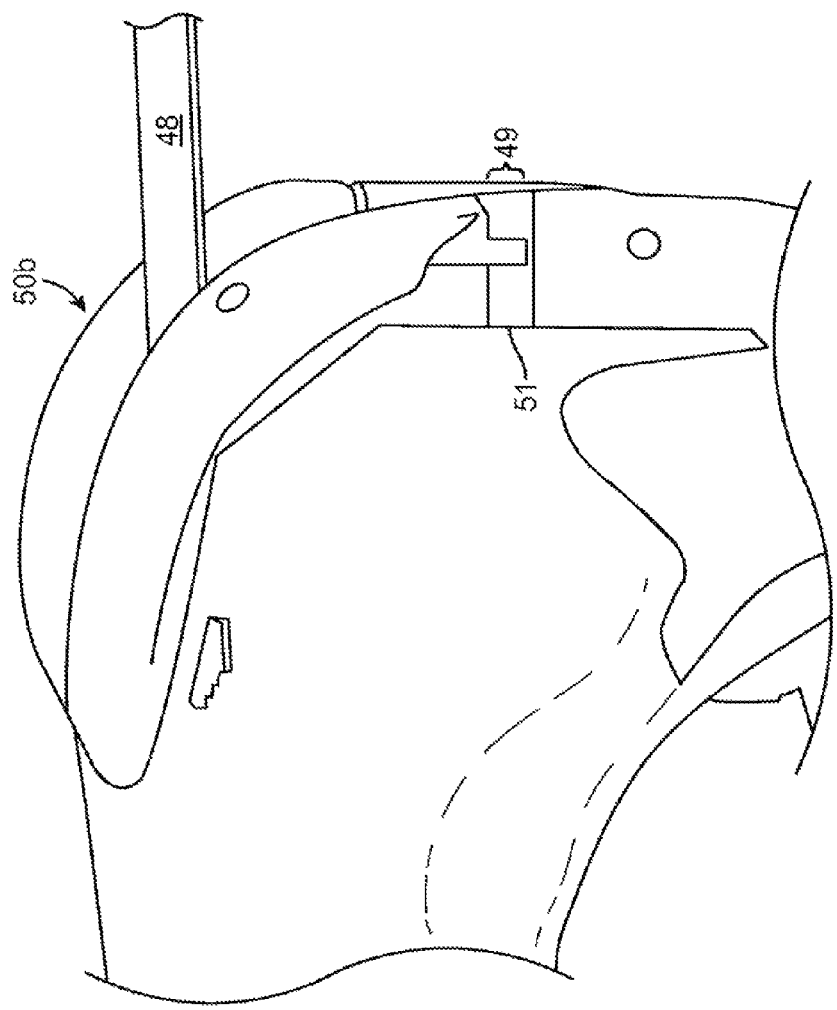
FIG. 26B shows a side view of a cutting guide correctly positioned to make a nominal clean-up cut on the femoral head according to embodiments of the invention.

Once the low profile embodiment shown in FIG. 25A, a key 46 is attached to the anterior patella cutting guide 50a. Tangs 31a and 31b of the cutting guide 50a engage slots 29a and 29b, respectively, in the femoral adjustment member 1100 as the cutting guide slides in direction 44 toward the femoral member 1100. FIG. 25B shows the key 46 resting on the outer race 23 of the intermedullary rod 400 with a gap 47 between the cutting guide 50a and femoral adjustment member 1100. In this embodiment, the key 46 serves a similar purpose as the locking clamp 1200 described in a previous embodiment; however, instead, of choosing a side of the locking clamp to position higher or lower against a reference cutting guide, the height of the key 46 is adjusted to raise or lower the cutting guide. An example where the height of key 46 is too tall (i.e. gap 47 is too large) is shown in FIG. 26A. The cutting guide 50a is positioned too high so that when the blade 48 is inserted into the cutting guide, it does not contact bone and thus cannot make a clean-up cut. Accordingly, the anterior patella cutting guide 50a is replaced with a new anterior femoral piece 50b, shown in FIG. 26B. This cutting guide has a shorter key 51 that produces a smaller gap 49. The cutting guide 50b positions the blade 48 to make a nominal clean-up cut on the anterior surface of the femur. This nominal cut provides a clean surface to establish femoral component rotation. By comparison, FIG. 26C illustrates a scenario in which a very short key is used that positions the cutting guide 50c too low. Thus, blade 48 removes too much bone during the clean-up cut raising the potential of femoral fracture. The anterior patella cutting guides may be switched between key height positions without the need to reconfigure or reposition any component of femoral adjustment member 1100 and intermedullary rod 400. The goal is to guide blade 48 to engage a minimal amount of bone to complete a clean-up cut to reestablish the rebalanced rotation but not remove so much bone that the integrity of the femoral cortex or shaft is compromised.

After the clean-up cut is made, the cutting guide is removed from the femoral adjustment member and the femoral adjustment member is removed from the distal femur. A second cutting guide can be placed on the distal femur to make a subsequent cut based on the first cut. The clean-up cut provides a reference to make secondary and/or tertiary cuts, to complete the shaping of the distal femur to receive the new femoral component.

While the above is a complete description of the embodiments of the invention, various alternatives, modifications, and equivalents may be used. Therefore, the above description should not be taken as limiting in scope of the invention which is defined by the appended claims.

What is claimed is:

1. An adjustable femoral provisional component comprising:
    a femoral adjustment member securable to a distal femur and adapted to enable ligament balancing during a surgical procedure on a knee, the femoral adjustment member including a medial adjustment mechanism and a lateral adjustment mechanism, the medial and lateral adjustment mechanisms configured to create adjustable distances between a distal surface of the femoral adjustment member and resected surfaces of the distal femur;
    an anterior patellar groove member couplable with an anterior surface of the femoral adjustment member to form a provisional distal femoral surface, the anterior patellar groove member including a proximal surface configured to contact at least a first resected surface of the distal femur, wherein the provisional distal femoral surface is adapted to provide ligament balancing through adjustment of the femoral adjustment member through a full range of patella tracking; and
    an augment element disposable between a portion of the femoral adjustment member and a distal resected surface of the distal femur when the anterior patellar groove member is coupled with the femoral adjustment member, the augment element adapted to assist in ligament balancing with the knee in extension.

2. The adjustable femoral provisional component of claim 1, wherein the medial and lateral adjustment mechanisms are each configured to contact a second resected surface of the distal femur.

3. The adjustable femoral provisional component of claim 2, wherein first resected surface is an anterior surface and the second resected surface is a posterior surface substantially opposing the first resected surface.

4. The adjustable femoral provisional component of claim 2, wherein the femoral adjustment member and the anterior patellar groove member, when coupled, are configured to contact a third resected surface on the distal femur, wherein the third resected surface is substantially perpendicular to a long axis of the femur.

5. The adjustable femoral provisional component of claim 4, wherein the augment element is configured to be disposed between a portion of the femoral adjustment member and the third resected surface when the anterior patellar groove member, is coupled with the femoral adjustment member.

6. The adjustable femoral provisional component of claim 5, wherein the augment element is an integral portion of the anterior patellar groove member.

7. The adjustable femoral provisional component of claim 5, wherein the augment element is separately attachable to the femoral adjustment member.

8. The adjustable femoral provisional component of claim 7, wherein the augment element is attachable to the femoral adjustment member by at least one attachment mechanism of the following group of attachment mechanisms:
    magnet;
    clip; and
    slide.

9. The adjustable femoral provisional component of claim 5, further including a plurality of augment members, wherein each augment member maintains a different gap distance between the femoral adjustment member and the third resected surface.

10. The adjustable femoral provisional component of claim 1, wherein the femoral adjustment member and the anterior patellar groove member, when coupled, form a trochlear groove oriented along a substantially anterior-to-posterior axis through at least a portion of the provisional distal femoral surface.

11. The adjustable femoral provisional component of claim 1, further comprising a force sensor apparatus adapted to slidably contact the provisional distal femoral surface and provide force or pressure readings separately from the medial and lateral sides of the knee, force sensor apparatus including:
    a sensor body;
    a pad; and
    at least one force sensing surface.

12. The adjustable femoral provisional component of claim 1, wherein the anterior patellar groove member includes a plurality of tangs for mating with a plurality of apertures in the anterior surface of the femoral adjustment member.

13. An adjustable femoral provisional system comprising:
a femoral adjustment member securable to a distal femur and adapted to enable ligament balancing during a surgical procedure on a knee, the femoral adjustment member including a medial condylar paddle and a lateral condylar paddle, the medial condylar paddle coupled to a medial adjustment mechanism and the lateral condylar paddle coupled to a lateral adjustment mechanism, the adjustment mechanisms configured to enable separate adjustment of medial and lateral gap distances between a distal surface of the femoral adjustment member and a east one resected surface of the distal femur; and
a plurality of anterior patellar groove members, each anterior patellar groove member couplable with an anterior surface of the femoral adjustment member to form a provisional distal femoral surface, each anterior patellar groove member including:
a proximal surface configured to contact an anterior resected surface of the distal femur; and
an augment element disposable between a portion of the femoral adjustment member and a distal resected surface of the distal femur when each anterior patellar groove member is coupled with the femoral adjustment member, the augment element adapted to assist in ligament balancing with the knee in extension.

14. The adjustable femoral provisional system of claim 13, wherein each anterior patellar groove members of the plurality of anterior patellar groove members include an augment element with a different width configured to maintain a different gap distance between the femoral adjustment member and the distal resected surface.

15. The adjustable femoral provisional system of claim 13, wherein each anterior patellar groove member includes a plurality of tangs for mating with a plurality of apertures in the anterior surface of the femoral adjustment member.

16. The adjustable femoral provisional system of claim 13, wherein each anterior patellar groove member includes a medial adjustment aperture to access the medial adjustment mechanism and a lateral adjustment aperture to access the lateral adjustment mechanism.

17. The adjustable femoral provisional system of claim 13, wherein the femoral adjustment member and each anterior patellar groove member, when coupled, form a trochlear groove oriented along a substantially anterior-to-posterior axis through at least a portion of the provisional distal femoral surface.

18. A provisional system comprising:
a femoral adjustment member attachable to a distal femur to enable ligament balancing during a surgical procedure, the femoral adjustment member including a medial adjustment mechanism and a lateral adjustment mechanism, the medial and lateral adjustment mechanisms configured to adjust a orientation of a distal surface of the femoral adjustment member with respect to resected surfaces of the distal femur; and
an anterior patellar groove member couplable with an anterior portion of the femoral adjustment member to form a provisional distal femoral surface, the anterior patellar groove member including a proximal surface configured to contact at least an anterior resected surface of the distal femur, and an augment element disposable between a portion of the femoral adjustment member and a distal resected surface of the distal femur when the anterior patellar groove member is coupled with the femoral adjustment member the augment element adapted to assist in ligament balancing with the knee in extension.

19. The provisional system of claim 18, further comprising a force sensor apparatus adapted to slidably contact the provisional distal femoral surface and provide force or pressure readings separately from the medial and lateral sides of the knee, force sensor apparatus including:
a sensor body;
a pad; and
at least one force sensing surface.

* * * * *

UNITED STATES PATENT AND TRADEMARK OFFICE
CERTIFICATE OF CORRECTION

PATENT NO.         : 9,622,761 B2                                  Page 1 of 1
APPLICATION NO.    : 14/564451
DATED              : April 18, 2017
INVENTOR(S)        : Chana et al.

It is certified that error appears in the above-identified patent and that said Letters Patent is hereby corrected as shown below:

On the Title Page

In Column 2, under "Foreign Patent Documents", Line 1, delete "FR" and insert --WO-- therefor In Item (57), in "Abstract", in Column 2, Line 6, delete "intermedullary" and insert --intramedullary-- therefor In Item (57), in "Abstract", in Column 2, Line 10, delete "and or" and insert --and/or-- therefor In Item (57), in "Abstract", in Column 2, Line 12, delete "an" and insert --on-- therefor On page 2, in Column 2, under "Other Publications", Line 22, delete "Jan. 10, 2013"," and insert --Jan. 13, 2010",-- therefor In the Claims In Column 22, Line 29, in Claim 5, delete "member," and insert --member-- therefor In Column 23, Line 12, in Claim 13, delete "a east" and insert --at least-- therefor Signed and Sealed this
Tenth Day of April, 2018

Andrei Iancu
*Director of the United States Patent and Trademark Office*